(12) United States Patent
Gill et al.

(10) Patent No.: US 11,673,896 B2
(45) Date of Patent: Jun. 13, 2023

(54) PYRIDINE COMPOUNDS AS ALLOSTERIC SHP2 INHIBITORS

(71) Applicant: Revolution Medicines, Inc., Redwood City, CA (US)

(72) Inventors: Adrian Gill, Redwood City, CA (US); Naing Aay, Redwood City, CA (US); Kevin Mellem, Redwood City, CA (US); Andreas Buckl, Redwood City, CA (US); Elena S. Koltun, Redwood City, CA (US); Christopher Semko, Redwood City, CA (US); Gert Kiss, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 0 days.

(21) Appl. No.: 16/518,796

(22) Filed: Jul. 22, 2019

(65) Prior Publication Data

US 2020/0017517 A1 Jan. 16, 2020

Related U.S. Application Data

(63) Continuation of application No. PCT/US2018/013018, filed on Jan. 9, 2018.

(60) Provisional application No. 62/449,529, filed on Jan. 23, 2017.

(51) Int. Cl.
*C07D 401/04* (2006.01)
*C07D 401/14* (2006.01)
*C07D 491/107* (2006.01)

(52) U.S. Cl.
CPC ....... *C07D 491/107* (2013.01); *C07D 401/04* (2013.01); *C07D 401/14* (2013.01)

(58) Field of Classification Search
CPC . C07D 491/107; C07D 401/04; C07D 401/14
USPC ......................................................... 546/16
See application file for complete search history.

(56) References Cited

U.S. PATENT DOCUMENTS

| | | | |
|---|---|---|---|
| 2,572,728 A | 10/1951 | Hultquist | |
| 2,636,882 A * | 4/1953 | Dunlop | C07D 213/65 546/250 |
| 3,701,779 A * | 10/1972 | Donninger | C07D 213/66 546/292 |
| 4,687,848 A | 8/1987 | Brunnmueller et al. | |
| 5,262,564 A | 11/1993 | Kun et al. | |
| 6,921,762 B2 | 7/2005 | Cai | |
| 7,863,288 B2 | 1/2011 | Ibrahim et al. | |
| 8,324,200 B2 | 12/2012 | Li et al. | |
| 8,703,770 B2 | 4/2014 | Coleman et al. | |
| 9,169,261 B2 | 10/2015 | Fan et al. | |
| 9,394,368 B2 | 7/2016 | Brogdon et al. | |
| 10,590,090 B2 | 3/2020 | Jogalekar et al. | |

| | | |
|---|---|---|
| 2004/0213795 A1 | 10/2004 | Collins et al. |
| 2004/0220189 A1 | 11/2004 | Sun et al. |
| 2006/0189664 A1 | 8/2006 | Barth et al. |
| 2008/0176309 A1 | 7/2008 | Wu et al. |
| 2009/0325973 A1 | 12/2009 | Watterson et al. |
| 2010/0190980 A1 | 7/2010 | Umemiya et al. |
| 2011/0257184 A1 | 10/2011 | Qu et al. |
| 2012/0034186 A1 | 2/2012 | Wu et al. |
| 2012/0065205 A1 | 3/2012 | Mercer et al. |
| 2012/0266264 A1 | 10/2012 | Lee |
| 2012/0330012 A1 | 12/2012 | Frank et al. |
| 2013/0005949 A1 | 1/2013 | Fertig et al. |
| 2014/0154179 A1 | 6/2014 | Fan et al. |
| 2016/0031976 A1 | 2/2016 | Seubert et al. |
| 2017/0042881 A1 | 2/2017 | Fagin et al. |
| 2018/0200381 A1 | 7/2018 | Kannan |
| 2019/0210977 A1 | 7/2019 | Jogalekar et al. |
| 2019/0290649 A1 | 9/2019 | Xie et al. |
| 2020/0017511 A1 | 1/2020 | Blank et al. |
| 2020/0108071 A1 | 4/2020 | Chin et al. |
| 2020/0339552 A1 | 10/2020 | Li et al. |
| 2020/0368238 A1 | 11/2020 | Nichols et al. |
| 2020/0407372 A1 | 12/2020 | Koltun et al. |
| 2021/0053989 A1 | 2/2021 | Zou |
| 2021/0101870 A1 | 4/2021 | Koltun et al. |
| 2021/0154190 A1 | 5/2021 | Wildes |
| 2022/0031695 A1 | 2/2022 | Pitzen et al. |
| 2022/0073521 A1 | 3/2022 | Zou et al. |
| 2022/0127271 A1 | 4/2022 | Wan et al. |

FOREIGN PATENT DOCUMENTS

| | | |
|---|---|---|
| CN | 103181918 A | 7/2013 |
| CN | 103554038 | 2/2014 |
| CN | 105916845 A | 8/2016 |
| CN | 110156786 A | 8/2019 |
| EA | 201691442 A1 | 12/2016 |
| EP | 0 088 593 A2 | 9/1983 |
| EP | 0 579 835 A1 | 1/1994 |
| GB | 1459571 A | 12/1976 |
| JP | S5762269 A | 4/1982 |
| JP | H02-049775 A | 2/1990 |

(Continued)

OTHER PUBLICATIONS

Bhatia et al A review on Bioisosterism (Year: 2011).*
Banker et al Modern Pharmaceutics (Year: 1976).*
Manfred Wolff Burger's Medicinal Chemistry and Drug Discovery. (Year: 1995).*
Ellsworth et al., "Discovery of pyrazine carboxamide CBI antagonists: The introduction of a hydroxyl group improves the pharmaceutical properties and in vivo efficacy of the series," Bioorganic & Medicinal Chemistry Letters, vol. 17, No. 14, Jul. 1, 2007, pp. 3978-3982.
Giori et al., "Synthesis of 6,7-Disubstituted Pteridine-2,4-Diones," Heterocycles, vol. 32, No. 1, 1991, 6 pages.
Jordan, "Tamoxifen: A Most Unlikely Pioneering Medicine," Nature Reviews: Drug Discovery, vol. 2, Mar. 2003, 205-213.

(Continued)

*Primary Examiner* — Niloofar Rahmani
(74) *Attorney, Agent, or Firm* — Cooley LLP

(57) ABSTRACT

The present disclosure is directed to inhibitors of SHP2 and their use in the treatment of disease. Also disclosed are pharmaceutical compositions comprising the same.

16 Claims, No Drawings

(56) References Cited

FOREIGN PATENT DOCUMENTS

| | | |
|---|---|---|
| JP | H04-112877 A | 4/1992 |
| JP | H09510987 A | 11/1997 |
| JP | 2007277097 A | 10/2007 |
| JP | 2007530434 A | 11/2007 |
| JP | 2010520238 A | 6/2010 |
| JP | 2013526526 A | 6/2013 |
| JP | 2013531025 A | 8/2013 |
| JP | 2017502993 A | 1/2017 |
| JP | 2017502994 A | 1/2017 |
| JP | 2017503000 A | 1/2017 |
| JP | 2017522346 A | 9/2019 |
| WO | WO 93/09664 | 5/1993 |
| WO | WO 97/29109 A1 | 8/1997 |
| WO | WO 98/56376 | 12/1998 |
| WO | WO 01/16097 A1 | 3/2001 |
| WO | WO 2001/060806 A2 | 8/2001 |
| WO | WO 03/029422 A2 | 4/2003 |
| WO | WO 2003045924 A1 | 6/2003 |
| WO | WO 03/082191 A2 | 10/2003 |
| WO | WO 2004/024719 A1 | 3/2004 |
| WO | WO 2004099201 A1 | 11/2004 |
| WO | WO 2004/111034 | 12/2004 |
| WO | WO 2005/028480 A2 | 3/2005 |
| WO | WO 2005/035532 A1 | 4/2005 |
| WO | WO 2005/040151 | 5/2005 |
| WO | WO 2005/000817 A2 | 6/2005 |
| WO | WO 2005/106286 | 11/2005 |
| WO | WO 2006/002284 A1 | 1/2006 |
| WO | WO 2006/071759 A2 | 7/2006 |
| WO | WO 2006/113704 | 10/2006 |
| WO | WO 2007/048067 | 4/2007 |
| WO | WO 2007/106142 A2 | 9/2007 |
| WO | WO 2007/131991 A1 | 11/2007 |
| WO | WO-2007127448 A1 | 11/2007 |
| WO | WO 2007/145921 A1 | 12/2007 |
| WO | WO 2007/138072 A2 | 2/2008 |
| WO | WO 2007/138072 A3 | 2/2008 |
| WO | WO 2008/122615 | 10/2008 |
| WO | WO 2008/138842 A1 | 11/2008 |
| WO | WO 2008/138843 A1 | 11/2008 |
| WO | WO 2009/020642 A1 | 2/2009 |
| WO | WO-2009025823 A1 | 2/2009 |
| WO | WO 2010/011666 A2 | 1/2010 |
| WO | WO 2011/022440 A2 | 2/2011 |
| WO | WO 2011/154327 A1 | 12/2011 |
| WO | WO 2012/055942 | 5/2012 |
| WO | WO 2012/116237 A2 | 8/2012 |
| WO | WO 2013/105063 | 7/2013 |
| WO | WO 2014023385 A1 | 2/2014 |
| WO | WO 2014/072881 A1 | 5/2014 |
| WO | WO 2014/113584 A1 | 7/2014 |
| WO | WO 2014/121885 | 8/2014 |
| WO | WO 2015/107493 A1 | 7/2015 |
| WO | WO 2015/107494 A1 | 7/2015 |
| WO | WO 2015/107495 A1 | 7/2015 |
| WO | WO 2016/007731 A1 | 1/2016 |
| WO | WO-2016081290 A1 | 5/2016 |
| WO | WO 2016/103155 A1 | 6/2016 |
| WO | WO 2016/112295 A1 | 7/2016 |
| WO | WO-2016125169 A1 | 8/2016 |
| WO | WO 2016/161282 A1 | 10/2016 |
| WO | WO 2016/203404 A1 | 12/2016 |
| WO | WO 2016/203405 A1 | 12/2016 |
| WO | WO 2016/203406 A1 | 12/2016 |
| WO | WO 2017/059207 A1 | 4/2017 |
| WO | WO 2017/079723 A1 | 5/2017 |
| WO | WO 2017/156397 A1 | 9/2017 |
| WO | WO 2017/211303 A1 | 12/2017 |
| WO | WO 2017/216706 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/130928 A1 | 7/2018 |
| WO | WO 2018/136264 A1 | 7/2018 |
| WO | WO 2018/136264 A1 | 7/2018 |
| WO | WO 2018/136265 A1 | 7/2018 |
| WO | WO 2018/172984 A1 | 9/2018 |
| WO | WO 2018/218133 A1 | 11/2018 |
| WO | WO 2019/051084 A1 | 3/2019 |
| WO | WO 2019/075265 A1 | 4/2019 |
| WO | WO 2019/118909 A1 | 6/2019 |
| WO | WO 2019/199792 A1 | 10/2019 |
| WO | WO 2019/212990 A1 | 11/2019 |
| WO | WO 2019/212991 A1 | 11/2019 |
| WO | WO 2020/055761 A1 | 3/2020 |
| WO | WO 2020/061101 A1 | 3/2020 |
| WO | WO 2020/106647 A2 | 5/2020 |
| WO | WO-2020094104 A1 | 5/2020 |
| WO | WO-2020/132597 A1 | 6/2020 |
| WO | WO-2020108590 A1 | 6/2020 |
| WO | WO 2021/091967 A | 5/2021 |

OTHER PUBLICATIONS

Vippagunta et al., "Crystalline solids," Advanced Drug Delivery Reviews 48, 2001, 3-26.
Wolff, "Burger's Medicinal Chemistry and Drug Discovery," Fifth Edition, vol. 1: Principles and Practice, New York: John Wiley & Sons, 1994, 975-977.
Wustrow D.J. et al., "Aminopyrazine CB1 receptor inverse agonists," Bioorganic & Medicinal Chemistry Letters, vol. 18, No. 11, 2008, p. 3376-3381.
Database Registry, Compound with CAS Registry No. 78246-19-2. 3-Methyl-5-(2-methylpropyl)-2-(phenylthio)pyrazine. Nov. 16, 1984.
Database Registry, Compound with CAS Registry No. 15033-82-6. 4-[(3,5,6-Trimethyl-2-pyrazinyl)sulfonyl]benzenamine. Nov. 16, 1984.
U.S. Appl. No. 16/518,798, filed Jan. 9, 2018, Blank et al.
International Search Report and Written Opinion dated Dec. 20, 2017, for PCT/US2017/041577, 18 pages.
International Search Report and Written Opinion dated Sep. 21, 2018, for PCT/US2018/013018, 10 pages.
International Search Report and Written Opinion dated Apr. 5, 2018, for PCT/US2018/013023, 13 pages.
International Search Report and Written Opinion dated Jan. 24, 2019, for PCT/US2018/055502, 16 pages.
International Search Report and Written Opinion dated Dec. 12, 2018, for PCT/US2018/049744, 13 pages.
International Search Report and Written Opinion dated Feb. 20, 2019, for PCT/US2018/065817, 11 pages.
Chen et al., "Allosteric inhibition of SHP2 phosphatase inhibits cancers driven by receptor tyrosine kinases," Nature 2016, 535, 148-152.
Chen et al., "Identification of demethylincisterol A3 as a selective inhibitor of protein tyrosine phosphatase Shp2," Eur J Pharmacol. Jan. 15, 2017;795:124-133.
Fortanet et al., "Allosteric Inhibition of SHP2: Identification of a Potent, Selective, and Orally Efficacious Phosphatase Inhibitor," J. Med. Chem. 2016, 59, 7773-7782.
Larochelle et al., "Identification of an allosteric benzothiazolopyrimidone inhibitor of the oncogenic protein tyrosine phosphatase SHP2," Bioorg. Med. Chem. 2017, 17, 31394-31399.
Meurer et al., "Synthesis and SAR of 5,6-diarylpyridines as human CB1 inverse agonists," Bioorg Med Chem Lett. Feb. 1, 2005;15(3):645-51.
Mohi et al., "The role of Shp2 (PTPN11) in cancer," Curr Opin Genet Dev. Feb. 2007;17(1):23-30.
Nichols et al., "RAS nucleotide cycling underlies the SHP2 phosphatase dependence of mutant BRAF-, NF1- and RAS-driven cancers," Nat Cell Biol. Sep. 2018;20(9):1064-1073.
Ruess et al., "Mutant KRAS-driven cancers depend on PTPN11/SHP2 phosphatase," Nat Med. Jul. 2018;24(7):954-960.
Xie et al., "Allosteric Inhibitors of SHP2 with Therapeutic Potential for Cancer Treatment," J. Med. Chem. 2017, 60, 10205-10219.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6.

(56) References Cited

OTHER PUBLICATIONS

Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8.
Database Registry [Online] Chemical Abstracts Service, Columbus, Ohio, US; Nov. 16, 1984 (Nov. 16, 1984), XP002787395, retrieved from stn Database accession No. 86663-20-9 compound with CAS registry No. 86663-20-9.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1.
Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3.
Database Registry [Online] Chemical Abstracts Service, Columbus, Ohio, US; Apr. 6, 1990 (Apr. 6, 1990), XP002787400, Database accession No. 126317-60-0 compound with CAS registry No. 126317-60-0.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9.
International Search Report dated Sep. 2, 2019, for International Application No. PCT/US2019/026543, 9 pages.
Anonymous: "RMC-4630," Jul. 20, 2018 (Jul. 20, 2018), pp. 1-1, Retrieved from the Internet: URL:https://integrity.clarivate.com/integrity/xmlxsl/pk_prod_list.exec_form_pro_pr.
Belanger, David B. et al., "Discovery of imidazo [1, 2-a] pyrazine-based Aurora kinase inhibitors," Bioorganic & medicinal chemistry letters 20.17 (2010): 5170-5174.
Chen et al., "Discovery of a novel shp2 protein tyrosine phosphatase inhibitor," Mol Pharmacol. Aug. 2006; 70(2):562-70.
Domagala et al., "KRAS mutation testing in colorectal cancer as an example of the pathologist's role in personalized targeted therapy: a practical approach," Pol J Pathol 3: 145-164 (2012).
Fedele et al., "SHP2 Inhibition Prevents Adaptive Resistance to MEK inhibitors in Multiple Cancer Models," Cancer Discov. Oct. 2018; 8(10): 1237-1249.
Larochelle et al., "Structural and Functional Consequences of Three Cancer-Associated Mutations of the Oncogenic Phosphatase SHP2," Biochemistry, vol. 55, No. 15, Apr. 11, 2016, pp. 2269-2277.
Larochelle et al. "Structural reorganization of SHP2 by oncogenic mutations and implications for oncoprotein resistance to allosteric inhibition", Nature Communications, vol. 9, No. 1, Oct. 30, 2018, 10 pages.
Masuda H. et al., "Synthesis of Alkoxy-, (Alkylthio)-, Phenoxy-, and (Phenylthio)pyrazines and their Olfactive Properties," J. Agric. Food Chem., 1986, 34(2), pp. 377-381.

Sayer, James Richard, "The Synthesis of Imidazo [1, 2-a] pyrazines as Inhibitors of the VirB11 ATPase and their Incorporation into Bivalent Compounds," Diss. UCL (University College London), 2013, 396 pages.
Sun et al., "Selective inhibition of leukemia-associated SHP2E69K mutant by the allosteric SHP2 inhibitor SHP099," Leukemia, Nature Publishing Group UK, London, vol. 32, No. 5, Jan. 30, 2018, 4 pages.
Xiao et al., "Myeloid-restricted ablation of Shp2 restrains melanoma growth by amplifying the reciprocal promotion of CXCL9 and IFN-γ production in tumor microenvironment," Oncogene, May 7, 2018, 13 pages.
Yamanishi Y. et al., "Syntheses of trimethylpyrazines and their antibacterial properties," Yakugaku Zasshi, 1967, 87(1), pp. 105-107.
Zhao et al., "SHP2 inhibition triggers anti-tumor Immunity and synergizes with PD-1 blockade," Acta Pharmaceutica Sinica B 2019;9(2):304-315.
Hydrates, products of the addition of water (hydration) to molecules, atoms, or ions. M. b. gaseous, liquid, and solid; the last called, crystal hydrates. XUMUK, Wayback internet archive machine, Oct. 27, 2007. (machine translated from Russian) [retrieved Sep. 3, 2021] Retrieved from the Internet: <URL: https://xumuk.ru/encyklopedia/1022.html>.
Monson et al., "The reactions of some ketones with hexamethylphosphoric triamide a novel synthesis of 3,5-dialkyl-2,6-diphenylpyridines,".
Patani et al., "Bioisosterism: A Rational Approach in Drug Design," Chemical Reviews, 1996, 96, 3147-3176.
Vernier et al., "Thioether benzenesulfonamide inhibitors of carbonic anhydrases II and IV: structure-based drug design, synthesis, and biological evaluation," Bioorganic & Medicinal Chemistry, vol. 18, Issue 9, May 1, 2010, pp. 3307-3319.
Anonymous: 3-Amino-6-phenyl-4-trifluoromethylpyridine, C12H9F3N2, PubChem CID 129781129, retrieved from https://pubchem.ncbi.nlm.nih.gov/compound/129781129 on Oct. 20, 2021. (8 pages).
Belton, et al., A Novel N→S Oxygen Migration in 2,1,3-Benzoxadiazole Systems, Proceedings of the Royal Irish Academy. Section B: Biological, Geological, and Chemical Science, Royal Irish Academy, 1974, pp. 185-192, vol. 74.
Boamah, et al., Pyridazines. XXXVII†‡. Novel triazanaphthalene derivatives via intramolecular cyclization reactions of vic-disubstituted pyridazines, Journal of Heterocyclic Chemistry, 1988, pp. 879-883, vol. 25, No. 3.
Database Registry, Compound with CAS Registry No. 1119718-06-7—1,4-Dioxa-8-azaspiro[4.5]decane, 8-[5-(6,7-dimethoxy-4-cinnolinyl)-3-methyl-2-pyridinyl], Mar. 12, 2009.
Database Registry, Compound with CAS Registry No. 1384576-77-5, 1,4-Dioxa-8-azaspiro[4.5]decane, 8-[6-(3-fluorophenyl)-4-methyl-3- pyridazinyl], Jul. 27, 2012.
CAS Registry No. 1349160-17-3; STN Entry Date Dec. 5, 2011; 5-(2-Chloro-4-methoxyphenyl)-3,6-diethyl-N-(1-ethylbutyl)-2-pyrazinamine.
CAS Registry No. 1349131-06-1; STN Entry Date Dec. 5, 2011; 3,6-Diethyl-N-(1-ethylpropyl)-5-[6-(1-methylethyl)-2-[(2-methylpropyl)amino]-3-pyridinyl]-2-pyrazinamine.
CAS Registry No. 1350134-68-7; STN Entry Date Dec. 7, 2011; N-[(3S,4S)-4-Butoxytetrahydro-3-furanyl]-5-(2-chloro-4-methoxyphenyl)-3,6-diethyl-2-pyrazinamine.
CAS Registry No. 1027540-93-7; STN Entry Date Jun. 12, 2008; 5-(2,4-Dichlorophenyl)-N-(4-ethoxy-1-methyl-3-pyrrolidinyl)-3,6-diethyl-2-pyrazinamine.
CAS Registry No. 1026750-06-0; STN Entry Date Jun. 9, 2008; 5-[2-(Cyclohexyloxy)-6-methyl-4-pyrimidinyl]-2,3-dihydro-2-[3-methyl-5-(4-methyl-1-piperazinyl)-2-pyrazinyl]-2-thiazolamine.
CAS Registry No. 1918768-32-7, Entry date May 26, 2016, 4-Piperidinamine, 1-[2-(trifluoromethyl)pyrazolo[1,5-a]pyrazin-4-yl]—(CA Index Name).
CAS Registry No. 1918848-03-9, Entry date May 26, 2016, 4-Piperidinamine, 1-[2-(1-methylethyl)pyrazolo[1,5-a]pyrazin-4-yl]—(CA Index Name).

(56) References Cited

OTHER PUBLICATIONS

CAS Registry No. 777873-55-9, Entry date Nov. 10, 2004, 2,1,3-Benzoxadiazole, 4-(3-methyl-1-piperidinyl)-7-[(3-methyl-1-piperidinyl)sulfonyl]—(CA Index Name).
CAS Registry No. 777873-58-2, Entry date Nov. 10, 2004, 2,1,3-Benzoxadiazole, 4-(4-methyl-1-piperidinyl)-7-[(4-methyl-1-piperidinyl)sulfonyl]—(CA Index Name).
CAS Registry No. 777880-58-7 Entry date Nov. 10, 2004, 2,1,3-Benzoxadiazole, 4-(1-piperidinyl)-7-(1-piperidinylsulfonyl)—(CA Index Name).
European Patent Office, European Office Action for European Application No. 18701883.3, dated Sep. 15, 2021, 6 pages.
European Patent Office, International Preliminary Report on Patentability for pct International Application No. PCT/US2019/026543, dated Oct. 13, 2020, 15 pages.
Jiang, et al., Optimal therapeutic positioning of a selective bi-steric inhibitor of MTORC1 in geneticaly defined cancers, European Journal of Cancer, Oct. 1, 2020, 2 pages, vol. 138.
Anonymous: RMC-4630, Jul. 20, 2018, pp. 1-1, Retrieved from the Internet: URL:https://integrity.clarivate.com/integrity/xmlxsl/pk_prod_list.exec_form_pro_pr.
Belanger, David B. et al., Discovery of imidazo [1, 2-a] pyrazine-based Aurora kinase inhibitors, Bioorganic & medicinal chemistry letters, 2010, pp. 5170-5174, vol. 20, No. 17.
Chen et al., Discovery of a novel shp2 protein tyrosine phosphatase inhibitor, Mol Pharmacol., Aug. 2006, pp. 562-570, vol. 70, No. 2.
Dardaei, et al., SHP2 inhibition restores sensitivity in ALK-rearranged non-small-cell lung cancer resistant to ALK inhibitors, Nature Medicine, Mar. 5, 2018, pp. 512-517, vol. 24, No. 4.
Dardaei, et al., Supplemental Material, SHP2 inhibition restores sensitivity in ALK-rearranged non-small-cell lung cancer resistant to ALK inhibitors, Nature Medicine, Mar. 5, 2018, pp. 1-58, vol. 24.
Davare, et al., Foretinib is a potent inhibitor of oncogenic ROS1 fusion proteins, PNAS, Nov. 11, 2013, pp. 19519-19524, vol. 110, No. 48.
Database Registry, RN 1629858-36-1, entered STN Oct. 23, 2014.
Database Registry, RN 1028262-30-7, entered STN Jun. 15, 2008.
Database Registry, RN 1027952-21-1, entered STN Jun. 13, 2008.
Database Registry, RN 1026418-24-5, entered STN Jun. 8, 2008.
Database Registry, RN 1026270-53-0, entered STN Jun. 8, 2008.
Database Registry, RN 1026250-49-6, entered STN Jun. 8, 2008.
Database Registry, RN 1334203-33-6, entered STN Sep. 30, 2011.
Database Registry, RN 1334203-32-5, entered STN Sep. 30, 2011.
Database Registry, RN 900624-41-1, entered STN Aug. 11, 2006.
Database Registry, RN 893813-11-1, entered STN Jul. 17, 2006.
Database Registry, RN 893813-68-2, entered STN Jul. 17, 2006.
Database Registry, RN 590404-14-1, entered STN Sep. 22, 2003.
Database Registry, RN 1860803-32-2, entered STN Feb. 5, 2016.
European Patent Office, European Office Action for European Application No. 18701882.5, dated Mar. 23, 2022, 4 pages.
Huang, et al., Discovery of First-in-Class, Potent, and Orally Bioavailable Embryonic Ectoderm Development (EED) Inhibitor with Robust Anticancer Efficacy, J. Med. Chem., Jan. 16, 2017, pp. 2215-2226, vol. 60, No. 6.
Leroy, et al., Di-tert-butyl (methyl) phosphonium tetrafluoroborate, e-EROS Encyclopedia of Reagents for Organic Synthesis, Dec. 31, 2015, pp. 1-7.
Neel, et al., Differential Subcellular Localization Regulates Oncogenic Signaling by ROS1 Kinase Fusion Proteins, Cancer Res, Dec. 11, 2018, pp. 546-556, vol. 79, No. 3.
Nichols et al., Efficacy of SHP2 phosphatase inhibition in cancers with nucleotide-cycling oncogenic RAS, RAS-GTP dependent oncogenic BRAF and NF1 loss, bioRxiv preprint first posted online Sep. 14, 2017, 16 pages.
Ozawa et al.,The importance of CH/phydrogen bonds in rational drug design: An abinitio fragment molecular orbital study to leukocyte-specific protein tyrosine (LCK) kinase, Dec. 31, 2008, Bioorganic & Medicinal Chemistry, pp. 10311-10318, vol. 16.
Rauen, et al., The RASopathies, Annu Rev Genomics Hum Genet. 2013, pp. 355-369, vol. 14.
Voena, et al., The Tyrosine Phosphatase Shp2 Interacts with NPM-ALK and Regulates Anaplastic Lymphoma Cell Growth and Migration, Cancer Res, Apr. 24, 2007, pp. 4278-4286, vol. 67, No. 9.
Wang et al., Palladium-Catalyzed Direct Heck Arylation of Dual π-Deficient/π-Excessive Heteroaromatics. Synthesis of C-5 Arylated Imidazo[1, 5-a]pyrazin, Organic Letters, Jun. 25, 2008, pp. 2215-2226, vol. 10, No. 14.
Yap, et al, The NF1 gene revisited—from bench to bedside, Oncotarget, Aug. 2014, pp. 5873-5892, vol. 5, No. 15.
Zou, et al., PF-06463922 is a potent and selective next-generation ROS1/ALK inhibitor capable of blocking crizotinib-resistant ROS1 mutations, PNAS, Mar. 2, 2015, pp. 3493-3498, vol. 112, No. 11.
Adam et al., "Concise synthesis of 1H-pyrazin-2-ones and 2-aminopyrazines" Synlett (11): 2004 2031-2033 compounds 6a, 6c and 6d.
Dayakar et al., "Synthesis and antimycobacterial activity of 1 H-1,2,3-triazolylisonicotinohydrazi," Indian Journal of Chemistry, Section B: Organic Chemistry Including Medicinal Chemistry 55B (7), (2016), 882-887 intermediates 9c to 9f.
Fialkov Y., "Solvent as a means of controlling a chemical process", Publishing house "Chemistry", 1990, p. 240.
Li, H.-L et al., Exploring the effect of D61G mutation on SHP2 cause gain of function activity by a molecular dynamics study. J. Biomol. Struct. Dyn., Nov. 24, 2017, vol. 36, No. 14, pp. 3856-3868.
Perez et al., "Palladium-Catalyzed C,N-Cross Coupling Reactions of 3-Halo-2-aminopyridines," Organic Letters 13 (8): 2011; 1984-1987 compound 5 of Figure 2; compounds 12 and 13 of Scheme 2.
Ran et al., "Sticking It to Cancer with Molecular Glue for SHP2" Cancer Cell. Aug. 8, 2016;30(2):194-196.
Yatsyuk V. Ya et, al,. "General principles of xenobiotic metabolism as a basis for the development of methods for the synthesis of prodrugs", Elective course textbook, 2009, pp. 71-79.
Akhapkina. V.I et al., "Fundamentals of modulatory concept and classification of modulatory drugs," RMZh, N19, 2012, pp. 933-951.
Amato, C. et al., "Modulation of a proteolytic enzyme activity by means of photochromic inhibitor", Journal of Photochemistry and Photobiology B: Biology, 1995, vol. 28(1), p. 71-75.
Belikov, V.G, "Pharmaceutical Chemistry. Chapter 2.6 Relationship between the chemical structure, properties of substances and their effect on the body- M," MEDpress-inform, 2007, pp. 27-29, and English translation, 14 pages.
CAS Registry No. 1119717-53-1, Entry date Mar. 12, 2009.
CAS Registry No. 174531-55-6, Entry date Mar. 26, 1996.
CAS Registry No. 3657-73-6, Entry date Nov. 16, 1984.
Database Registry, RN 1957154-25-4, 1956595-47-3, entered STN Jul. 21, 2016.
Database Registry, RN 1949800-28-5, entered STN Jul. 11, 2016.
Database Registry, RN 1952095-25-8, entered STN Jul. 14, 2016.
Database Registry, RN 1953046-94-0, 1952680-38, entered STN Jul. 15, 2016.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/m_mater/docs/osnovi_med_pomoshi.pdf?ysclid=l5wi7xgplo450927514.
Krosig, U. et al., "Expanding the Genetic Alphabet: Pyrazine Nucleosides That Support a Donor-Donor-Acceptor Hydrogen-Bonding Pattern," Helv. Chim. Acta 2004, v.87, pp. 1299-1324.
Mehta, V. et al., "Microwave-Assisted Palladium-Catalyzed Phosphonium Coupling of 2(1H)-Pyrazinones," J. Org. Chem. 2010, 75, 3, 976-979.
Pisaneschi, F. et al., "The 3S Enantiomer Drives Enolase Inhibitory Activity in SF2312 and Its Analogues", Molecules, 2019, vol. 24(13), 2510, p. 1-18.
Sansfacon et. al., "SHP-2 phosphatase contributes to KRAS-driven intestinal oncogenesis but prevents colitis-associated cancer development," Oncotarget. Oct. 4, 2016;7(40):65676-65695.
Tol, J. et al., "Chemotherapy, bevacizumab, and cetuximab in metastatic colorectal cancer," N Engl J Med, Feb. 5, 2009, vol. 360(6), pp. 563-572.

(56) References Cited

OTHER PUBLICATIONS

Yu, H. A. et al., "A phase 1/2 trial of ruxolitinib and erlotinib in patients with EGFR-mutant lung adenocarcinomas with acquired resistance to erlotinib," Journal of Thoracic Oncology, 2017, vol. 12(1), pp. 102-109.
Zefirova, On et al., "On the Origin and Development if the Concept of Bioisoterism," VESTN MOSK UN-TA SER 2 CHEMISTRY, 2002, vol. 43(4), pp. 251-256.
Database Registry, RN 893806-50-3, entered STN Jul. 17, 2006, 1 page.
Database Registry, RN 893807-90-4, entered STN Jul. 17, 2006, 1 page.
Database Registry, RN 893808-63-4, entered STN Jul. 17, 2006, 1 page.
Database Registry, RN 893810-11-2, entered STN Jul. 17, 2006, 1 page.
9-(4-chlorophenyl)-5-(4-morpholinyl)tetrazolo[1,5-c]-thieno[3,2-e]pyrimidine, entered STN Jul. 17, 2006, 1 page.
9-(4-chlorophenyl)-5-(4-morpholinyl)thieno[3,2-e]-1,2,4-triazolo[4,3-c]pyrimidineentered STN Jul. 17, 2006, 1 page.
9-phenyl-5-(1-pyrrolidinyl)tetrazolo[1,5-c]thieno[3,2-e]pyrimidine, entered STN Jul. 17, 2006, 1 page.
9-phenyl-5-(1-pyrrolidinyl)thieno[3,2-e]-1,2,4-triazolo[4,3-c]pyrimidine, entered STN Jul. 17, 2006, 1 page.
Database Registry, RN 893294-18-3, entered STN Jul. 17, 2006, 1 page.
Database Registry, RN 893792-24-0, entered STN Jul. 17, 2006, 1 page.
Database Registry, RN 893792-68-2, entered STN Jul. 17, 2006, 1 page.
Database Registry, RN 893794-10-0, entered STN Jul. 17, 2006, 1 page.
Database Registry, RN 893795-14-7, entered STN Jul. 17, 2006, 1 page.
Database Registry, RN 893796-38-8, entered STN Jul. 17, 2006, 1 page.
Database Registry, RN 893796-42-4, entered STN Jul. 17, 2006, 1 page.
Database Registry, RN 893797-57-4, entered STN Jul. 17, 2006, 1 page.
Database Registry, RN 893797-61-0, entered STN Jul. 17, 2006, 1 page.
Database Registry, RN 893799-39-8, entered STN Jul. 17, 2006, 1 page.
Database Registry, RN 893799-43-4, entered STN Jul. 17, 2006, 1 page.
Database Registry, RN 893799-47-8, entered STN Jul. 17, 2006, 1 page.
Database Registry, RN 893801-34-8, entered STN Jul. 17, 2006, 1 page.
Database Registry, RN 893803-59-3, entered STN Jul. 17, 2006, 1 page.

* cited by examiner

PYRIDINE COMPOUNDS AS ALLOSTERIC SHP2 INHIBITORS

CROSS-REFERENCE TO RELATED APPLICATIONS

This application is a continuation of International Patent Application No. PCT/US2018/013018, filed Jan. 9, 2018, which claims the benefit of U.S. Provisional Application No. 62/449,529, filed Jan. 23, 2017, the contents of each of which are incorporated herein by reference in their entirety.

FIELD OF THE DISCLOSURE

The present disclosure relates to inhibitors of protein tyrosine phosphatase SHP2 useful in the treatment of diseases or disorders. Specifically, this disclosure is concerned with compounds and compositions inhibiting SHP2, methods of treating diseases associated with SHP2, and methods of synthesizing these compounds.

BACKGROUND OF THE DISCLOSURE

SH2 domain-containing protein tyrosine phosphatase-2 (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

SUMMARY OF THE DISCLOSURE

The present disclosure relates to compounds capable of inhibiting the activity of SHP2. The disclosure further provides a process for the preparation of compounds disclosed herein, pharmaceutical preparations comprising such compounds and methods of using such compounds and compositions in the management of diseases or disorders associated with the aberrant activity of SHP2.

One aspect of the disclosure relates to compounds of Formula I:

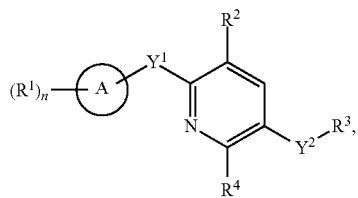

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$ NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is —C₁-C₆alkyl or a 3- to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, or —NH₂;

R⁴ is —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula II:

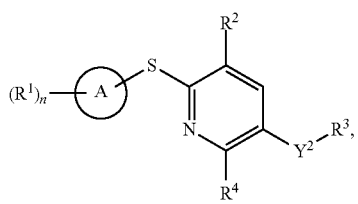

II and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y² is —Rᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyridine ring and the bond on the right side of the Y² moiety is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —ORᵇ, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is —C₁-C₆alkyl or a 3- to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, or —NH₂;

R⁴ is —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula III:

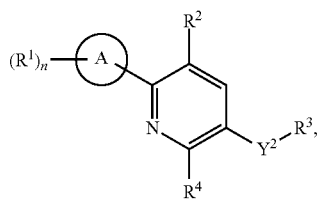

III and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a{}_2)_m$—, —C(O)—, —$C(R^a)_2$NH—, —$(CR^a{}_2)_mO$—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, —C(O)$R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-X:

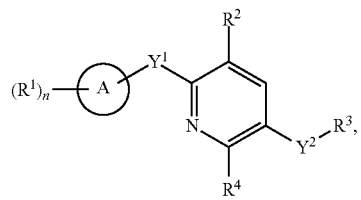

I-X and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is —H, —$C_1$-$C_6$alkyl, or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Y:

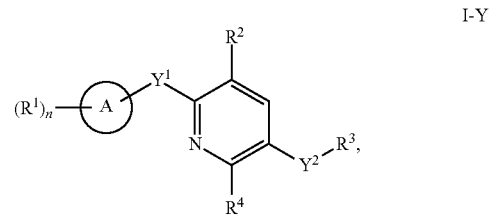

I-Y and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a_2)_m$—, —$C(O)$—, —$C(R^a)_2NH$—, —$(CR^a_2)O$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, or —$OC(O)O$—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Y that are of Formula I-Y1:

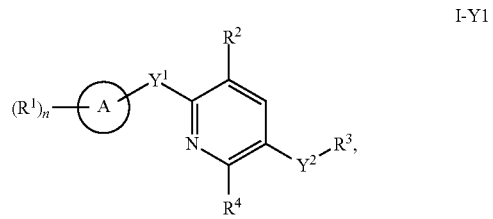

I-Y1 and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^1$ is —S— or a direct bond;

Y$^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyridine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, —NO$_2$, oxo, —CN, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is —OH, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, Oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, Oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is —H, -D, —C$_1$-C$_6$alkyl, —NH—NHR$^5$, —NH—OR$^5$, —O—NR$^5$R$^6$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —OH, —CN, —C(O)NR$^5$R$^6$, —S(O)$_2$NR$^5$R$^6$, C$_3$-C$_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Y that are of Formula I-Y6:

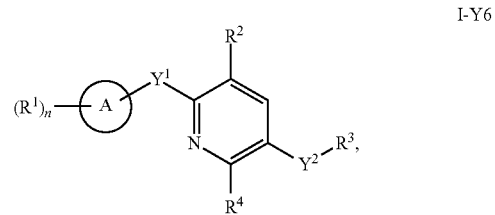

and pharmaceutically acceptable salts, prodrugs, solvates, hydrates, tautomers, or isomers thereof, wherein:

A is a 5- to 12-membered monocyclic or polycyclic aryl or heteroaryl;

Y$^1$ is —S—;

Y$^2$ is —NR$^a$—; wherein the bond on the left side of Y$^2$, as drawn, is bound to the pyridine ring and the bond on the right side of the Y$^2$ moiety, as drawn, is bound to R$^3$;

R$^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, —CF$_3$, —CHF$_2$, or —CH$_2$F;

R$^1$ is independently, at each occurrence, —H, —C$_1$-C$_6$alkyl, —OH, halogen, or —NR$^5$R$^6$;

R$^2$ is —C$_1$-C$_6$alkyl or —OH;

R$^4$ is —H, —C$_1$-C$_6$alkyl, —C$_1$-C$_6$haloalkyl, —C$_1$-C$_6$hydroxyalkyl, —CH$_2$OH, —CF$_2$OH, or —CHFOH, wherein alkyl is optionally substituted with one or more —OH, —NH$_2$, halogen, or oxo; or R$^5$ and R$^6$ are each independently, at each occurrence, —H or —C$_1$-C$_6$alkyl; and n is independently, at each occurrence, 1, 2, 3, 4, 5, 6, 7, 8, 9, or 10.

One aspect of the disclosure relates to compounds of Formula I-Y that are of Formula I-Y7:

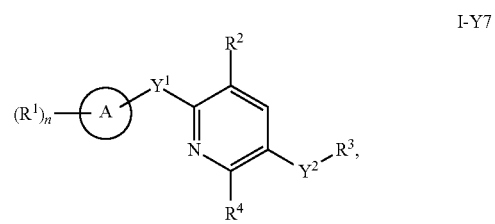

and pharmaceutically acceptable salts, prodrugs, solvates, hydrates, tautomers, or isomers thereof, wherein:

A is a 5- to 12-membered monocyclic or polycyclic aryl or heteroaryl;

Y$^1$ is a direct bond;

Y$^2$ is —NR$^a$—; wherein the bond on the left side of Y$^2$, as drawn, is bound to the pyridine ring and the bond on the right side of the Y$^2$ moiety, as drawn, is bound to R$^3$;

R$^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, —CF$_3$, —CHF$_2$, or —CH$_2$F;

R$^1$ is independently, at each occurrence, —H, —C$_1$-C$_6$alkyl, —OH, halogen, or —NR$^5$R$^6$;

R$^2$ is —C$_1$-C$_6$alkyl or —OH;

R$^4$ is —H, —C$_1$-C$_6$alkyl, —C$_1$-C$_6$haloalkyl, —C$_1$-C$_6$hydroxyalkyl, —CH$_2$OH, —CF$_2$OH, or —CHFOH, wherein alkyl is optionally substituted with one or more —OH, —NH$_2$, halogen, or oxo; or R$^5$ and R$^6$ are each independently, at each occurrence, —H or —C$_1$-C$_6$alkyl; and n is independently, at each occurrence, 1, 2, 3, 4, 5, 6, 7, 8, 9, or 10.

One aspect of the disclosure relates to compounds of Formula I-Z:

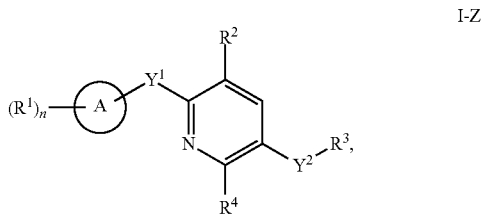

I-Z and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^1$ is —S—, a direct bond, —NH—, —S(O)$_2$—, —S(O)$_2$—NH—, —C(=CH$_2$)—, —CH—, or —S(O)—;

Y$^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyridine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is —OR$^b$, —CN, —C$_1$-C$_6$alkyl, —C$_2$-C$_6$alkenyl, —C$_4$-C$_8$cycloalkenyl, —C$_2$-C$_6$alkynyl, —NH$_2$, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to methods of treating a disease associated with SHP2 modulation in a subject in need thereof, comprising administering to the subject an effective amount of one or more compounds disclosed herein (e.g., compounds of Formula I, II, III, I-X, I-Y, or I-Z, and pharmaceutically acceptable salts, prodrugs, solvates, hydrates, tautomers, or isomers thereof).

Another aspect of the disclosure relates to methods of inhibiting SHP2. The method comprises administering to a patient in need thereof, an effective amount of one or more compounds disclosed herein (e.g., compounds of Formula I, II, III, I-X, I-Y, or I-Z, and pharmaceutically acceptable salts, prodrugs, solvates, hydrates, tautomers, or isomers thereof).

Another aspect of the disclosure is directed to pharmaceutical compositions comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof) and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the disclosure relates to methods of treating a disease associated with SHP2 modulation in a subject in need thereof, comprising administering to the subject an effective amount of a pharmaceutical composition comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof).

Another aspect of the disclosure relates to methods of inhibiting SHP2 comprising administering to a patient in need thereof, an effective amount of a pharmaceutical composition comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof).

Another aspect of the disclosure relates to one or more compounds disclosed herein (e.g., compounds of Formula I, II, III, I-X, I-Y, or I-Z, and pharmaceutically acceptable salts, prodrugs, solvates, hydrates, tautomers, or isomers thereof), for use in treating or preventing a disease associated with SHP2 modulation. One aspect of the disclosure relates to pharmaceutical compositions comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof), and a pharmaceutically acceptable carrier, for use in treating of preventing a disease associated with SHP2 modulation.

Another aspect of the disclosure relates to the use of one or more compounds disclosed herein (e.g., compounds of Formula I, II, III, I-X, I-Y, or I-Z, and pharmaceutically acceptable salts, prodrugs, solvates, hydrates, tautomers, or isomers thereof), in the manufacture of a medicament for treating or preventing a disease associated with SHP2 modulation. Another aspect of the disclosure relates to the use of pharmaceutical compositions comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof), and a pharmaceutically acceptable carrier, in the manufacture of a medicament for treating or preventing a disease associated with SHP2 modulation.

Another aspect of the disclosure relates to one or more compounds disclosed herein (e.g., compounds of Formula I, II, III, I-X, I-Y, or I-Z, and pharmaceutically acceptable salts, prodrugs, solvates, hydrates, tautomers, or isomers thereof), for use as a medicament. Another aspect of the disclosure relates to pharmaceutical compositions comprising one or more compounds disclosed herein (e.g., compounds of Formula I, II, III, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

The present disclosure also provides compounds and pharmaceutical compositions that are useful in inhibiting SHP2.

DETAILED DESCRIPTION OF THE DISCLOSURE

In a first aspect, compounds of Formula I are described:

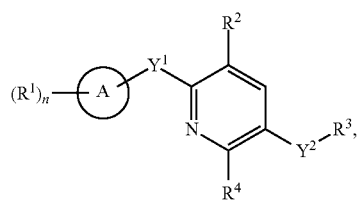

and pharmaceutically acceptable salts, prodrugs, solvates, hydrates, tautomers, or isomers thereof, wherein A, $R^1$, $R^2$, $R^3$, $R^4$, $Y^1$, $Y^2$, and n are described as above.

In another aspect, compounds of the Formula II are described:

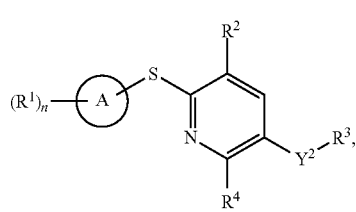

and pharmaceutically acceptable salts, prodrugs, solvates, hydrates, tautomers, or isomers thereof, wherein A, $R^1$, $R^2$, $R^3$, $R^4$, $Y^2$, and n are described as above.

In another aspect, compounds of the Formula III are described:

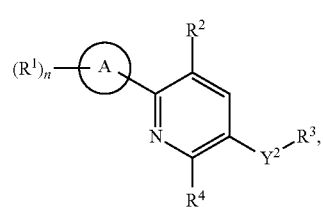

and pharmaceutically acceptable salts, prodrugs, solvates, hydrates, tautomers, or isomers thereof, wherein A, $R^1$, $R^2$, $R^3$, $R^4$, $Y^2$, and n are described as above.

One aspect of the disclosure relates to compounds of Formula I-X:

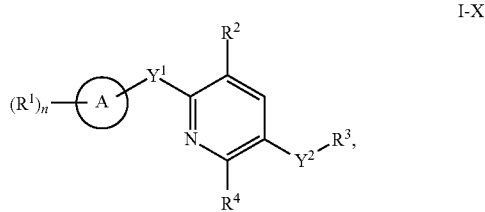

I-X and pharmaceutically acceptable salts, prodrugs, solvates, hydrates, tautomers, or isomers thereof, wherein A, $R^1$, $R^2$, $R^3$, $R^4$, $Y^2$, and n are described as above.

One aspect of the disclosure relates to compounds of Formula I-Y:

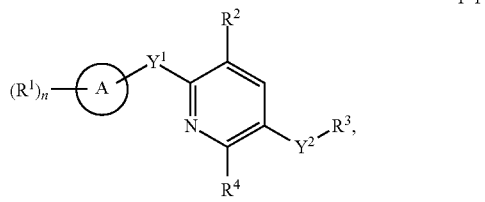

I-Y and pharmaceutically acceptable salts, prodrugs, solvates, hydrates, tautomers, or isomers thereof, wherein A, $R^1$, $R^2$, $R^3$, $R^4$, $Y^2$, and n are described as above.

One aspect of the disclosure relates to compounds of Formula I-Z:

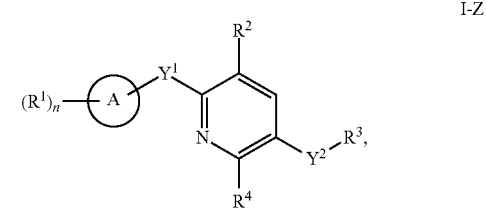

I-Z and pharmaceutically acceptable salts, prodrugs, solvates, hydrates, tautomers, or isomers thereof, wherein A, $R^1$, $R^2$, $R^3$, $R^4$, $Y^2$, and n are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

General Information

The articles "a" and "an" are used in this disclosure and may refer to one or more than one (i.e., to at least one) of the grammatical object of the article. By way of example, "an element" may mean one element or more than one element.

The term "and/or" is used in this disclosure to possibly mean either "and" or "or" unless indicated otherwise.

As used herein, "optional" or "optionally" may mean that the subsequently described event or circumstance may or may not occur, and that the description includes instances where the event or circumstance occurs and instances in which it does not. For example, "optionally substituted aryl" may encompass both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" is understood to possibly mean that a given chemical moiety (e.g. an alkyl group) can (but is not required to) be bonded other substituents (e.g. heteroatoms). For instance, an alkyl group that is optionally substituted may be a fully saturated alkyl chain (i.e. a pure hydrocarbon). Alternatively, the same optionally substituted alkyl group may have substituents different from hydrogen. For instance, it can, at any point along the chain be bonded to a halogen atom, a hydroxyl group, or any other substituent described herein. Thus the term "optionally substituted" may mean that a given chemical moiety has the potential to contain other functional groups, but does not necessarily have any further functional groups.

The term "aryl" may refer to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted.

Unless otherwise specifically defined, "heteroaryl" may mean a monovalent or multivalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also may mean a bicyclic heteroaromatic group wherein the heteroatom is selected from N, S, P, and O. The term may also include multiple condensed ring systems that have at least one such aromatic ring, which multiple condensed ring systems are further described below. The term may also include multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1, 2, 3, 4-tetrahydro-1,8-naphthyridinyl), carbocycles (to form for example 5,6,7,8-tetrahydroquinolyl) and aryls (to form for example indazolyl) to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). The aromatic radical may be optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, benzo[d]imidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, 1-methyl-1H-indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, isoindolin-1-one, indolin-2-one, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, 2-methylbenzo[d]oxazolyl, 1,2,3,4-tetrahydropyrrolo[1,2-a]pyrimidyl, 2,3-dihydrobenzofuranyl, benzooxazolyl, benzoisoxazolyl, benzo[d]isoxazolyl, benzo[d]oxazolyl, furo[2,3-b]pyridinyl, benzothiophenyl, 1,5-naphthyridinyl, furo[3,2-b]pyridinyl, [1,2,4]triazolo[1,5-a]pyridinyl, benzo[1,2,3]triazolyl, 1-methyl-1H-benzo[d][1,2,3]triazolyl, imidazo[1,2-a]pyrimidinyl, [1,2,4]triazolo[4,3-b]pyridazinyl, quinoxalinyl, benzo[c][1,2,5]thiadiazolyl, benzo[c][1,2,5]oxadiazolyl, 1,3-dihydro-2H-benzo[d]imidazol-2-one, 3,4-dihydro-2H-pyrazolo[1,5-b][1,2]oxazinyl, 3,4-dihydro-2H-benzo[b][1,4]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, benzo[d][1,3]dioxolyl, pyrazolo[1,5-a]pyridinyl, and derivatives of any of the foregoing.

"Alkyl" may refer to a straight or branched chain saturated hydrocarbon. $C_1$-$C_6$alkyl groups contain 1 to 6 carbon atoms. Examples of a $C_1$-$C_6$alkyl group may include, but are not limited to, methyl, ethyl, propyl, butyl, pentyl, isopropyl, isobutyl, sec-butyl and tert-butyl, isopentyl and neopentyl.

The term "alkenyl" may mean an aliphatic hydrocarbon group containing a carbon-carbon double bond and which may be straight or branched having about 2 to about 6 carbon atoms in the chain. Certain alkenyl groups may have about 2 to about 4 carbon atoms in the chain. Branched may mean that one or more lower alkyl groups such as methyl, ethyl, or propyl are attached to a linear alkenyl chain. Exemplary alkenyl groups include, but are not limited to, ethenyl, propenyl, n-butenyl, and i-butenyl. A $C_2$-$C_6$ alkenyl group is an alkenyl group containing between 2 and 6 carbon atoms.

The term "alkynyl" may mean an aliphatic hydrocarbon group containing a carbon-carbon triple bond and which may be straight or branched having about 2 to about 6 carbon atoms in the chain. Certain alkynyl groups may have about 2 to about 4 carbon atoms in the chain. Branched may mean that one or more lower alkyl groups such as methyl, ethyl, or propyl are attached to a linear alkynyl chain. Exemplary alkynyl groups may include, but are not limited to, ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" may mean monocyclic or polycyclic saturated carbon rings containing 3-18 carbon atoms. Examples of cycloalkyl groups may include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group may be fused (e.g., decalin) or bridged (e.g., norbornane).

The term "cycloalkenyl" may mean monocyclic, non-aromatic unsaturated carbon rings containing 4-18 carbon atoms. Examples of cycloalkenyl groups may include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

In some embodiments, the terms "heterocyclyl" or "heterocycloalkyl" or "heterocycle" may refer to monocyclic or polycyclic 3 to 24-membered rings containing carbon and heteroatoms selected from oxygen, phosphorus, nitrogen, and sulfur and wherein there are no delocalized π electrons (aromaticity) shared among the ring carbon or heteroatoms. Heterocyclyl rings may include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring may also be fused or bridged, e.g., can be a bicyclic ring.

In some embodiments "heterocyclyl" or "heterocycloalkyl" or "heterocycle" may be a saturated, partially saturated or unsaturated, mono or bicyclic ring containing 3-24 atoms of which at least one atom is chosen from nitrogen, sulfur or oxygen, which may, unless otherwise specified, be carbon or nitrogen linked, wherein a —CH$_2$— group can optionally be replaced by a —C(O)— or a ring sulfur atom may be optionally oxidised to form the S-oxides. "Heterocyclyl" may be a saturated, partially saturated or unsaturated, mono or bicyclic ring containing 5 or 6 atoms of which at least one atom is chosen from nitrogen, sulfur or oxygen, which may, unless otherwise specified, be carbon or nitrogen linked, wherein a —CH$_2$— group can optionally be replaced by a —C(O)— or a ring sulfur atom may be optionally oxidised to form S-oxide(s). Non-limiting examples and suitable values of the term "heterocyclyl" may include thiazolidinyl, pyrrolidinyl, pyrrolinyl, 2-pyrrolidonyl, 2,5-dioxopyrrolidinyl, 2-benzoxazolinonyl, 1,1-dioxotetrahydro thienyl, 2,4-dioxoimidazolidinyl, 2-oxo-1,3,4-(4-triazolinyl), 2-oxazolidinonyl, 5,6-dihydro uracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

As used herein, the term "halo" or "halogen" may mean a fluoro, chloro, bromo, or iodo group.

The term "carbonyl" may refer to a functional group comprising a carbon atom double-bonded to an oxygen atom. It can be abbreviated herein as "oxo," as C(O), or as C=O.

"Spirocycle" or "spirocyclic" may mean carbogenic bicyclic ring systems with both rings connected through a single atom. The ring can be different in size and nature, or identical in size and nature. Examples may include, but are not limited to, spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. One or more of the carbon atoms can be substituted with a heteroatom.

The term "spirocyclic heterocycle," "spiroheterocyclyl," or "spiroheterocycle" is understood to possibly mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of one or more disclosed compounds and a pharmaceutically acceptable carrier. As used herein "pharmaceutically acceptable carrier, diluent or excipient" may include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The disclosure may include pharmaceutically acceptable salts of the compounds disclosed herein. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, glucepatate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" also includes both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The term "tautomers" may refer to a set of compounds that have the same number and type of atoms, but differ in bond connectivity and are in equilibrium with one another. A "tautomer" is a single member of this set of compounds. Typically a single tautomer is drawn but it may be understood that this single structure may represent all possible tautomers that might exist. Examples include enol-ketone tautomerism. When a ketone is drawn it may be understood that both the enol and ketone forms are part of the disclosure.

The disclosure may include prodrugs of the compounds described herein. The term "prodrug," as used in this disclosure, may mean a compound which is convertible in vivo by metabolic means (e.g., by hydrolysis) to a disclosed compound. Furthermore, as used herein a prodrug may be a drug which is inactive in the body, but may be transformed in the body typically either during absorption or after absorption from the gastrointestinal tract into the active compound. The conversion of the prodrug into the active compound in the body may be done chemically or biologically (i.e., using an enzyme).

The disclosure may include solvates of the compounds described herein. The term "solvate" may refer to a complex of variable stoichiometry formed by a solute and solvent. Such solvents for the purpose of the disclosure may not interfere with the biological activity of the solute. Examples of suitable solvents may include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

The disclosure may include isomers of the compounds described herein. The term "isomer" may refer to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present disclosure may have one or more asymmetric carbon atom and may occur as racemates, racemic mixtures and as individual enantiomers or diastereomers.

The disclosure may include stereoisomers of the compounds described herein. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer.

In addition, the present disclosure may embrace all geometric and positional isomers. For example, if a compound of the present disclosure incorporates a double bond or a fused ring, both the cis- and trans-forms, as well as mixtures, are embraced within the scope of the disclosure. If the compound contains a double bond, the substituent may be in the E or Z configuration. If the compound contains a disubstituted cycloalkyl, the cycloalkyl substituent may have a cis or trans configuration.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. The disclosure may include enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds may be the (S)-enantiomer. In other embodiments the compounds may be the (R)-enantiomer. In yet other embodiments, the compounds may be the (+) or (−) enantiomers.

In some embodiments, compounds and compositions of the disclosure may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2 mol percent of the second enantiomer.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, the compounds and compositions of the disclosure may be enriched to provide predominantly one diastereomer of a compound disclosed herein. A diastereomerically enriched mixture may comprise, for example, at least 60 mol percent of one diastereomer, or more preferably at least 75, 99, 95, 96, 97, 98, 99, or even 100 mol percent.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3$H, and carbon 14, i.e., $^{14}$C, may be particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. Substitution with positron emitting isotopes, such as $^{11}$C, $^{18}$F, $^{15}$O, and $^{13}$N, can be useful in Positron Emission Topography (PET) studies.

An "effective amount" when used in connection with a compound may be an amount effective for treating or preventing a disease in a subject as described herein.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, may refer to improving at least one symptom of the subject's disorder. Treating may include curing, improving, or at least partially ameliorating the disorder.

The term "prevent" or "preventing" with regard to a subject may refer to keeping a disease or disorder from afflicting the subject. Preventing may include prophylactic treatment. For instance, preventing can include administering to the subject one or more compounds disclosed herein before a subject is afflicted with a disease and the administration will keep the subject from being afflicted with the disease.

The term "disorder" is used in this disclosure and may be used interchangeably with, the terms disease, condition, or illness, unless otherwise indicated.

The term "administer," "administering," or "administration" as used in this disclosure may refer to either directly administering one or more disclosed compounds or a pharmaceutically acceptable salt of the one or more disclosed compounds or a composition comprising one or more disclosed compounds to a subject, or administering a prodrug derivative or analog of the one or more disclosed compounds or pharmaceutically acceptable salts of the one or more disclosed compounds or compositions to the subject, which may form an equivalent amount of active compound within the subject's body.

A "patient" or "subject" may be a mammal, e.g., a human, mouse, rat, guinea pig, dog, cat, horse, cow, pig, or non-human primate, such as a monkey, chimpanzee, baboon or rhesus.

Compounds of the Disclosure

Compounds of the disclosure include compounds of Formula I, II, III, I-X, I-Y, or I-Z, and pharmaceutically acceptable salts, prodrugs, solvates, hydrates, tautomers, or isomers of any of the foregoing.

In one or more embodiments of the compounds of Formula I, the compound is of the Formula I-A:

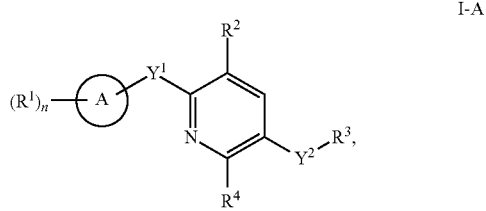

I-A and pharmaceutically acceptable salts, prodrugs, solvates, hydrates, tautomers, or isomers thereof, wherein:

A is aryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula I, the compound is of the Formula I-B:

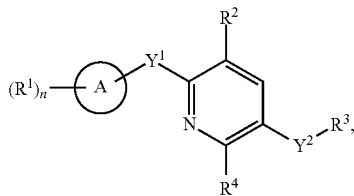

and pharmaceutically acceptable salts, prodrugs, solvates, hydrates, tautomers, or isomers thereof, wherein:

A is heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula I, the compound is of the Formula I-C:

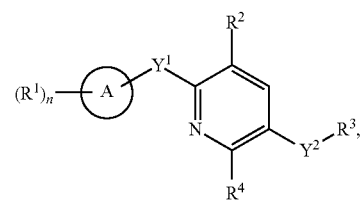

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, —NO$_2$, oxo, —CN, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is —OH, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^3$ is —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is —H, -D, or —C$_1$-C$_6$alkyl, wherein each alkyl is optionally substituted with one or more —OH, —NH$_2$, halogen, or oxo; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula I-C, R$^4$ is —C$_1$-C$_6$alkyl, which is optionally substituted with one or more —OH, —NH$_2$, halogen, or oxo. In one or more embodiments of Formula I-C, R$^4$ is —C$_1$-C$_6$alkyl, which is substituted with one or more —OH. In certain such embodiments, R$^4$ is —CH$_2$—OH. In one or more embodiments of Formula I-C, R$^4$ is —H. In one or more embodiments of Formula I-C, R$^4$ is —C$_1$-C$_6$haloalkyl or —C$_1$-C$_6$hydroxyalkyl. In one or more embodiments of Formula I-C, R$^4$ is —CF$_2$OH or —CHFOH.

In one or more embodiments of the compounds of Formula I-C, Y$^2$ is —(CR$^{a2}$)$_m$—. In one or more embodiments of the compounds of Formula I-C, Y$^2$ is —NR$^a$—. In one or more embodiments of the compounds of Formula I-C, Y$^1$ is —S—. In one or more embodiments of the compounds of Formula I-C, Y$^1$ is a direct bond.

In one or more embodiments of Formula I-C, A is a monocyclic or polycyclic cycloalkyl. In one or more embodiments of Formula I-C, A is a monocyclic or polycyclic heterocycloalkyl. In one or more embodiments of Formula I-C, A is monocyclic or polycyclic aryl. In one or more embodiments of Formula I-C, A is phenyl. In one or more embodiments of Formula I-C, A is monocyclic or polycyclic heteroaryl. In one or more embodiments of Formula I-C, A is pyridinyl.

In one or more embodiments of Formula I-C, n is independently, at each occurrence, 0, 1, 2, or 3. In one or more embodiments of Formula I-C, n is independently, at each occurrence, 1 or 2.

In one or more embodiments of Formula I-C, R$^1$ is independently, at each occurrence, —H, halogen or —NR$^5$R$^6$. In certain such embodiments, R$^5$ and R$^6$ are both —H. In one or more embodiments of Formula I-C, R$^1$ is independently, at each occurrence, —H, methyl, fluoro, chloro, or —NH$_2$.

In one or more embodiments of Formula I-C, R$^2$ is —OH. In one or more embodiments of Formula I-C, R$^2$ is an optionally substituted —C$_1$-C$_6$alkyl. In certain such embodiments, R$^2$ is methyl.

In one or more embodiments of Formula I-C, R$^a$ is —H.

In one or more embodiments of Formula I-C, R$^3$ is an optionally substituted —C$_1$-C$_6$alkyl. In one or more embodiments of Formula I-C, R$^3$ is an optionally substituted 3- to 12-membered monocyclic or polycyclic heterocycle. In one or more embodiments of Formula I-C, R$^3$ is an optionally substituted 3- to 12-membered monocyclic heterocycle. In one or more embodiments of Formula I-C, R$^3$ is an optionally substituted 5- to 12-membered polycyclic heterocycle.

In one or more embodiments of Formula I-C, R$^3$ and R$^a$ together with the atom to which they are attached combine to form a 3- to 12-membered monocyclic heterocycle, which is optionally substituted with one or more —C$_1$-C$_6$alkyl, —OH, or —NH$_2$. In one or more embodiments of Formula I-C, R$^3$ and R$^a$ together with the atom to which they are attached combine to form a 3- to 12-membered monocyclic heterocycle, which is optionally substituted with one or more —C$_1$-C$_6$alkyl or —NH$_2$.

In one or more embodiments of Formula I-C, R$^3$ and R$^a$ together with the atoms to which they are attached combine to form a 3- to 12-membered polycyclic heterocycle, which is optionally substituted with one or more —C$_1$-C$_6$alkyl, —NH$_2$, or —OH. In one or more embodiments of Formula I-C, R$^3$ and R$^a$ together with the atom to which they are attached combine to form a 3- to 12-membered polycyclic heterocycle, which is optionally substituted with one or more —C$_1$-C$_6$alkyl or —NH$_2$.

In one or more embodiments of Formula I-C, R$^3$ and R$^a$ together with the atoms to which they are attached combine to form a 5- to 12-membered spiroheterocycle, which is optionally substituted with one or more —C$_1$-C$_6$alkyl, —NH$_2$, or —OH. In one or more embodiments of Formula I-C, R$^3$ and R$^a$ together with the atoms to which they are attached combine to form a 5- to 12-membered spiroheterocycle, which is optionally substituted with one or more —$C_1$-$C_6$alkyl or —$NH_2$.

In one or more embodiments of Formula I-C, $R^3$ and $R^a$ together with the atoms to which they are attached combine to form a 10- to 12-membered spiroheterocycle, which is optionally substituted with one or more —$C_1$-$C_6$alkyl, —$NH_2$, or —OH. In one or more embodiments of Formula I-C, $R^3$ and $R^a$ together with the atoms to which they are attached combine to form a 10- to 12-membered spiroheterocycle, which is optionally substituted with one or more —$C_1$-$C_6$alkyl or —$NH_2$.

In one or more embodiments of the compounds of Formula II, the compound is of the Formula II-A:

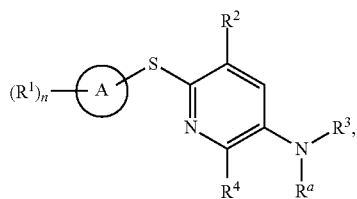

II-A and pharmaceutically acceptable salts, prodrugs, solvates, hydrates, tautomers, or isomers thereof.

In one or more embodiments of the compounds of the Formula II-A, the compound is of the Formula II-A1:

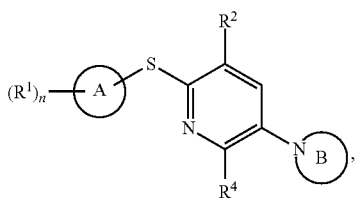

II-A1 and pharmaceutically acceptable salts, prodrugs, solvates, hydrates, tautomers, or isomers thereof, wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, or —$NH_2$.

In one or more embodiments of the compounds of Formula II-A, the compound is of the Formula II-A2:

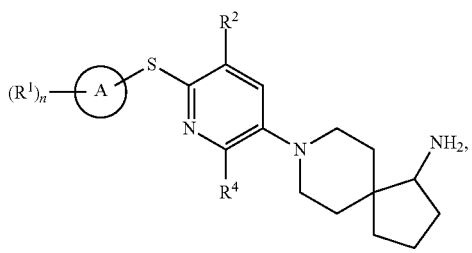

II-A2 and pharmaceutically acceptable salts, prodrugs, solvates, hydrates, tautomers, or isomers thereof.

In one or more embodiments of the compounds of Formula II-A, the compound is of the Formula II-A3:

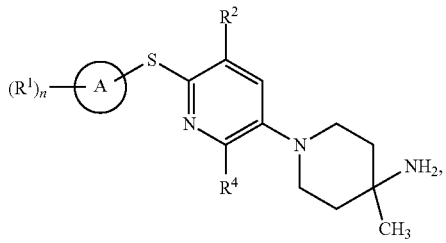

II-A3 and pharmaceutically acceptable salts, prodrugs, solvates, hydrates, tautomers, or isomers thereof.

In one or more embodiments of the compounds of Formula II, the compound is of the Formula II-B:

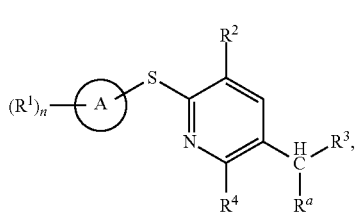

II-B and pharmaceutically acceptable salts, prodrugs, solvates, hydrates, tautomers, or isomers thereof.

In one or more embodiments of the compounds of Formula II-B, the compound is of the Formula II-B1:

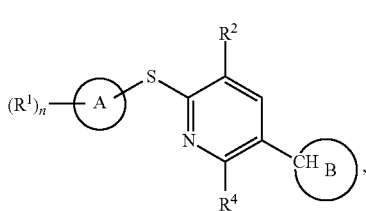

II-B1 and pharmaceutically acceptable salts, prodrugs, solvates, hydrates, tautomers, or isomers thereof, wherein:

B forms a 3- to 12-membered monocyclic or polycyclic heterocycle or a 5- to 12-membered spiroheterocycle along with the carbon atom to which it is attached, wherein the heterocycle or spiroheterocycle is optionally substituted with one or more —$C_1$-$C_6$alkyl, —OH, or —$NH_2$.

In one or more embodiments of the compounds of Formula II-B, the compound is of the Formula II-B2:

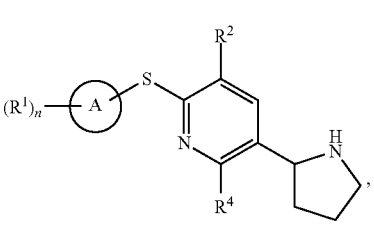

II-B2 and pharmaceutically acceptable salts, prodrugs, solvates, hydrates, tautomers, or isomers thereof.

In one or more embodiments of the compounds of Formula II-B, the compound is of the Formula II-B3:

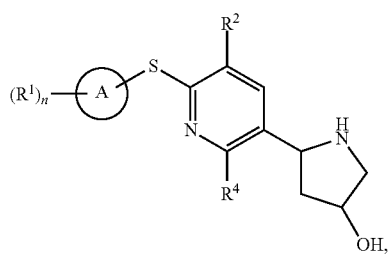

II-B3 and pharmaceutically acceptable salts, prodrugs, solvates, hydrates, tautomers, or isomers thereof.

In one or more embodiments of the compounds of Formula II-B, the compound is of the Formula II-B4:

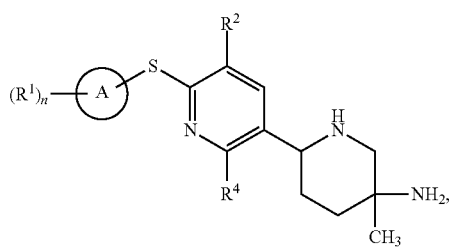

II-B4 and pharmaceutically acceptable salts, prodrugs, solvates, hydrates, tautomers, or isomers thereof.

In one or more embodiments of the compounds of Formula II-B, the compound is of the Formula II-B5:

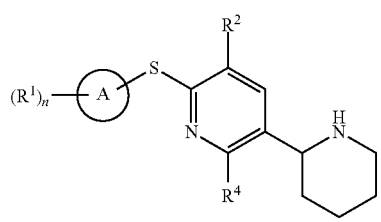

II-B5 and pharmaceutically acceptable salts, prodrugs, solvates, hydrates, tautomers, or isomers thereof.

In one or more embodiments of the compounds of Formula II-B, the compound is of the Formula II-B6:

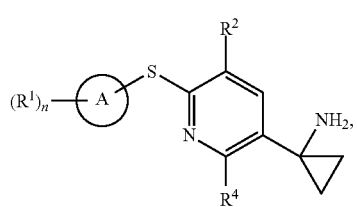

II-B6 and pharmaceutically acceptable salts, prodrugs, solvates, hydrates, tautomers, or isomers thereof.

In one or more embodiments of the compounds of Formula II, the compound is of the Formula II-C:

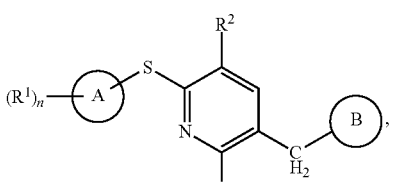

II-C and pharmaceutically acceptable salts, prodrugs, solvates, hydrates, tautomers, or isomers thereof, wherein:

B forms a 3- to 12-membered monocyclic or polycyclic heterocycle, wherein the heterocycle or spiroheterocycle is optionally substituted with one or more —$C_1$-$C_6$alkyl, —OH, or —$NH_2$ In one or more embodiments of the compounds of Formula II-C, the compound is of the Formula II-C1:

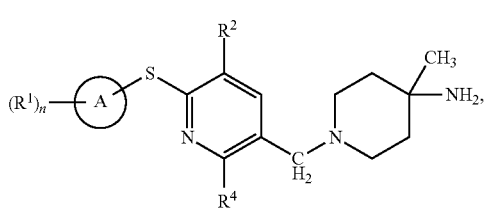

II-C1 and pharmaceutically acceptable salts, prodrugs, solvates, hydrates, tautomers, or isomers thereof.

In one or more embodiments of the compounds of Formula II, the compound is of the Formula II-D:

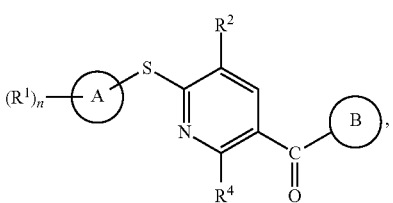

II-D and pharmaceutically acceptable salts, prodrugs, solvates, hydrates, tautomers, or isomers thereof, wherein:

B forms a 3- to 12-membered monocyclic or polycyclic heterocycle, wherein the heterocycle or spiroheterocycle is optionally substituted with one or more —$C_1$-$C_6$alkyl, —OH, or —$NH_2$.

In one or more embodiments of the compounds of Formula II-D, the compound is of the Formula II-D1:

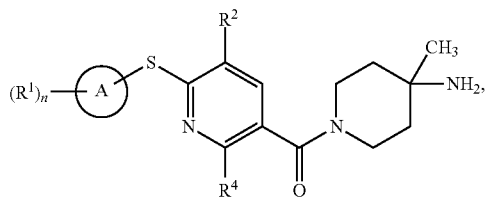

and pharmaceutically acceptable salts, prodrugs, solvates, hydrates, tautomers, or isomers thereof.

In one or more embodiments of the compounds of Formula II, the compound is of the Formula II-E:

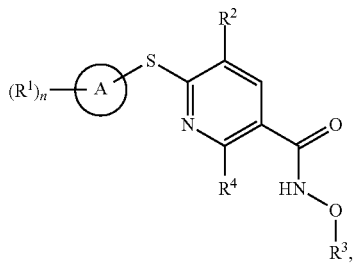

and pharmaceutically acceptable salts, prodrugs, solvates, hydrates, tautomers, or isomers thereof.

In one or more embodiments of the compounds of Formula II, the compound is of the Formula II-F:

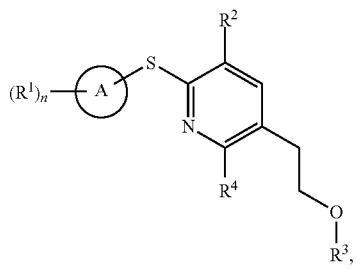

and pharmaceutically acceptable salts, prodrugs, solvates, hydrates, tautomers, or isomers thereof.

In one or more embodiments of the compounds of Formula II, the compound is of the Formula II-G:

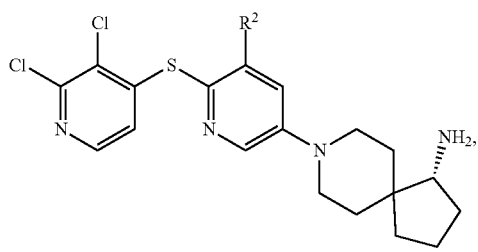

and pharmaceutically acceptable salts, prodrugs, solvates, hydrates, tautomers, or isomers thereof, wherein $R^2$ is an aryl or heteroaryl.

In one or more embodiments of the compounds of Formula II, the compound is of the Formula II-H:

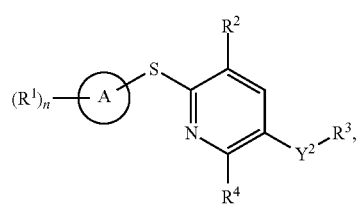

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, —$NO_2$, oxo, —CN, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —OH, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, Oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula II-H, $R^4$ is —$C_1$-$C_6$alkyl, which is optionally substituted with one or more —OH, —$NH_2$, halogen, or oxo. In one or more embodiments of Formula II-H, $R^4$ is —$C_1$-$C_6$alkyl, which is substituted with one or more —OH. In certain such embodiments, $R^4$ is —$CH_2$—OH. In one or more embodiments of Formula II-H, $R^4$ is —H. In one or more embodiments of Formula II-H, $R^4$ is —$C_1$-$C_6$haloalkyl or —$C_1$-$C_6$hydroxyalkyl. In one or more embodiments of Formula II-H, $R^4$ is —$CF_2$OH or —CHFOH.

In one or more embodiments of the compounds of Formula II-H, $Y^2$ is —$(CR^a{}_2)_m$—. In one or more embodiments of the compounds of Formula II-H, $Y^2$ is —$NR^a$—.

In one or more embodiments of Formula II-H, A is a monocyclic or polycyclic cycloalkyl. In one or more embodiments of Formula II-H, A is a monocyclic or polycyclic heterocycloalkyl. In one or more embodiments of Formula II-H, A is monocyclic or polycyclic aryl. In one or more embodiments of Formula II-H, A is phenyl. In one or more embodiments of Formula II-H, A is monocyclic or polycyclic heteroaryl. In one or more embodiments of Formula II-H, A is pyridinyl.

In one or more embodiments of Formula II-H, n is independently, at each occurrence, 0, 1, 2, or 3. In one or more embodiments of Formula II-H, n is independently, at each occurrence, 1 or 2.

In one or more embodiments of Formula II-H, $R^1$ is independently, at each occurrence, —H, halogen or —$NR^5R^6$. In certain such embodiments, $R^5$ and $R^6$ are both —H. In one or more embodiments of Formula II-H, $R^1$ is independently, at each occurrence, —H, methyl, fluoro, chloro, or —$NH_2$.

In one or more embodiments of Formula II-H, $R^2$ is —OH. In one or more embodiments of Formula II-H, $R^2$ is an optionally substituted —$C_1$-$C_6$alkyl. In certain such embodiments, $R^2$ is methyl.

In one or more embodiments of Formula II-H, $R^a$ is —H.

In one or more embodiments of Formula II-H, $R^3$ is an optionally substituted —$C_1$-$C_6$alkyl. In one or more embodiments of Formula II-H, $R^3$ is an optionally substituted 3- to 12-membered monocyclic or polycyclic heterocycle. In one or more embodiments of Formula II-H, $R^3$ is an optionally substituted 3- to 12-membered monocyclic heterocycle. In one or more embodiments of Formula II-H, $R^3$ is an optionally substituted 5- to 12-membered polycyclic heterocycle.

In one or more embodiments of Formula II-H, $R^3$ and $R^a$ together with the atom to which they are attached combine to form a 3- to 12-membered monocyclic heterocycle, which is optionally substituted with one or more —$C_1$-$C_6$alkyl, —OH, or —$NH_2$. In one or more embodiments of Formula II-H, $R^3$ and $R^a$ together with the atom to which they are attached combine to form a 3- to 12-membered monocyclic heterocycle, which is optionally substituted with one or more —$C_1$-$C_6$alkyl or —$NH_2$.

In one or more embodiments of Formula II-H, $R^3$ and $R^a$ together with the atoms to which they are attached combine to form a 3- to 12-membered polycyclic heterocycle, which is optionally substituted with one or more —$C_1$-$C_6$alkyl, —$NH_2$, or —OH. In one or more embodiments of Formula II-H, $R^3$ and $R^a$ together with the atom to which they are attached combine to form a 3- to 12-membered polycyclic heterocycle, which is optionally substituted with one or more —$C_1$-$C_6$alkyl or —$NH_2$ In one or more embodiments of Formula II-H, $R^3$ and $R^a$ together with the atoms to which they are attached combine to form a 5- to 12-membered spiroheterocycle, which is optionally substituted with one or more —$C_1$-$C_6$alkyl, —$NH_2$, or —OH. In one or more embodiments of Formula II-H, $R^3$ and $R^a$ together with the atoms to which they are attached combine to form a 5- to 12-membered spiroheterocycle, which is optionally substituted with one or more —$C_1$-$C_6$alkyl or —$NH_2$.

In one or more embodiments of Formula II-H, $R^3$ and $R^a$ together with the atoms to which they are attached combine to form a 10- to 12-membered spiroheterocycle, which is optionally substituted with one or more —$C_1$-$C_6$alkyl, —$NH_2$, or —OH. In one or more embodiments of Formula II-H, $R^3$ and $R^a$ together with the atoms to which they are attached combine to form a 10- to 12-membered spiroheterocycle, which is optionally substituted with one or more —$C_1$-$C_6$alkyl or —$NH_2$.

In one or more embodiments of the compounds of Formula III, the compound is of the Formula III-A:

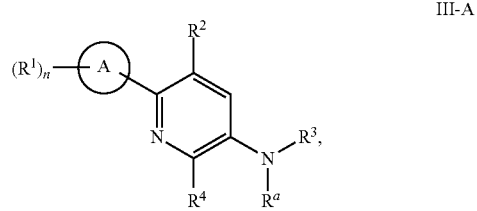

and pharmaceutically acceptable salts, prodrugs, solvates, hydrates, tautomers, or isomers thereof.

In one or more embodiments of the compounds of Formula III-A, the compound is of the Formula III-A1:

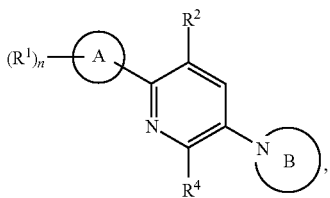

III-A1 and pharmaceutically acceptable salts, prodrugs, solvates, hydrates, tautomers, or isomers thereof, wherein B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, or —$NH_2$.

In one or more embodiments of the compounds of Formula III-A, the compound is of the Formula III-A2:

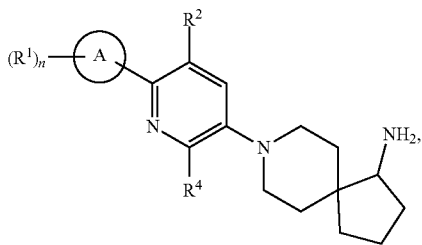

III-A2 and pharmaceutically acceptable salts, prodrugs, solvates, hydrates, tautomers, or isomers thereof.

In one or more embodiments of the compounds of Formula III-A, the compound is of the Formula III-A3:

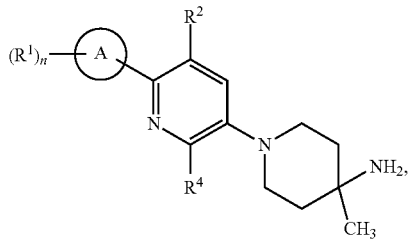

III-A3 and pharmaceutically acceptable salts, prodrugs, solvates, hydrates, tautomers, or isomers thereof.

In one or more embodiments of the compounds of Formula III, the compound is of the Formula III-B:

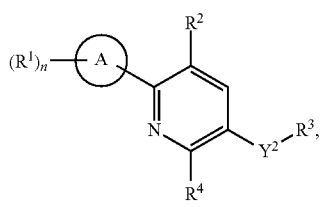

III-B and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, —$NO_2$, oxo, —CN, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —OH, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula III-B, $R^4$ is —$C_1$-$C_6$alkyl, which is optionally substituted with one or more —OH, —$NH_2$, halogen, or oxo. In one or more embodiments of Formula III-B, $R^4$ is —$C_1$-$C_6$alkyl, which is substituted with one or more —OH. In certain such embodiments, $R^4$ is —$CH_2$—OH. In one or more embodiments of Formula III-B, $R^4$ is —H. In one or more embodiments of Formula III-B, $R^4$ is —$C_1$-$C_6$haloalkyl or —$C_1$-$C_6$hydroxyalkyl. In one or more embodiments of Formula III-B, $R^4$ is —$CF_2OH$ or —CHFOH.

In one or more embodiments of the compounds of Formula III-B, $Y^2$ is —$(CR^a{}_2)_m$—. In one or more embodiments of the compounds of Formula III-B, $Y^2$ is —$NR^a$—.

In one or more embodiments of Formula III-B, A is a monocyclic or polycyclic cycloalkyl. In one or more embodiments of Formula III-B, A is a monocyclic or polycyclic heterocycloalkyl. In one or more embodiments of Formula III-B, A is a monocyclic or polycyclic aryl. In one or more embodiments of Formula III-B, A is phenyl. In one or more embodiments of Formula III-B, A is monocyclic or polycyclic heteroaryl. In one or more embodiments of Formula III-B, A is pyridinyl.

In one or more embodiments of Formula III-B, n is independently, at each occurrence, 0, 1, 2, or 3. In one or more embodiments of Formula III-B, n is independently, at each occurrence, 1 or 2.

In one or more embodiments of Formula III-B, $R^1$ is independently, at each occurrence, —H, halogen or —$NR^5R^6$. In certain such embodiments, $R^5$ and $R^6$ are both —H. In one or more embodiments of Formula III-B, $R^1$ is independently, at each occurrence, —H, methyl, fluoro, chloro, or —$NH_2$.

In one or more embodiments of Formula III-B, $R^2$ is —OH. In one or more embodiments of Formula III-B, $R^2$ is an optionally substituted —$C_1$-$C_6$alkyl. In certain such embodiments, $R^2$ is methyl.

In one or more embodiments of Formula III-B, $R^a$ is —H.

In one or more embodiments of Formula III-B, $R^3$ is an optionally substituted —$C_1$-$C_6$alkyl. In one or more embodiments of Formula III-B, $R^3$ is an optionally substituted 3- to 12-membered monocyclic or polycyclic heterocycle. In one or more embodiments of Formula III-B, $R^3$ is an optionally substituted 3- to 12-membered monocyclic heterocycle. In one or more embodiments of Formula III-B, $R^3$ is an optionally substituted 5- to 12-membered polycyclic heterocycle.

In one or more embodiments of Formula III-B, $R^3$ and $R^a$ together with the atom to which they are attached combine to form a 3- to 12-membered monocyclic heterocycle, which is optionally substituted with one or more —$C_1$-$C_6$alkyl, —OH, or —$NH_2$. In one or more embodiments of Formula III-B, $R^3$ and $R^a$ together with the atom to which they are attached combine to form a 3- to 12-membered monocyclic heterocycle, which is optionally substituted with one or more —$C_1$-$C_6$alkyl or —$NH_2$.

In one or more embodiments of Formula III-B, $R^3$ and $R^a$ together with the atoms to which they are attached combine to form a 3- to 12-membered polycyclic heterocycle, which is optionally substituted with one or more —$C_1$-$C_6$alkyl, —$NH_2$, or —OH. In one or more embodiments of Formula III-B, $R^3$ and $R^a$ together with the atom to which they are attached combine to form a 3- to 12-membered polycyclic heterocycle, which is optionally substituted with one or more —$C_1$-$C_6$alkyl or —$NH_2$.

In one or more embodiments of Formula III-B, $R^3$ and $R^a$ together with the atoms to which they are attached combine to form a 5- to 12-membered spiroheterocycle, which is optionally substituted with one or more —$C_1$-$C_6$alkyl, —$NH_2$, or —OH. In one or more embodiments of Formula III-B, $R^3$ and $R^a$ together with the atoms to which they are attached combine to form a 5- to 12-membered spiroheterocycle, which is optionally substituted with one or more —$C_1$-$C_6$alkyl or —$NH_2$.

In one or more embodiments of Formula III-B, $R^3$ and $R^a$ together with the atoms to which they are attached combine to form a 10- to 12-membered spiroheterocycle, which is optionally substituted with one or more —$C_1$-$C_6$alkyl, —$NH_2$, or —OH. In one or more embodiments of Formula III-B, $R^3$ and $R^a$ together with the atoms to which they are attached combine to form a 10- to 12-membered spiroheterocycle, which is optionally substituted with one or more —$C_1$-$C_6$alkyl or —$NH_2$.

In one or more embodiments of the compounds of Formula I-X, the compound is of the Formula I-X1:

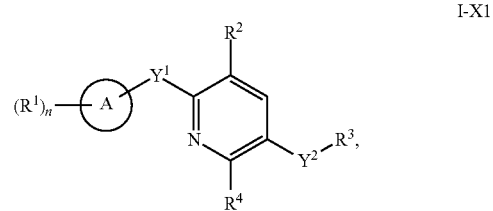

I-X1 and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N(R^a)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, —$NO_2$, oxo, —CN, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —OH, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^3$ is —H, —$C_1$-$C_6$alkyl, or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, —$C_1$-$C_6$alkyl, —NH—$NHR^5$, —NH—$OR^5$, —O—$NR^5R^6$, —$NHC(O)R^5$, —$NHC(O)NHR^5$, —$NHS(O)_2R^5$, —$NHS(O)_2NHR^5$, —$S(O)_2OH$, —$C(O)OR^5$, —$C(O)NR^5R^6$, —$S(O)_2NR^5R^6$, $C_3$-$C_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula I-X1, $R^4$ is —$C_1$-$C_6$alkyl, which is optionally substituted with one or more —OH, —$NH_2$, halogen, or oxo. In one or more embodiments of Formula I-X1, $R^4$ is —$C_1$-$C_6$alkyl, which is substituted with one or more —OH. In certain such embodiments, $R^4$ is —$CH_2$—OH. In one or more embodiments of Formula I-X1, $R^4$ is —H. In one or more embodiments of Formula I-X1, $R^4$ is —$C_1$-$C_6$haloalkyl or —$C_1$-$C_6$hydroxyalkyl. In one or more embodiments of Formula I-X1, $R^4$ is —$CF_2OH$ or —CHFOH.

In one or more embodiments of the compounds of Formula I-X1, $Y^2$ is —$(CR^a_2)_m$—. In one or more embodiments of the compounds of Formula I-X1, $Y^2$ is —$NR^a$—. In one or more embodiments of the compounds of Formula I-X1, $Y^1$ is —S—. In one or more embodiments of the compounds of Formula I-X1, $Y^1$ is a direct bond.

In one or more embodiments of Formula I-X1, A is a monocyclic or polycyclic cycloalkyl. In one or more embodiments of Formula I-X1, A is a monocyclic or polycyclic heterocycloalkyl. In one or more embodiments of Formula I-X1, A is monocyclic or polycyclic aryl. In one or more embodiments of Formula I-X1, A is phenyl. In one or more embodiments of Formula I-X1, A is monocyclic or polycyclic heteroaryl. In one or more embodiments of Formula I-X1, A is pyridinyl.

In one or more embodiments of Formula I-X1, n is independently, at each occurrence, 0, 1, 2, or 3. In one or more embodiments of Formula I-X1, n is independently, at each occurrence, 1 or 2.

In one or more embodiments of Formula I-X1, $R^1$ is independently, at each occurrence, —H, halogen or —$NR^5R^6$. In certain such embodiments, $R^5$ and $R^6$ are both —H. In one or more embodiments of Formula I-X1, $R^1$ is independently, at each occurrence, —H, methyl, fluoro, chloro, or —$NH_2$.

In one or more embodiments of Formula I-X1, $R^2$ is —OH. In one or more embodiments of Formula I-X1, $R^2$ is an optionally substituted —$C_1$-$C_6$alkyl. In certain such embodiments, $R^2$ is methyl.

In one or more embodiments of Formula I-X1, $R^a$ is —H.

In one or more embodiments of Formula I-X1, $R^3$ is an optionally substituted —$C_1$-$C_6$alkyl. In one or more embodiments of Formula I-X1, $R^3$ is an optionally substituted 3- to 12-membered monocyclic or polycyclic heterocycle. In one or more embodiments of Formula I-X1, $R^3$ is an optionally substituted 3- to 12-membered monocyclic heterocycle. In one or more embodiments of Formula I-X1, $R^3$ is an optionally substituted 5- to 12-membered polycyclic heterocycle.

In one or more embodiments of Formula I-X1, $R^3$ and $R^a$ together with the atom to which they are attached combine to form a 3- to 12-membered monocyclic heterocycle, which is optionally substituted with one or more —$C_1$-$C_6$alkyl, —OH, or —$NH_2$. In one or more embodiments of Formula I-X1, $R^3$ and $R^a$ together with the atom to which they are attached combine to form a 3- to 12-membered monocyclic heterocycle, which is optionally substituted with one or more —$C_1$-$C_6$alkyl or —$NH_2$.

In one or more embodiments of Formula I-X1, $R^3$ and $R^a$ together with the atoms to which they are attached combine to form a 3- to 12-membered polycyclic heterocycle, which is optionally substituted with one or more —$C_1$-$C_6$alkyl, —$NH_2$, or —OH. In one or more embodiments of Formula I-X1, $R^3$ and $R^a$ together with the atom to which they are attached combine to form a 3- to 12-membered polycyclic heterocycle, which is optionally substituted with one or more —$C_1$-$C_6$alkyl or —$NH_2$.

In one or more embodiments of Formula I-X1, $R^3$ and $R^a$ together with the atoms to which they are attached combine to form a 5- to 12-membered spiroheterocycle, which is optionally substituted with one or more —$C_1$-$C_6$alkyl, —$NH_2$, or —OH. In one or more embodiments of Formula I-X1, $R^3$ and $R^a$ together with the atoms to which they are attached combine to form a 5- to 12-membered spiroheterocycle, which is optionally substituted with one or more —$C_1$-$C_6$alkyl or —$NH_2$.

In one or more embodiments of Formula I-X1, $R^3$ and $R^a$ together with the atoms to which they are attached combine to form a 10- to 12-membered spiroheterocycle, which is optionally substituted with one or more —$C_1$-$C_6$alkyl, —$NH_2$, or —OH. In one or more embodiments of Formula I-X1, $R^3$ and $R^a$ together with the atoms to which they are attached combine to form a 10- to 12-membered spiroheterocycle, which is optionally substituted with one or more —$C_1$-$C_6$alkyl or —$NH_2$.

In one or more embodiments of the compounds of Formula I-Y, the compound is of the Formula I-Y1:

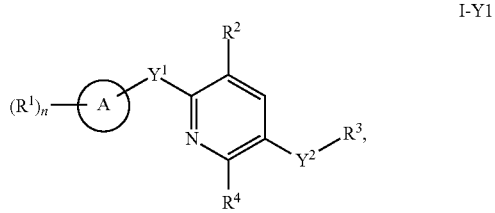

I-Y1 and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, —$NO_2$, oxo, —CN, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —OH, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —$NO_2$, Oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$ $NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$ $NH_2$, —$COOR^b$, —$CONHR^b$, —$CONH(CH_2)_nCOOR^b$, —$NHCOOR^b$, —$CF_3$, —$CHF_2$, or —$CH_2F$;

$R^4$ is —H, -D, —$C_1$-$C_6$alkyl, —NH—$NHR^5$, —NH—$OR^5$, —O—$NR^5R^6$, —$NHC(O)R^5$, —$NHC(O)NHR^5$, —$NHS(O)_2R^5$, —$NHS(O)_2NHR^5$, —$S(O)_2OH$, —C(O) $OR^5$, —$NH(CH_2)_nOH$, —$C(O)NH(CH_2)_nOH$, —C(O)NH $(CH_2)_nR^b$, —$C(O)R^b$, —OH, —CN, —$C(O)NR^5R^6$, —$S(O)_2$ $NR^5R^6$, $C_3$-$C_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula I-Y1, $R^4$ is —$C_1$-$C_6$alkyl, which is optionally substituted with one or more —OH, —$NH_2$, halogen, or oxo. In one or more embodiments of Formula I-Y1, $R^4$ is —$C_1$-$C_6$alkyl, which is substituted with one or more —OH. In certain such embodiments, $R^4$ is —$CH_2$—OH. In one or more embodiments of Formula I-Y1, $R^4$ is —H. In one or more embodiments of Formula I-Y1, $R^4$ is —$C_1$-$C_6$haloalkyl or —$C_1$-$C_6$hydroxyalkyl. In one or more embodiments of Formula I-Y1, $R^4$ is —$CF_2$OH or —CHFOH.

In one or more embodiments of the compounds of Formula I-Y1, $Y^2$ is —$(CR^a{}_2)_m$—. In one or more embodiments of the compounds of Formula I-Y1, $Y^2$ is —$NR^a$—. In one or more embodiments of the compounds of Formula I-Y1, $Y^1$ is —S—. In one or more embodiments of the compounds of Formula I-Y1, $Y^1$ is a direct bond.

In one or more embodiments of Formula I-Y1, A is a monocyclic or polycyclic cycloalkyl. In one or more embodiments of Formula I-Y1, A is a monocyclic or polycyclic heterocycloalkyl. In one or more embodiments of Formula I-Y1, A is monocyclic or polycyclic aryl. In one or more embodiments of Formula I-Y1, A is phenyl. In one or more embodiments of Formula I-Y1, A is monocyclic or polycyclic heteroaryl. In one or more embodiments of Formula I-Y1, A is pyridinyl.

In one or more embodiments of Formula I-Y1, n is independently, at each occurrence, 0, 1, 2, or 3. In one or more embodiments of Formula I-Y1, n is independently, at each occurrence, 1 or 2.

In one or more embodiments of Formula I-Y1, $R^1$ is independently, at each occurrence, —H, halogen or —$NR^5R^6$. In certain such embodiments, $R^5$ and $R^6$ are both —H. In one or more embodiments of Formula I-Y1, $R^1$ is independently, at each occurrence, —H, methyl, fluoro, chloro, or —$NH_2$.

In one or more embodiments of Formula I-Y1, $R^2$ is —OH. In one or more embodiments of Formula I-Y1, $R^2$ is an optionally substituted —$C_1$-$C_6$alkyl. In certain such embodiments, $R^2$ is methyl.

In one or more embodiments of Formula I-Y1, $R^a$ is —H.

In one or more embodiments of Formula I-Y1, $R^3$ is an optionally substituted —$C_1$-$C_6$alkyl. In one or more embodiments of Formula I-Y1, $R^3$ is an optionally substituted 3- to 12-membered monocyclic or polycyclic heterocycle. In one or more embodiments of Formula I-Y1, $R^3$ is an optionally substituted 3- to 12-membered monocyclic heterocycle. In one or more embodiments of Formula I-Y1, $R^3$ is an optionally substituted 5- to 12-membered polycyclic heterocycle.

In one or more embodiments of Formula I-Y1, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y1, $R^3$ and $R^a$ together with the atom to which they are attached combine to form a 3- to 12-membered monocyclic heterocycle, which is optionally substituted with one or more —$C_1$-$C_6$alkyl or —$NH_2$. In one or more embodiments of Formula I-Y1, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y1, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y1, $R^3$ and $R^a$ together with the atom to which they are attached combine to form a 3- to 12-membered polycyclic heterocycle, which is optionally substituted with one or more —$C_1$-$C_6$alkyl or —$NH_2$. In one or more embodiments of Formula I-Y1, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y1, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y1, $R^3$ and $R^a$ together with the atoms to which they are attached combine to form a 5- to 12-membered spiroheterocycle, which is optionally substituted with one or more —$C_1$-$C_6$alkyl or —$NH_2$. In one or more embodiments of Formula I-Y1, $R^3$ and $R^a$ together with the atom to which they are attached combine to form a 5- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y1, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y1, $R^3$ and $R^a$ together with the atoms to which they are attached combine to form a 10- to 12-membered spiroheterocycle, which is optionally substituted with one or more —$C_1$-$C_6$alkyl or —$NH_2$. In one or more embodiments of Formula I-Y1, $R^3$ and $R^a$ together with the atom to which they are attached combine to form a 10- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of the compounds of Formula I-Y or I-Y1, the compound is of the Formula I-Y2:

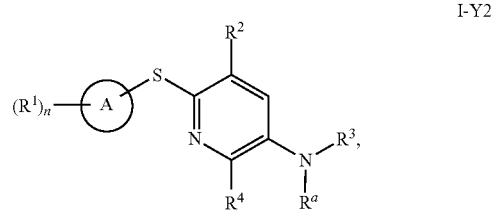

I-Y2 and pharmaceutically acceptable salts, prodrugs, solvates, hydrates, tautomers, or isomers thereof.

In one or more embodiments of Formula I-Y2, A is a monocyclic or polycyclic heterocycloalkyl. In one or more embodiments of Formula I-Y2, A is monocyclic or polycyclic aryl. In one or more embodiments of Formula I-Y2, A is phenyl. In one or more embodiments of Formula I-Y2, A is monocyclic or polycyclic heteroaryl. In one or more embodiments of Formula I-Y2, A is pyridinyl.

In one or more embodiments of Formula I-Y2, n is independently, at each occurrence, 0, 1, 2, or 3. In one or more embodiments of Formula I-Y2, n is independently, at each occurrence, 1 or 2.

In one or more embodiments of Formula I-Y2, $R^1$ is independently, at each occurrence, —H, halogen or —$NR^5R^6$. In certain such embodiments, $R^5$ and $R^6$ are both —H. In one or more embodiments of Formula I-Y2, $R^1$ is independently, at each occurrence, —H, methyl, fluoro, chloro, or —$NH_2$.

In one or more embodiments of Formula I-Y2, $R^2$ is —OH. In one or more embodiments of Formula I-Y2, $R^2$ is an optionally substituted —$C_1$-$C_6$alkyl. In certain such embodiments, $R^2$ is methyl.

In one or more embodiments of Formula I-Y2, $R^4$ is —$C_1$-$C_6$alkyl, which is optionally substituted with one or more —OH, —$NH_2$, halogen, or oxo. In one or more embodiments of Formula I-Y2, $R^4$ is —$C_1$-$C_6$alkyl, which is substituted with one or more —OH. In certain such embodiments, $R^4$ is —$CH_2$—OH. In one or more embodiments of Formula I-Y2, $R^4$ is —H. In one or more embodiments of Formula I-Y2, $R^4$ is —$C_1$-$C_6$haloalkyl or —$C_1$-$C_6$hydroxyalkyl. In one or more embodiments of Formula I-Y2, $R^4$ is —$CF_2$OH or —CHFOH.

In one or more embodiments of Formula I-Y2, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y2, $R^3$ and $R^a$ together with the atom to which they are attached combine to form a 3- to 12-membered monocyclic heterocycle, which is optionally substituted with one or more —$C_1$-$C_6$alkyl or —$NH_2$. In one or more embodiments of Formula I-Y2, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y2, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y2, $R^3$ and $R^a$ together with the atom to which they are attached combine to form a 3- to 12-membered polycyclic heterocycle, which is optionally substituted with one or more —$C_1$-$C_6$alkyl or —$NH_2$. In one or more embodiments of Formula I-Y2, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y2, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y2, $R^3$ and $R^a$ together with the atoms to which they are attached combine to form a 5- to 12-membered spiroheterocycle, which is optionally substituted with one or more —$C_1$-$C_6$alkyl or —$NH_2$. In one or more embodiments of Formula I-Y2, $R^3$ and $R^a$ together with the atom to which they are attached combine to form a 5- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Y2, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y2, $R^3$ and $R^a$ together with the atoms to which they are attached combine to form a 10- to 12-membered spiroheterocycle, which is optionally substituted with one or more —$C_1$-$C_6$alkyl or —$NH_2$. In one or more embodiments of Formula I-Y2, $R^3$ and $R^a$ together with the atom to which they are attached combine to form a 10- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of the compounds of the Formula I-Y or I-Y1, the compound is of the Formula I-Y3:

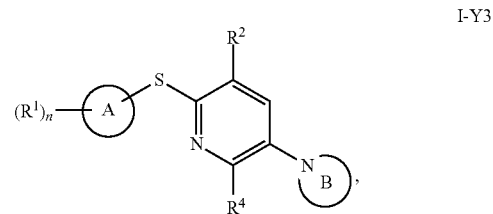

I-Y3 and pharmaceutically acceptable salts, prodrugs, solvates, hydrates, tautomers, or isomers thereof, wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, —$NH_2$, —$CF_3$, —$CHF_2$, or —$CH_2F$. In certain such embodiments, the heterocycle or spiroheterocycle is optionally substituted with one or more —$C_1$-$C_6$alkyl or —$NH_2$.

In one or more embodiments of Formula I-Y3, A is a monocyclic or polycyclic heterocycloalkyl. In one or more embodiments of Formula I-Y3, A is monocyclic or polycyclic aryl. In one or more embodiments of Formula I-Y3, A is phenyl. In one or more embodiments of Formula I-Y3, A is monocyclic or polycyclic heteroaryl. In one or more embodiments of Formula I-Y3, A is pyridinyl.

In one or more embodiments of Formula I-Y3, n is independently, at each occurrence, 0, 1, 2, or 3. In one or more embodiments of Formula I-Y3, n is independently, at each occurrence, 1 or 2.

In one or more embodiments of Formula I-Y3, $R^1$ is independently, at each occurrence, —H, halogen or —$NR^5R^6$. In certain such embodiments, $R^5$ and $R^6$ are both —H. In one or more embodiments of Formula I-Y3, $R^1$ is independently, at each occurrence, —H, methyl, fluoro, chloro, or —$NH_2$.

In one or more embodiments of Formula I-Y3, $R^2$ is —OH. In one or more embodiments of Formula I-Y3, $R^2$ is an optionally substituted —$C_1$-$C_6$alkyl. In certain such embodiments, $R^2$ is methyl.

In one or more embodiments of Formula I-Y3, $R^4$ is —$C_1$-$C_6$alkyl, which is optionally substituted with one or more —OH, —$NH_2$, halogen, or oxo. In one or more embodiments of Formula I-Y3, $R^4$ is —$C_1$-$C_6$alkyl, which is substituted with one or more —OH. In certain such embodiments, $R^4$ is —$CH_2$—OH. In one or more embodiments of Formula I-Y3, $R^4$ is —H. In one or more embodiments of Formula I-Y3, $R^4$ is —$C_1$-$C_6$haloalkyl or —$C_1$-$C_6$hydroxyalkyl. In one or more embodiments of Formula I-Y3, $R^4$ is —$CF_2$OH or —CHFOH.

In one or more embodiments of the compounds of Formula I-Y or I-Y1, the compound is of the Formula I-Y4:

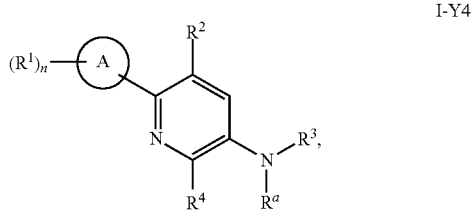

I-Y4 and pharmaceutically acceptable salts, prodrugs, solvates, hydrates, tautomers, or isomers thereof.

In one or more embodiments of Formula I-Y4, A is a monocyclic or polycyclic heterocycloalkyl. In one or more embodiments of Formula I-Y4, A is monocyclic or polycyclic aryl. In one or more embodiments of Formula I-Y4, A is phenyl. In one or more embodiments of Formula I-Y4, A is monocyclic or polycyclic heteroaryl. In one or more embodiments of Formula I-Y4, A is pyridinyl.

In one or more embodiments of Formula I-Y4, n is independently, at each occurrence, 0, 1, 2, or 3. In one or more embodiments of Formula I-Y4, n is independently, at each occurrence, 1 or 2.

In one or more embodiments of Formula I-Y4, $R^1$ is independently, at each occurrence, —H, halogen or —$NR^5R^6$. In certain such embodiments, $R^5$ and $R^6$ are both —H. In one or more embodiments of Formula I-Y4, $R^1$ is independently, at each occurrence, —H, methyl, fluoro, chloro, or —$NH_2$.

In one or more embodiments of Formula I-Y4, $R^2$ is —OH. In one or more embodiments of Formula I-Y4, $R^2$ is an optionally substituted —$C_1$-$C_6$alkyl. In certain such embodiments, $R^2$ is methyl.

In one or more embodiments of Formula I-Y4, $R^4$ is —$C_1$-$C_6$alkyl, which is optionally substituted with one or more —OH, —$NH_2$, halogen, or oxo. In one or more embodiments of Formula I-Y4, $R^4$ is —$C_1$-$C_6$alkyl, which is substituted with one or more —OH. In certain such embodiments, $R^4$ is —$CH_2$—OH. In one or more embodiments of Formula I-Y4, $R^4$ is —H. In one or more embodiments of Formula I-Y4, $R^4$ is —$C_1$-$C_6$haloalkyl or —$C_1$-$C_6$hydroxyalkyl. In one or more embodiments of Formula I-Y4, $R^4$ is —$CF_2$OH or —CHFOH.

In one or more embodiments of Formula I-Y4, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$CF_3$, —$CHF_2$, or —$CH_2$F. In one or more embodiments of Formula I-Y4, $R^3$ and $R^a$ together with the atom to which they are attached combine to form a 3- to 12-membered monocyclic heterocycle, which is optionally substituted with one or more —$C_1$-$C_6$alkyl or —$NH_2$. In one or more embodiments of Formula I-Y4, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2$F.

In one or more embodiments of Formula I-Y4, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$CF_3$, —$CHF_2$, or —$CH_2$F. In one or more embodiments of Formula I-Y4, $R^3$ and $R^a$ together with the atom to which they are attached combine to form a 3- to 12-membered polycyclic heterocycle, which is optionally substituted with one or more —$C_1$-$C_6$alkyl or —$NH_2$. In one or more embodiments of Formula I-Y4, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2$F.

In one or more embodiments of Formula I-Y4, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$CF_3$, —$CHF_2$, or —$CH_2$F. In one or more embodiments of Formula I-Y4, $R^3$ and $R^a$ together with the atoms to which they are attached combine to form a 5- to 12-membered spiroheterocycle, which is optionally substituted with one or more —$C_1$-$C_6$alkyl or —$NH_2$. In one or more embodiments of Formula I-Y4, $R^3$ and $R^a$ together with the atom to which they are attached combine to form a 5- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2$F.

In one or more embodiments of Formula I-Y4, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$CF_3$, —$CHF_2$, or —$CH_2$F. In one or more embodiments of Formula I-Y4, $R^3$ and $R^a$ together with the atoms to which they are attached combine to form a 10- to 12-membered spiroheterocycle, which is optionally substituted with one or more —$C_1$-$C_6$alkyl or —$NH_2$. In one or more embodiments of Formula I-Y4, $R^3$ and $R^a$ together with the atom to which they are attached combine to form a 10- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2$F.

In one or more embodiments of the compounds of the Formula I-Y or I-Y1, the compound is of the Formula I-Y5:

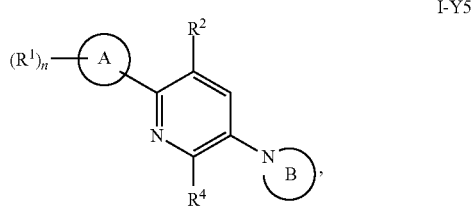

I-Y5 and pharmaceutically acceptable salts, prodrugs, solvates, hydrates, tautomers, or isomers thereof, wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, —$NH_2$, —$CF_3$, —$CHF_2$, or —$CH_2F$. In certain such embodiments, the heterocycle or spiroheterocycle is optionally substituted with one or more —$C_1$-$C_6$alkyl or —$NH_2$.

In one or more embodiments of Formula I-Y5, A is a monocyclic or polycyclic heterocycloalkyl. In one or more embodiments of Formula I-Y5, A is monocyclic or polycyclic aryl. In one or more embodiments of Formula I-Y5, A is phenyl. In one or more embodiments of Formula I-Y5, A is monocyclic or polycyclic heteroaryl. In one or more embodiments of Formula I-Y5, A is pyridinyl.

In one or more embodiments of Formula I-Y5, n is independently, at each occurrence, 0, 1, 2, or 3. In one or more embodiments of Formula I-Y5, n is independently, at each occurrence, 1 or 2.

In one or more embodiments of Formula I-Y5, $R^1$ is independently, at each occurrence, —H, halogen or —$NR^5R^6$. In certain such embodiments, $R^5$ and $R^6$ are both —H. In one or more embodiments of Formula I-Y5, $R^1$ is independently, at each occurrence, —H, methyl, fluoro, chloro, or —$NH_2$.

In one or more embodiments of Formula I-Y5, $R^2$ is —OH. In one or more embodiments of Formula I-Y5, $R^2$ is an optionally substituted —$C_1$-$C_6$alkyl. In certain such embodiments, $R^2$ is methyl.

In one or more embodiments of Formula I-Y5, $R^4$ is —$C_1$-$C_6$alkyl, which is optionally substituted with one or more —OH, —$NH_2$, halogen, or oxo. In one or more embodiments of Formula I-Y5, $R^4$ is —$C_1$-$C_6$alkyl, which is substituted with one or more —OH. In certain such embodiments, $R^4$ is —$CH_2$—OH. In one or more embodiments of Formula I-Y5, $R^4$ is —H. In one or more embodiments of Formula I-Y5, $R^4$ is —$C_1$-$C_6$haloalkyl or —$C_1$-$C_6$hydroxyalkyl. In one or more embodiments of Formula I-Y5, $R^4$ is —$CF_2$OH or —CHFOH.

The present disclosure provides a compound of Formula I-Y2 or I-Y4 having one, two, three, four, or more of the following features:
a) A is monocyclic or polycyclic aryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is phenyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is monocyclic or polycyclic heteroaryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is pyridinyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, or —$NH_2$; and
f) $R^4$ is-$CH_2$—OH.

The present disclosure provides a compound of Formula I-Y2 or I-Y4 having one, two, three, four, or more of the following features:
a) A is monocyclic or polycyclic aryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is phenyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is monocyclic or polycyclic heteroaryl;
b) n is independently, at each occurrence, 1 or 2;

c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y2 or I-Y4 having one, two, three, four, or more of the following features:
a) A is pyridinyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) $R^3$ and $R^a$ together with the atom to which they are attached combine to form a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is monocyclic or polycyclic aryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is phenyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 3- to 12-membered monocyclic or polycyclic heterocycle, which is optionally substituted with one or more —$C_1$-$C_6$alkyl, —OH, —$NH_2$; and
f) $R^4$ is —$CH_2$—OH.

The present disclosure provides a compound of Formula I-Y3 or I-Y5 having one, two, three, four, or more of the following features:
a) A is monocyclic or polycyclic heteroaryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is pyridinyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 3- to 12-membered monocyclic or polycyclic heterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is monocyclic or polycyclic aryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is phenyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is monocyclic or polycyclic heteroaryl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 5- to 12-membered spiroheterocycle, which is optionally substituted with one or more —$C_1$-$C_6$alkyl, —OH, or —$NH_2$; and
f) $R^4$ is —$CH_2$—OH.

The present disclosure provides a compound of Formula I-Y3 or I-Y5 having one, two, three, four, or more of the following features:
a) A is pyridinyl;
b) n is independently, at each occurrence, 1 or 2;
c) $R^1$ is independently, at each occurrence, —H, optionally substituted —$C_1$-$C_6$alkyl, halogen, or —$NH_2$;
d) $R^2$ is an optionally substituted —$C_1$-$C_6$alkyl, such as methyl, or —OH;
e) B is a 5- to 12-membered spiroheterocycle, which is optionally substituted with one or more —$C_1$-$C_6$alkyl, —OH, or —$NH_2$; and
f) $R^4$ is-$CH_2$—OH.

In one or more embodiments of the compounds of Formula I-Y or Formula I-Y1, the compound is of Formula I-Y6:

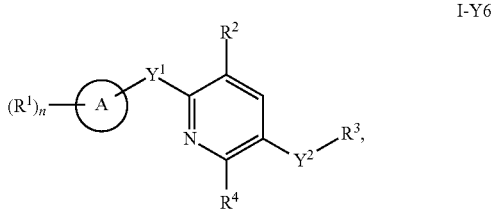

and pharmaceutically acceptable salts, prodrugs, solvates, hydrates, tautomers, or isomers thereof, wherein:

A is a 5- to 12-membered monocyclic or polycyclic aryl or heteroaryl;

$Y^1$ is —S—;

$Y^2$ is —$NR^a$—; wherein the bond on the left side of $Y^2$, as drawn, is bound to the pyridine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, —$CF_3$, —$CHF_2$, or —$CH_2F$;

$R^1$ is independently, at each occurrence, —H, —$C_1$-$C_6$alkyl, —OH, halogen, or —$NR^5R^6$;

$R^2$ is —$C_1$-$C_6$alkyl or —OH;

$R^4$ is —H, —$C_1$-$C_6$alkyl, —$C_1$-$C_6$haloalkyl, —$C_1$-$C_6$hydroxyalkyl, —$CH_2OH$, —$CF_2OH$, or —CHFOH, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

In one or more embodiments of Formula I-Y6, $R^4$ is —$C_1$-$C_6$alkyl, which is optionally substituted with one or more —OH, —$NH_2$, halogen, or oxo. In one or more embodiments of Formula I-Y6, $R^4$ is —$C_1$-$C_6$alkyl, which is substituted with one or more —OH. In one or more embodiments of Formula I-Y6, $R^4$ is —$CH_2$—OH. In one or more embodiments of Formula I-Y6, $R^4$ is —H. In one or more embodiments of Formula I-Y6, $R^4$ is —$C_1$-$C_6$haloalkyl or —$C_1$-$C_6$hydroxyalkyl. In one or more embodiments of Formula I-Y6, $R^4$ is —$CF_2OH$ or —CHFOH.

In one or more embodiments of Formula I-Y6, $R^2$ is —OH. In one or more embodiments of Formula I-Y6, $R^2$ is —$C_1$-$C_6$alkyl. In certain such embodiments, $R^2$ is methyl.

In one or more embodiments of Formula I-Y6, A is monocyclic or polycyclic aryl. In one or more embodiments of Formula I-Y6, A is phenyl. In one or more embodiments of Formula I-Y6, A is monocyclic or polycyclic heteroaryl. In one or more embodiments of Formula I-Y6, A is pyridinyl.

In one or more embodiments of Formula I-Y6, n is independently, at each occurrence, 0, 1, 2, or 3. In one or more embodiments of Formula I-Y6, n is independently, at each occurrence, 1 or 2.

In one or more embodiments of Formula I-Y6, $R^1$ is independently, at each occurrence, —H, halogen or —$NR^5R^6$. In certain such embodiments, $R^5$ and $R^6$ are both —H. In one or more embodiments of Formula I-Y6, $R^1$ is independently, at each occurrence, —H, methyl, fluoro, chloro, or —$NH_2$.

In one or more embodiments of Formula I-Y6, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y6, $R^3$ and $R^a$ together with the atom to which they are attached combine to form a 3- to 12-membered monocyclic heterocycle, which is optionally substituted with one or more —$C_1$-$C_6$alkyl or —$NH_2$.

In one or more embodiments of Formula I-Y6, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Y6, $R^3$ and $R^a$ together with the atom to which they are attached combine to form a 3- to 12-membered polycyclic heterocycle, which is optionally substituted with one or more —$C_1$-$C_6$alkyl or —$NH_2$.

In one or more embodiments of Formula I-Y6, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y6, $R^3$ and $R^a$ together with the atoms to which they are attached combine to form a 5- to 12-membered spiroheterocycle, which is optionally substituted with one or more —$C_1$-$C_6$alkyl or —$NH_2$.

In one or more embodiments of Formula I-Y6, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Y6, $R^3$ and $R^a$ together with the atoms to which they are attached combine to form a 10- to 12-membered spiroheterocycle, which is optionally substituted with one or more —$C_1$-$C_6$alkyl or —$NH_2$.

In one or more embodiments of the compounds of Formula I-Y or Formula I-Y1, the compound is of Formula I-Y7:

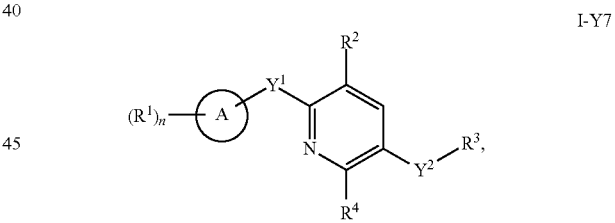

and pharmaceutically acceptable salts, prodrugs, solvates, hydrates, tautomers, or isomers thereof, wherein:

A is a 5- to 12-membered monocyclic or polycyclic aryl or heteroaryl;

$Y^1$ is a direct bond;

$Y^2$ is —$NR^a$—; wherein the bond on the left side of $Y^2$, as drawn, is bound to the pyridine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, —$CF_3$, —$CHF_2$, or —$CH_2F$;

$R^1$ is independently, at each occurrence, —H, —$C_1$-$C_6$alkyl, —OH, halogen, or —$NR^5R^6$;

$R^2$ is —$C_1$-$C_6$alkyl or —OH;

$R^4$ is —H, —$C_1$-$C_6$alkyl, —$C_1$-$C_6$haloalkyl, —$C_1$-$C_6$hydroxyalkyl, —$CH_2OH$, —$CF_2OH$, or —CHFOH, wherein alkyl is optionally substituted with one or more —OH, —NH₂, halogen, or oxo; or R⁵ and R⁶ are each independently, at each occurrence, —H or —C₁-C₆alkyl; and n is independently, at each occurrence, 1, 2, 3, 4, 5, 6, 7, 8, 9, or 10.

In one or more embodiments of Formula I-Y7, R⁴ is —C₁-C₆alkyl, which is optionally substituted with one or more —OH, —NH₂, halogen, or oxo. In one or more embodiments of Formula I-Y7, R⁴ is —C₁-C₆alkyl, which is substituted with one or more —OH. In one or more embodiments of Formula I-Y7, R⁴ is —CH₂—OH. In one or more embodiments of Formula I-Y7, R⁴ is —H. In one or more embodiments of Formula I-Y7, R⁴ is —C₁-C₆haloalkyl or —C₁-C₆hydroxyalkyl. In one or more embodiments of Formula I-Y7, R⁴ is —CF₂OH or —CHFOH.

In one or more embodiments of Formula I-Y7, R² is —OH. In one or more embodiments of Formula I-Y7, R² is —C₁-C₆alkyl. In certain such embodiments, R² is methyl.

In one or more embodiments of Formula I-Y7, A is monocyclic or polycyclic aryl. In one or more embodiments of Formula I-Y7, A is phenyl. In one or more embodiments of Formula I-Y7, A is monocyclic or polycyclic heteroaryl. In one or more embodiments of Formula I-Y7, A is pyridinyl.

In one or more embodiments of Formula I-Y7, n is independently, at each occurrence, 0, 1, 2, or 3. In one or more embodiments of Formula I-Y7, n is independently, at each occurrence, 1 or 2.

In one or more embodiments of Formula I-Y7, R¹ is independently, at each occurrence, —H, halogen or —NR⁵R⁶. In certain such embodiments, R⁵ and R⁶ are both —H. In one or more embodiments of Formula I-Y7, R¹ is independently, at each occurrence, —H, methyl, fluoro, chloro, or —NH₂.

In one or more embodiments of Formula I-Y7, R³ and Rᵃ together with the atom to which they are attached combine to form a 3- to 12-membered monocyclic heterocycle, which is optionally substituted with one or more —C₁-C₆alkyl, —NH₂, —OH, —CF₃, —CHF₂, or —CH₂F. In one or more embodiments of Formula I-Y7, R³ and Rᵃ together with the atom to which they are attached combine to form a 3- to 12-membered monocyclic heterocycle, which is optionally substituted with one or more —C₁-C₆alkyl or —NH₂.

In one or more embodiments of Formula I-Y7, R³ and Rᵃ together with the atoms to which they are attached combine to form a 3- to 12-membered polycyclic heterocycle, which is optionally substituted with one or more —C₁-C₆alkyl, —NH₂, —OH, —CF₃, —CHF₂, or —CH₂F. In one or more embodiments of Formula I-Y7, R³ and Rᵃ together with the atom to which they are attached combine to form a 3- to 12-membered polycyclic heterocycle, which is optionally substituted with one or more —C₁-C₆alkyl or —NH₂.

In one or more embodiments of Formula I-Y7, R³ and Rᵃ together with the atoms to which they are attached combine to form a 5- to 12-membered spiroheterocycle, which is optionally substituted with one or more —C₁-C₆alkyl, —NH₂, —OH, —CF₃, —CHF₂, or —CH₂F. In one or more embodiments of Formula I-Y7, R³ and Rᵃ together with the atoms to which they are attached combine to form a 5- to 12-membered spiroheterocycle, which is optionally substituted with one or more —C₁-C₆alkyl or —NH₂.

In one or more embodiments of Formula I-Y7, R³ and Rᵃ together with the atoms to which they are attached combine to form a 10- to 12-membered spiroheterocycle, which is optionally substituted with one or more —C₁-C₆alkyl, —NH₂, —OH, —CF₃, —CHF₂, or —CH₂F. In one or more embodiments of Formula I-Y7, R³ and Rᵃ together with the atoms to which they are attached combine to form a 10- to 12-membered spiroheterocycle, which is optionally substituted with one or more —C₁-C₆alkyl or —NH₂.

In one or more embodiments of the compounds of Formula I-Z, the compound is of the Formula I-Z1:

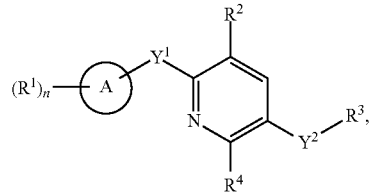

I-Z1 and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y¹ is —S—, a direct bond, —NH—, —S(O)₂—, —S(O)₂—NH—, —C(=CH₂)—, —CH—, or —S(O)—;

Y² is —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyridine ring and the bond on the right side of the Y² moiety, as drawn, is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, —NO₂, oxo, —CN, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —OH, —CN, —C₁-C₆alkyl, —C₂-C₆alkenyl, —C₄-C₈cycloalkenyl, —C₂-C₆alkynyl, F, Br, I, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO₂, Oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, Oxo, —CN, —$R^5$, —$OR^5$, —$NR^5R^6$, —$SR^5$, —$S(O)_2NR^5R^6$, —$S(O)_2R^5$, —$NR^5S(O)_2$ $NR^5R^6$, —$NR^5S(O)_2R^6$, —$S(O)NR^5R^6$, —$S(O)R^5$, —$NR^5S$ $(O)NR^5R^6$, —$NR^5S(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, —$C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$ $NH_2$, —$COOR^b$, —$CONHR^b$, —$CONH(CH_2)_nCOOR^b$, —$NHCOOR^b$, —$CF_3$, —$CHF_2$, or —$CH_2F$;

$R^4$ is —H, -D, —$C_1$-$C_6$alkyl, —NH—$NHR^5$, —NH—$OR^5$, —O—$NR^5R^6$, —NHC(O)$R^5$, —NHC(O)$NHR^5$, —NHS(O)$_2R^5$, —NHS(O)$_2NHR^5$, —S(O)$_2$OH, —C(O) $OR^5$, —$NH(CH_2)_nOH$, —$C(O)NH(CH_2)_nOH$, —C(O)NH $(CH_2)_nR^b$, —$C(O)R^b$, —OH, —CN, —$C(O)NR^5R^6$, —$S(O)_2$ $NR^5R^6$, $C_3$-$C_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of Formula I-Z1, $R^4$ is —$C_1$-$C_6$alkyl, which is optionally substituted with one or more —OH, —$NH_2$, halogen, or oxo. In one or more embodiments of Formula I-Z1, $R^4$ is —$C_1$-$C_6$alkyl, which is substituted with one or more —OH. In certain such embodiments, $R^4$ is —$CH_2$—OH. In one or more embodiments of Formula I-Z1, $R^4$ is —H. In one or more embodiments of Formula I-Z1, $R^4$ is —$C_1$-$C_6$haloalkyl or —$C_1$-$C_6$hydroxyalkyl. In one or more embodiments of Formula I-Z1, $R^4$ is —$CF_2OH$ or —CHFOH.

In one or more embodiments of the compounds of Formula I-Z1, $Y^2$ is —$(CR^a_2)_m$—. In one or more embodiments of the compounds of Formula I-Z1, $Y^2$ is —$NR^a$—. In one or more embodiments of the compounds of Formula I-Z1, $Y^1$ is —S—. In one or more embodiments of the compounds of Formula I-Z1, $Y^1$ is a direct bond.

In one or more embodiments of Formula I-Z1, A is a monocyclic or polycyclic cycloalkyl. In one or more embodiments of Formula I-Z1, A is a monocyclic or polycyclic heterocycloalkyl. In one or more embodiments of Formula I-Z1, A is monocyclic or polycyclic aryl. In one or more embodiments of Formula I-Z1, A is phenyl. In one or more embodiments of Formula I-Z1, A is monocyclic or polycyclic heteroaryl. In one or more embodiments of Formula I-Z1, A is pyridinyl.

In one or more embodiments of Formula I-Z1, n is independently, at each occurrence, 0, 1, 2, or 3. In one or more embodiments of Formula I-Z1, n is independently, at each occurrence, 1 or 2.

In one or more embodiments of Formula I-Z1, $R^1$ is independently, at each occurrence, —H, halogen or —$NR^5R^6$. In certain such embodiments, $R^5$ and $R^6$ are both —H. In one or more embodiments of Formula I-Z1, $R^1$ is independently, at each occurrence, —H, methyl, fluoro, chloro, or —$NH_2$.

In one or more embodiments of Formula I-Z1, $R^2$ is —OH. In one or more embodiments of Formula I-Z1, $R^2$ is an optionally substituted —$C_1$-$C_6$alkyl. In certain such embodiments, $R^2$ is methyl.

In one or more embodiments of Formula I-Z1, $R^3$ and $R^a$ together with the atom to which they are attached combine to form a 3- to 12-membered monocyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Z1, $R^3$ and $R^a$ together with the atom to which they are attached combine to form a 3- to 12-membered monocyclic heterocycle, which is optionally substituted with one or more —$C_1$-$C_6$alkyl or —$NH_2$. In one or more embodiments of Formula I-Z1, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Z1, $R^3$ and $R^a$ together with the atoms to which they are attached combine to form a 3- to 12-membered polycyclic heterocycle, which is optionally substituted with one or more —$C_1$-$C_6$alkyl, —$NH_2$, —OH, —$CF_3$, —$CHF_2$, or —$CH_2F$. In one or more embodiments of Formula I-Z1, $R^3$ and $R^a$ together with the atom to which they are attached combine to form a 3- to 12-membered polycyclic heterocycle, which is optionally substituted with one or more —$C_1$-$C_6$alkyl or —$NH_2$. In one or more embodiments of Formula I-Z1, $R^3$ and $R^a$ together with the atom to which they are attached combine to form a 3- to 12-membered polycyclic heterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Z1, $R^3$ and $R^a$ together with the atoms to which they are attached combine to form a 5- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Z1, $R^3$ and $R^a$ together with the atoms to which they are attached combine to form a 5- to 12-membered spiroheterocycle, which is optionally substituted with one or more —$C_1$-$C_6$alkyl or —$NH_2$. In one or more embodiments of Formula I-Z1, $R^3$ and $R^a$ together with the atom to which they are attached combine to form a 5- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Z1, $R^3$ and $R^a$ together with the atoms to which they are attached combine to form a 10- to 12-membered spiroheterocycle, which is optionally substituted with one or more —$C_1$-$C_6$alkyl, —$NH_2$, —OH, —$CF_3$, —$CHF_2$, or —$CH_2F$. In one or more embodiments of Formula I-Z1, $R^3$ and $R^a$ together with the atoms to which they are attached combine to form a 10- to 12-membered spiroheterocycle, which is optionally substituted with one or more —$C_1$-$C_6$alkyl or —$NH_2$. In one or more embodiments of Formula I-Z1, $R^3$ and $R^a$ together with the atom to which they are attached combine to form a 10- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

In one or more embodiments of Formula I-Z1, $R^a$ is —H.

In one or more embodiments of Formula I-Z1, $R^3$ is an optionally substituted —$C_1$-$C_6$alkyl. In one or more embodiments of Formula I-Z1, $R^3$ is an optionally substituted 3- to 12-membered monocyclic or polycyclic heterocycle. In one or more embodiments of Formula I-Z1, $R^3$ is an optionally substituted 3- to 12-membered monocyclic heterocycle. In one or more embodiments of Formula I-Z1, $R^3$ is an optionally substituted 5- to 12-membered polycyclic heterocycle.

In one or more embodiments of Formula I, II, III, I-X, I-Y, or I-Z, A is a 5- to 12-membered monocyclic or polycyclic cycloalkyl. In one or more embodiments of Formula I, II, III, I-X, I-Y, or I-Z, A is a monocyclic or polycyclic heterocycloalkyl. In one or more embodiments of Formula I, II, III, I-X, I-Y, or I-Z, A is monocyclic or polycyclic aryl. In one or more embodiments of Formula I, II, III, I-X, I-Y, or I-Z, A is monocyclic or polycyclic heteroaryl. In one or more embodiments of Formula I, II, III, I-X, I-Y, or I-Z, A is phenyl. In one or more embodiments of Formula I, II, III, I-X, I-Y, or I-Z, A is pyridinyl.

In one or more embodiments of Formula I, I-X, I-Y, or I-Z, $Y^1$ is —S—. In one or more embodiments of Formula I, I-X, I-Y, or I-Z, $Y^1$ is a direct bond.

In one or more embodiments of Formula I, II, III, I-X, I-Y, or I-Z, $Y^2$ is —$NR^a$—. In one or more embodiments of Formula I, II, III, I-X, I-Y, or I-Z, $Y^2$ is —$(CR^a{}_2)_m$—. In one or more embodiments of Formula I, II, III, I-X, I-Y, or I-Z, $Y^2$ is —C(O)—. In one or more embodiments of Formula I, II, III, I-X, I-Y, or I-Z, $Y^2$ is —$C(R^a)_2NH$— or —$(CR^a{}_2)_mO$—. In one or more embodiments of Formula I, II, III, I-X, I-Y, or I-Z, $Y^2$ is —$C(O)N(R^a)$—, —$N(R^a)C(O)$—, —$S(O)_2N(R^a)$—, —$N(R^a)S(O)_2$—, —$N(R^a)C(S)$—, or —$C(S)N(R^a)$—. In one or more embodiments of Formula I, II, III, I-X, I-Y, or I-Z, $Y^2$ is —$N(R^a)C(O)N(R^a)$—, —$N(R^a)C(S)N(R^a)$—, —$OC(O)N(R^a)$—, —$N(R^a)C(O)O$—, or —$C(O)N(R^a)O$—. In one or more embodiments of Formula I, II, III, I-X, I-Y, or I-Z, $Y^2$ is —C(O)O—, —OC(O)—, or —OC(O)O—.

In one or more embodiments of Formula I, II, III, I-X, I-Y, or I-Z, $R^1$ is independently, at each occurrence, selected from —H, optionally substituted —$C_1$-$C_6$alkyl, halogen, —OH, —CN, and —$NR^5R^6$. In one or more embodiments of Formula I, II, III, I-X, I-Y, or I-Z, $R^1$ is independently, at each occurrence, selected from —H, optionally substituted —$C_1$-$C_6$alkyl, halogen, —OH, and —$NR^5R^6$. In one or more embodiments of Formula I, II, III, I-X, I-Y, or I-Z, $R^1$ is independently, at each occurrence, selected from —H, optionally substituted —$C_1$-$C_6$alkyl, halogen, and —$NR^5R^6$. In one or more embodiments of Formula I, II, III, I-X, I-Y, or I-Z, $R^1$ is independently, at each occurrence, selected from —H, methyl, fluoro, chloro, bromo, and —$NH_2$. In one or more embodiments of Formula I, II, III, I-X, I-Y, or I-Z, $R^1$ is independently, at each occurrence, selected from —H, methyl, fluoro, chloro, and —$NH_2$. In one or more embodiments of Formula I, II, III, I-X, I-Y, or I-Z, $R^1$ is —H. In one or more embodiments of Formula I, II, III, I-X, I-Y, or I-Z, $R^1$ is independently, at each occurrence, —H or halogen. In certain such embodiments, the halogen is chloro. In one or more embodiments of Formula I, II, III, I-X, I-Y, or I-Z, $R^1$ is independently, at each occurrence, —H or —$NH_2$.

In one or more embodiments of Formula I, II, III, I-X, I-Y, or I-Z, $R^2$ is —OH. In one or more embodiments of Formula I, II, III, I-X, I-Y, or I-Z, $R^2$ is an optionally substituted —$C_1$-$C_6$alkyl. In certain such embodiments, the —$C_1$-$C_6$alkyl is methyl. In one or more embodiments of Formula I, II, III, I-X, I-Y, or I-Z, $R^2$ is —CN. In one or more embodiments of Formula I, II, III, I-X, I-Y, or I-Z, $R^2$ is an optionally substituted —$C_2$-$C_6$alkenyl. In one or more embodiments of Formula I, II, III, I-X, I-Y, or I-Z, $R^2$ is an optionally substituted —$C_4$-$C_8$cycloalkenyl. In one or more embodiments of Formula I, II, III, I-X, I-Y, or I-Z, $R^2$ is an optionally substituted —$C_2$-$C_6$alkynyl. In one or more embodiments of Formula I, II, III, I-X, I-Y, or I-Z, $R^2$ is optionally substituted —$C_3$-$C_8$cycloalkyl. In one or more embodiments of Formula I, II, III, I-X, I-Y, or I-Z, $R^2$ is aryl. In one or more embodiments of Formula I, II, III, I-X, I-Y, or I-Z, $R^2$ is an optionally substituted heterocyclyl containing 1-5 heteroatoms selected from the group consisting of N, S, P, and O. In one or more embodiments of Formula I, II, III, I-X, I-Y, or I-Z, $R^2$ is an optionally substituted heteroaryl containing 1-5 heteroatoms selected from the group consisting of N, S, P, and O.

In one or more embodiments of Formula I, II, III, I-X, I-Y, or I-Z, $R^a$ is —H. In one or more embodiments of Formula I, II, III, I-X, I-Y, or I-Z, $R^a$ is —OH. In one or more embodiments of Formula I, II, III, I-X, I-Y, or I-Z, $R^a$ is an optionally substituted —$C_3$-$C_8$cycloalkyl. In one or more embodiments of Formula I, II, III, I-X, I-Y, or I-Z, $R^a$ is an optionally substituted —$C_1$-$C_6$alkyl.

In one or more embodiments of Formula I, II, III, I-X, I-Y, or I-Z, $R^b$ is H. In one or more embodiments of Formula I, II, III, I-X, I-Y, or I-Z, $R^b$ is an optionally substituted $C_1$-$C_6$ alkyl. In one or more embodiments of Formula I, II, III, I-X, I-Y, or I-Z, $R^b$ is an optionally substituted —$C_3$-$C_8$cycloalkyl. In one or more embodiments of Formula I, II, III, I-X, I-Y, or I-Z, $R^b$ is an optionally substituted —$C_2$-$C_6$alkenyl. In one or more embodiments of Formula I, II, III, I-X, I-Y, or I-Z, $R^b$ is an optionally substituted heterocyclyl containing 1-5 heteroatoms selected from the group consisting of N, S, P, and O.

In one or more embodiments of Formula I, II, III, I-X, I-Y, or I-Z, $R^3$ is an optionally substituted —$C_1$-$C_6$alkyl. In one or more embodiments of Formula I, II, III, I-X, I-Y, or I-Z, $R^3$ is an optionally substituted 3- to 12-membered monocyclic or polycyclic heterocycle. In one or more embodiments of Formula I, II, III, I-X, I-Y, or I-Z, $R^3$ is an optionally substituted 3- to 12-membered monocyclic heterocycle. In one or more embodiments of Formula I, II, III, I-X, I-Y, or I-Z, $R^3$ is an optionally substituted 5- to 12-membered polycyclic heterocycle.

In one or more embodiments of Formula I, II, III, I-X, I-Y, or I-Z, $R^4$ is —H. In one or more embodiments of Formula I, II, III, I-X, I-Y, or I-Z, $R^4$ is —$C_1$-$C_6$alkyl. In one or more embodiments of Formula I, II, III, I-X, I-Y, or I-Z, $R^4$ is —$C_1$-$C_6$alkyl substituted with one or more —OH, —$NH_2$, halogen, or oxo. In one or more embodiments of Formula I, II, III, I-X, I-Y, or I-Z, $R^4$ is —$C_1$-$C_6$alkyl substituted with —OH. In one or more embodiments of Formula I, II, III, I-X, I-Y, or I-Z, $R^4$ is —$CH_2OH$. In one or more embodiments of Formula I, II, III, I-X, I-Y, or I-Z, $R^4$ is —$CF_2OH$ or —CHFOH, In one or more embodiments of Formula I, II, III, I-X, I-Y, or I-Z, $R^3$ and $R^a$ together with the atom to which they are attached combine to form an optionally substituted 3- to 12-membered monocyclic heterocycle. In one or more embodiments of Formula I, II, III, I-X, I-Y, or I-Z, $R^3$ and $R^a$ together with the atoms to which they are attached combine to form an optionally substituted 3- to 12-membered polycyclic heterocycle. In one or more embodiments of Formula I, II, III, I-X, I-Y, or I-Z, $R^3$ and $R^a$ together with the atoms to which they are attached combine to form an optionally substituted 5- to 12-membered spiroheterocycle.

In one or more embodiments of Formula I, II, III, I-X, I-Y, or I-Z, $R^a$ and $R^4$ together with the atom to which they are attached combine to form an optionally substituted monocyclic or polycyclic 3- to 12-membered cycloalkyl. In one or more embodiments of Formula I, II, III, I-X, I-Y, or I-Z, $R^a$ and $R^4$ together with the atom to which they are attached combine to form an optionally substituted monocyclic or polycyclic 3- to 12-membered heterocycle.

In one variation of Formula I, II, III, I-X, I-Y, or I-Z, $R^2$ is —$C_1$-$C_6$alkyl and $R^4$ is H. In certain instances of Formula I, II, III, I-X, I-Y, or I-Z, $R^2$ is —$C_1$-$C_6$alkyl and $R^4$ is —$C_1$-$C_6$alkyl. In certain instances of Formula I, II, III, I-X, I-Y, or I-Z, $R^2$ is —$C_1$-$C_6$alkyl and $R^4$ is —$C_1$-$C_6$alkyl substituted with one or more —OH, —$NH_2$, halogen, or oxo. In certain instances of Formula I, II, III, I-X, I-Y, or I-Z, $R^2$ is —$C_1$-$C_6$alkyl and $R^4$ is —$C_1$-$C_6$alkyl substituted with —OH. In certain such embodiments, $R^4$ is —$CH_2OH$.

In one variation of Formula I, II, III, I-X, I-Y, or I-Z, $R^2$ is —OH and $R^4$ is H. In certain instances of Formula I, II, III, I-X, I-Y, or I-Z, $R^2$ is —OH and $R^4$ is —$C_1$-$C_6$alkyl. In certain instances of Formula I, II, III, I-X, I-Y, or I-Z, $R^2$ is —OH and $R^4$ is —$C_1$-$C_6$alkyl substituted with one or more —OH, —$NH_2$, halogen, or oxo. In certain instances of Formula I, II, III, I-X, I-Y, or I-Z, $R^2$ is —OH and $R^4$ is —$C_1$-$C_6$alkyl substituted with —OH. In certain such embodiments, $R^4$ is —$CH_2OH$.

In one variation of Formula I, II, III, I-X, I-Y, or I-Z, $Y^1$ is S and A is a 5- to 12-membered monocyclic or polycyclic cycloalkyl. In certain instances of Formula I, II, III, I-X, I-Y, or I-Z, $Y^1$ is S and A is a monocyclic or polycyclic heterocycloalkyl. In certain instances of Formula I, II, III, I-X, I-Y, or I-Z, $Y^1$ is S and A is monocyclic or polycyclic aryl. In certain instances of Formula I, II, III, I-X, I-Y, or I-Z, $Y^1$ is S and A is monocyclic or polycyclic heteroaryl. In certain instances of Formula I, II, III, I-X, I-Y, or I-Z, $Y^1$ is S and A is phenyl. In certain instances of Formula I, II, III, I-X, I-Y, or I-Z, $Y^1$ is S and A is pyridinyl.

In one variation of Formula I, II, III, I-X, I-Y, or I-Z, $Y^1$ is a direct bond and A is a 5- to 12-membered monocyclic or polycyclic cycloalkyl. In certain instances of Formula I, II, III, I-X, I-Y, or I-Z, $Y^1$ is a direct bond and A is a monocyclic or polycyclic heterocycloalkyl. In certain instances of Formula I, II, III, I-X, I-Y, or I-Z, $Y^1$ is a direct bond and A is monocyclic or polycyclic aryl. In certain instances of Formula I, II, III, I-X, I-Y, or I-Z, $Y^1$ is a direct bond and A is monocyclic or polycyclic heteroaryl. In certain instances of Formula I, II, III, I-X, I-Y, or I-Z, $Y^1$ is a direct bond and A is phenyl. In certain instances of Formula I, II, III, I-X, I-Y, or I-Z, $Y^1$ is a direct bond and A is pyridinyl.

In one or more embodiments, a compound of the present disclosure (e.g., a compound of Formula I, II, III, I-X, I-Y, or I-Z) can be selected from:

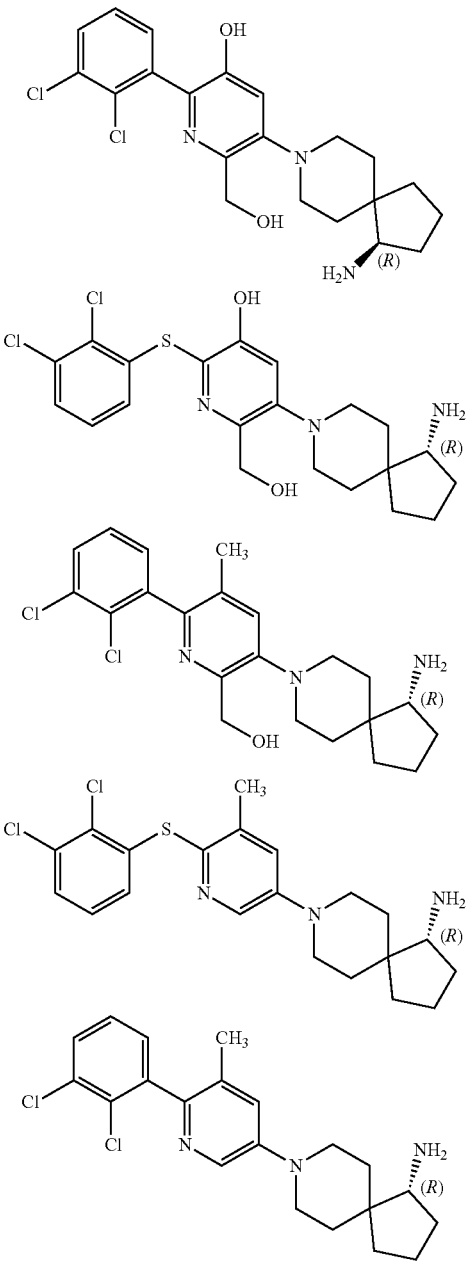

67
-continued
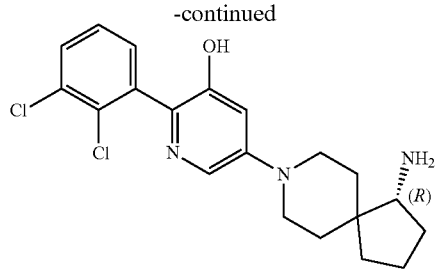
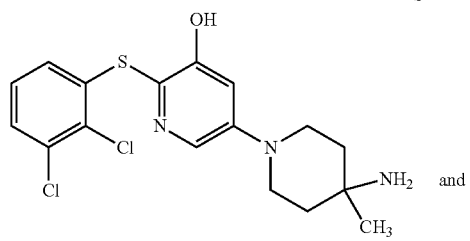 and
68
-continued
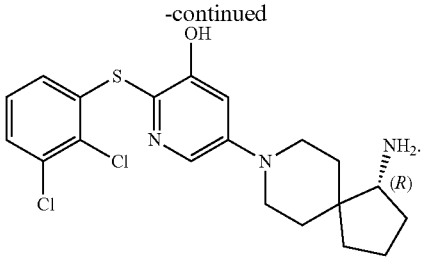
and pharmaceutically acceptable salts, prodrugs, solvates, hydrates, tautomers, or isomers of any of the foregoing.
In one or more embodiments, a compound of the present disclosure (e.g., a compound of Formula I, II, III, I-X, I-Y, or I-Z) can be selected from:
| Example | |
|---|---|
| 1 | 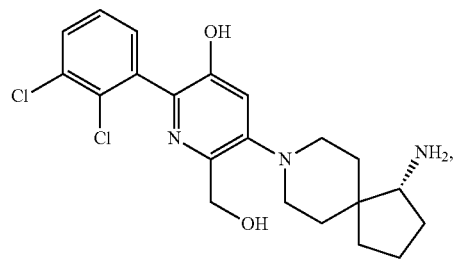 [SMILES: N[C@@H]1CCCC12CCN(c1cc(O)c(-c3cccc(Cl)c3Cl)nc1CO)CC2] |
| 2 | 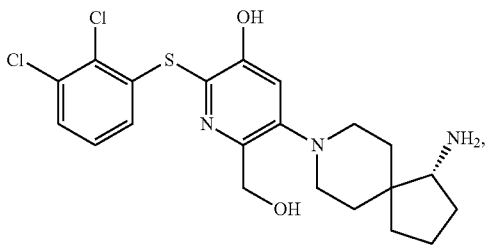 [SMILES: N[C@@H]1CCCC12CCN(c1cc(O)c(Sc3cccc(Cl)c3Cl)nc1CO)CC2] |
| 3 | 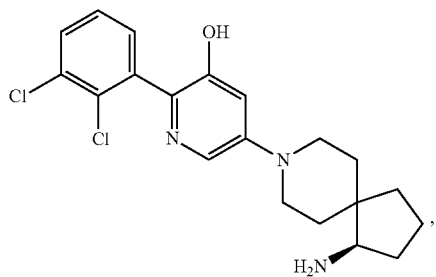 |
| 4 | 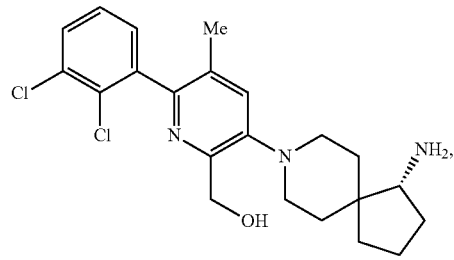 [SMILES: Cc1cc(N2CCC3(CCC[C@H]3N)CC2)c(CO)nc1-c1cccc(Cl)c1Cl] |

-continued
| Example | |
|---|---|
| 5 | 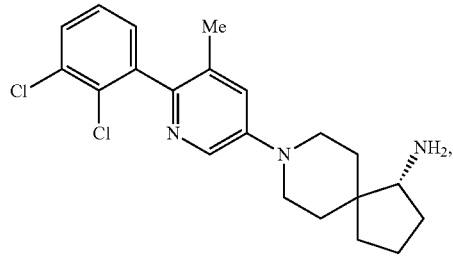 [SMILES: Cc1cc(N2CCC3(CCC[C@H]3N)CC2)cnc1-c1cccc(Cl)c1Cl] |
| 6 | 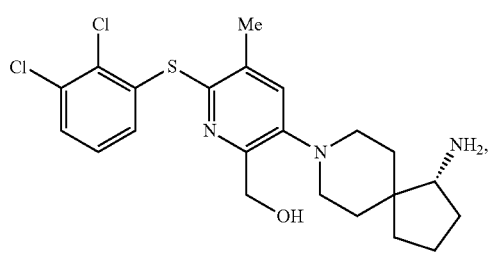 [SMILES: Cc1cc(N2CCC3(CCC[C@H]3N)CC2)c(CO)nc1Sc1cccc(Cl)c1Cl] |
| 7 | 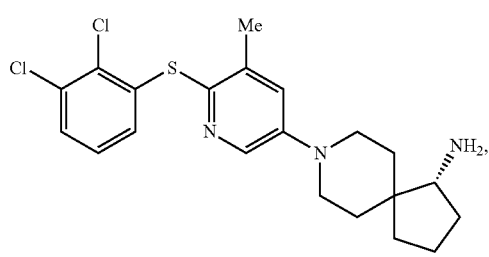 [SMILES: Cc1cc(N2CCC3(CCC[C@H]3N)CC2)cnc1Sc1cccc(Cl)c1Cl] |
| 8 | 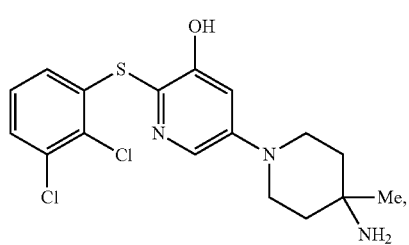 [SMILES: CC1(N)CCN(c2cnc(Sc3cccc(Cl)c3Cl)c(O)c2)CC1] |
| 9 | 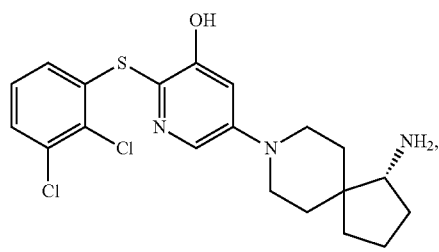 [SMILES: N[C@@H]1CCCC12CCN(c1cnc(Sc3cccc(Cl)c3Cl)c(O)c1)CC2] |
| 10 | 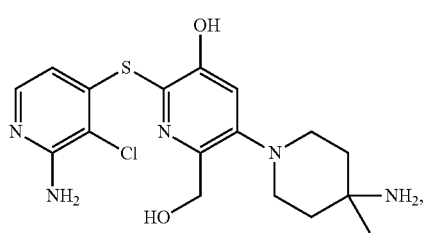 [SMILES: CC1(N)CCN(c2cc(O)c(Sc3ccnc(N)c3Cl)nc2CO)CC1] |

| Example | |
|---|---|
| 11 | 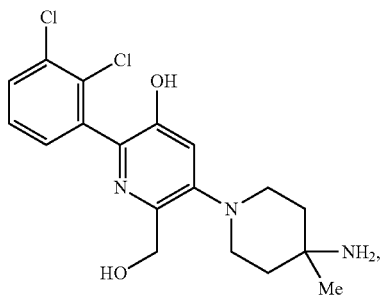 [SMILES: CC1(N)CCN(c2cc(O)c(-c3cccc(Cl)c3Cl)nc2CO)CC1] |
| 12 | 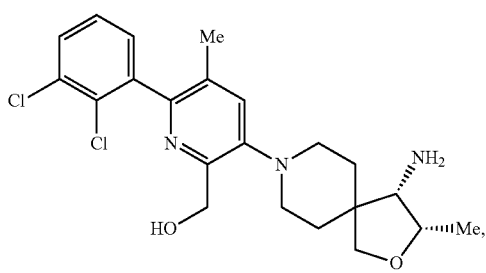 [SMILES: Cc1cc(N2CCC3(CC2)CO[C@@H](C)[C@H]3N)c(CO)nc1-c1cccc(Cl)c1Cl] |
| 13 | 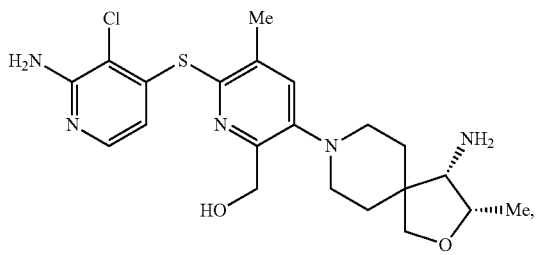 [SMILES: Cc1cc(N2CCC3(CC2)CO[C@@H](C)[C@H]3N)c(CO)nc1Sc1ccnc(N)c1Cl] |
| 14 | 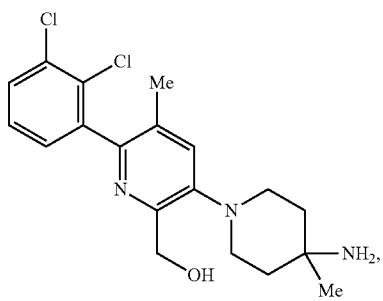 [SMILES: Cc1cc(N2CCC(C)(N)CC2)c(CO)nc1-c1cccc(Cl)c1Cl] |
| 15 | 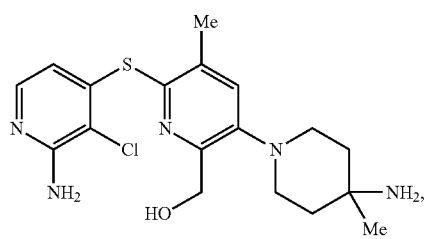 [SMILES: Cc1cc(N2CCC(C)(N)CC2)c(CO)nc1Sc1ccnc(N)c1Cl] |

| Example | |
|---|---|
| 16 | 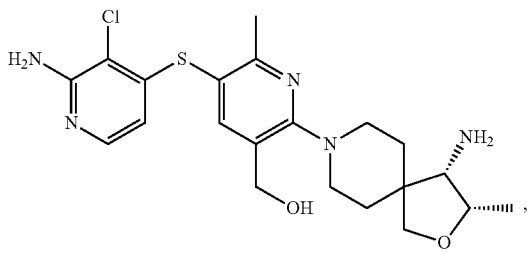 [SMILES: Cc1nc(N2CCC3(CC2)CO[C@@H](C)[C@H]3N)c(CO)cc1Sc1ccnc(N)c1Cl ; ","] |
| 17 | 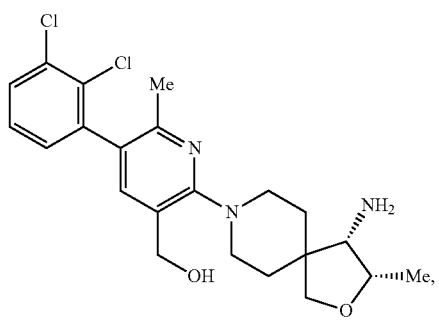 [SMILES: Cc1nc(N2CCC3(CC2)CO[C@@H](C)[C@H]3N)c(CO)cc1-c1cccc(Cl)c1Cl] |
| 18 | 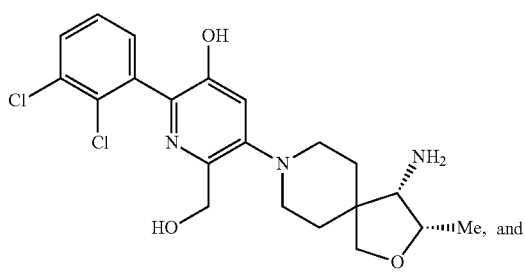 [SMILES: C[C@@H]1OCC2(CCN(c3cc(O)c(-c4cccc(Cl)c4Cl)nc3CO)CC2)[C@@H]1N ; "and"] |
| 19 | 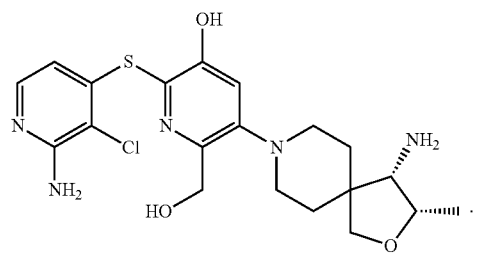 [SMILES: C[C@@H]1OCC2(CCN(c3cc(O)c(Sc4ccnc(N)c4Cl)nc3CO)CC2)[C@@H]1N ; "."] |

Methods of Synthesizing the Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present disclosure.

Those skilled in the art will recognize if a stereocenter exists in any of the compounds of the present disclosure. Accordingly, the present disclosure may include both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include but are not limited to those methods described below.

Scheme 1. General synthesis of 5-amino-2-thioaryl-(or thioheteroaryl)-3-methylpyridines

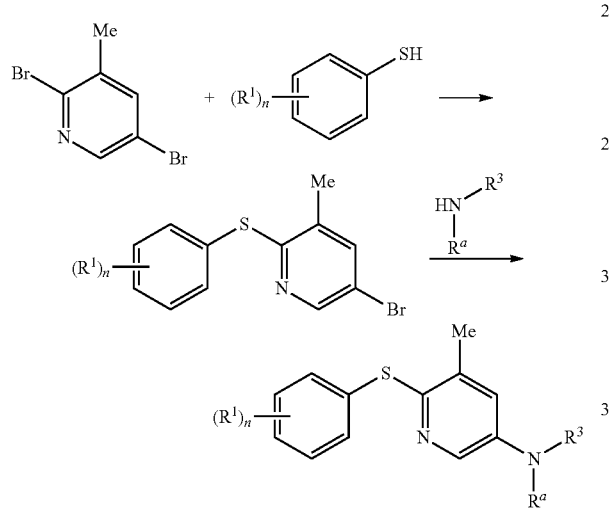

A general synthesis of 5-amino-2-thioaryl-(or thioheteroaryl)-3-methylpyridines is outlined in Scheme 1. 2,5-dibromo-3-methylpyridine can be coupled to a substituted aryl- or heteroaryl 1-thiol in the presence of a copper catalyst (e.g., CuI). The resulting thioether can then be coupled to a substituted primary or secondary amine to give a 5-amino-2-thioaryl-(or thioheteroaryl)-3-methylpyridines. Additional deprotection and/or functionalization steps can be required to produce the final compound.

Scheme 2. General Synthesis of 5-amino-2-aryl-(or heteroaryl)-3-methylpyridines

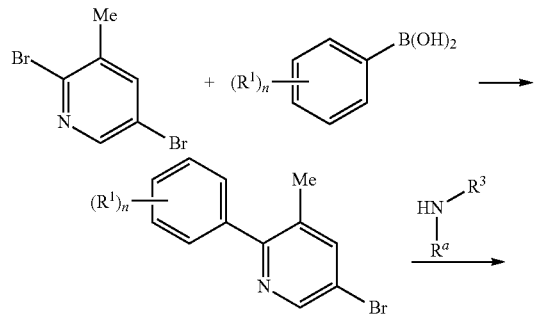

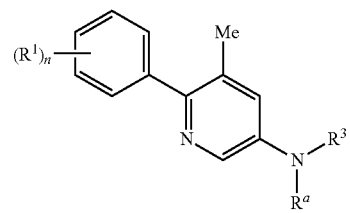

A general synthesis of 5-amino-2-aryl-(or heteroaryl)-3-methylpyridines is outlined in Scheme 2. 2,5-dibromo-3-methylpyridine can be coupled to a substituted aryl- or heteroaryl boronic acid in the presence of a palladium catalyst (e.g., Pd(dppf)Cl$_2$). The resulting biaryl intermediate can then be coupled to a substituted primary or secondary amine to give 5-amino-2-aryl-(or heteroaryl)-3-methylpyridines. Additional deprotection and/or functionalization steps can be required to produce the final compound.

Scheme 3. General Synthesis of Synthesis of 5-amino-2-aryl-(or heteroaryl)-6-methylhydroxy-3-methylpyridines and 5-amino-2-thioaryl- (orthioheteroaryl) -6-methylhydroxy-3-methylpyridines

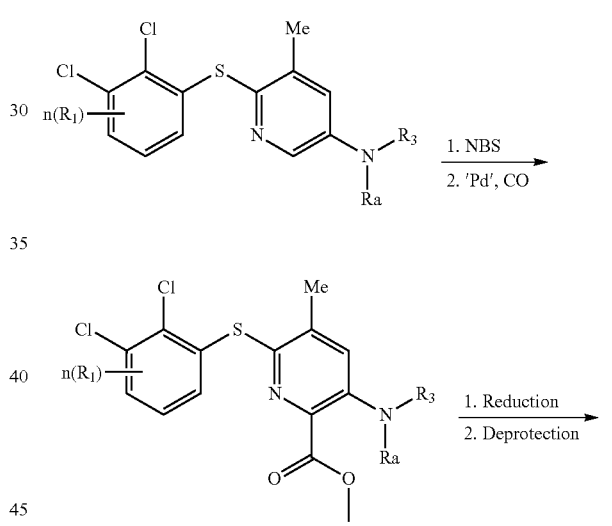

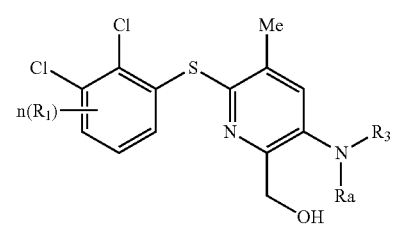

A general synthesis of 5-amino-2-thioaryl-(or thioheteroaryl)-6-methylhydroxy-3-methylpyridines is outlined in Scheme 3. 5-Amino-2-thioaryl-(or thioheteroaryl)-3-methylpyridines can be brominated followed by carbonylation. The resulting ester intermediate can be subsequently reduced to produce 5-amino-2-thioaryl-(orthioheteroaryl)-6-methylhydroxy-3-methylpyridines. Additional deprotection and/or functionalization steps can be required to produce the final compound.

Scheme 4. General Synthesis of Synthesis of
5-amino-2-aryl-(or heteroaryl)-6-methylhydroxy-3-
hydroxypyridines and 5-amino-2-thioaryl-
(or thioheteroaryl)-6-mythylhydroxy-3-hydroxypyridines

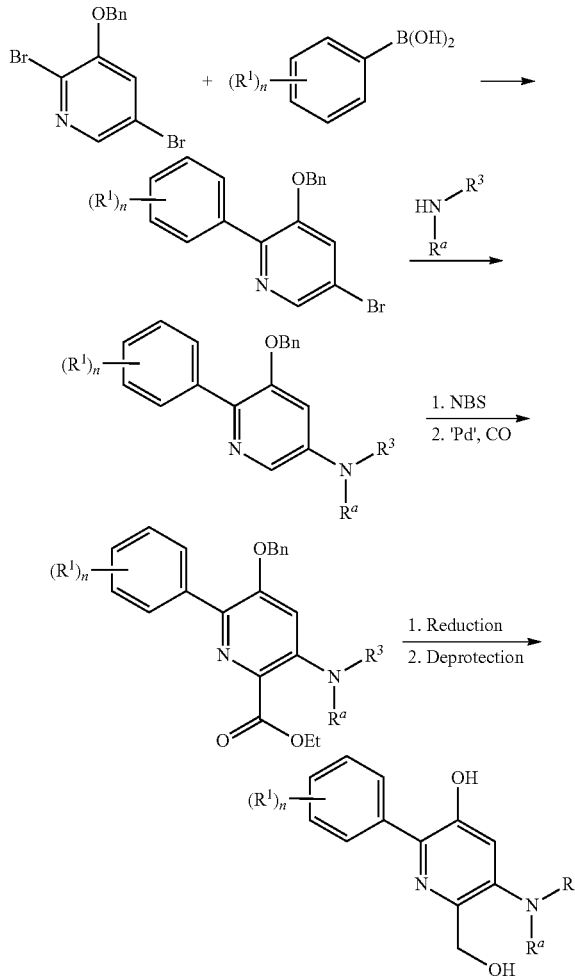

A general synthesis of Synthesis of 5-amino-2-aryl-(or heteroaryl)-6-methylhydroxy-3-hydroxypyridines and 5-amino-2-thioaryl-(or thioheteroaryl)-6-methylhydroxy-3-hydroxypyridines is outlined in Scheme 4. 2,5-dibromo-3-benzyloxypyridine can be coupled to a substituted aryl-(or heteroaryl) boronic acid or a substituted aryl- or heteroaryl 1-thiol. The resulting intermediate can then be coupled to a substituted primary or secondary amine to give a 5-amino-3-benzyloxy pyridines. Subsequent bromination, followed by carbonylation would result in 102 formation 5-amino-2-aryl-(or heteroaryl)-6-carboxyethyl-3-benzylhydroxy pyridines and 5-amino-2-thioaryl- (or thioheteroaryl)-6-carboxyethyl-3-benzylhydroxy pyridines. The resulting ester intermediate can be subsequently reduced. Additional deprotection and/or functionalization steps can be required to produce the final compound.

Methods of Using the Disclosed Compounds and Compositions

Methods and Uses of the Disclosure

Another aspect of the disclosure relates to methods of treating a disease associated with SHP2 modulation in a subject in need thereof. The methods may involve administering to a patient in need of treatment for diseases or disorders associated with SHP2 modulation an effective amount of one or more compounds of the present disclosure (e.g., compounds of Formula I, II, III, I-X, I-Y, or I-Z, and pharmaceutically acceptable salts, prodrugs, solvates, hydrates, tautomers, or isomers thereof), or of one or more pharmaceutical compositions of the present disclosure. In some embodiments, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knockdown of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the disclosure is directed to a method of inhibiting SHP2. The method involves administering to a patient in need thereof an effective amount of one or more compounds of the present disclosure (e.g., compounds of Formula I, II, III, I-X, I-Y, or I-Z, and pharmaceutically acceptable salts, prodrugs, solvates, hydrates, tautomers, or isomers thereof), or of one or more pharmaceutical compositions of the present disclosure.

The present disclosure relates to compounds or compositions disclosed herein that are capable of modulating the activity of (e.g., inhibiting) SHP2. The present disclosure also relates to the therapeutic use of such compounds and compositions.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 10 nM to about 100 nM of a compound of the disclosure. In some embodiments, SHP2 is inhibited after treatment with 10 nM to 100 nM of a compound of the disclosure. In some embodiments, SHP2 is inhibited after treatment with less than 10 nM of a compound of the disclosure.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 1 nM to about 10 nM of a compound of the disclosure. In some embodiments, SHP2 is inhibited after treatment with about 10 nM to about 100 nM of a compound of the disclosure. In some embodiments, SHP2 is inhibited after treatment with about 100 nM to about 10 µM of a compound of the disclosure.

Another aspect of the present disclosure relates to a one or more compounds of the present disclosure (e.g., compounds of Formula I, II, III, I-X, I-Y, or I-Z, and pharmaceutically acceptable salts, prodrugs, solvates, hydrates, tautomers, or isomers thereof), or one or more compositions of the present disclosure for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of one or more compounds of the present disclosure (e.g., compounds of Formula I, II, III, I-X, I-Y, or I-Z, and pharmaceutically acceptable salts, prodrugs, solvates, hydrates, tautomers, or isomers thereof), in the manufacture of a medicament for treating or preventing a disease. In some embodiments, the disease is associated with SHP2 modulation.

In another aspect, the present disclosure relates to one or more compounds of the present disclosure (e.g., compounds of Formula I, II, III, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

In one aspect, the present disclosure relates to one or more compositions comprising one or more compounds of the present disclosure (e.g., compounds of Formula I, II, III, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

Pharmaceutical Compositions and Modes of Administration of the Disclosure

Another aspect of the present disclosure relates to pharmaceutical compositions comprising one or more compounds of the present disclosure and a pharmaceutically acceptable carrier. The pharmaceutically acceptable carrier can further include an excipient, diluent, or surfactant.

Compositions of the disclosure can be prepared according to conventional mixing, granulating or coating methods, respectively, and the present pharmaceutical compositions can contain from about 0.1% to about 99%, from about 5% to about 90%, or from about 1% to about 20% of one or more of the disclosed compounds by weight or volume.

Administration of the disclosed compounds and compositions may be accomplished via any mode of administration for therapeutic agents. These modes may include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions may include tablets and gelatin capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more of the disclosed compounds are dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more disclosed compounds or compositions can be also formulated as a suppository that can be prepared from fatty emulsions or suspensions; using polyalkylene glycols such as propylene glycol, as the carrier.

One or more disclosed compounds or compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

One or more disclosed compounds or compositions can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the one or more disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In some embodiments, one or more disclosed compounds are not covalently bound to a polymer, e.g., a polycarboxylic acid polymer, or a polyacrylate.

One or more disclosed compounds or compositions can be delivered by parental administration. Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Dosage Regimens of the Disclosure

The dosage regimen utilizing one or more disclosed compounds or compositions may be selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, may range from about 0.5 mg to about 5000 mg of the disclosed compounds as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compounds, or, in a range of from one amount to another amount in the list of doses. In some embodiments, the compositions are in the form of a tablet that can be scored.

If desired, the effective daily dose of one or more compounds or compositions of this disclosure may be administered as one, two, three, four, five, six, or more sub-doses administered separately at appropriate intervals throughout the day, optionally, in unit dosage forms. In some embodiments of this disclosure, the one or more compounds or compositions of this disclosure, or mixtures thereof, may be administered two or three times daily. In some embodiments, the one or more compounds or compositions of this disclosure will be administered once daily.

In some embodiments, one or more compounds or compositions described herein may be used alone or together or conjointly administered, or used in combination, with another type of therapeutic agent. Conjoint administration or used in combination may refer to any form of administration of two or more different therapeutic compounds or compositions such that the second compound or composition is administered while the previously administered therapeutic compound or composition is still effective in the body. For example, the different therapeutic compounds or compositions can be administered either in the same formulation or in a separate formulation, either simultaneously, sequentially, or by separate dosing of the individual components of the treatment. In some embodiments, the different therapeutic compounds or compositions can be administered within one hour, 12 hours, 24 hours, 36 hours, 48 hours, 72 hours, or a week of one another. Thus, an individual who receives such treatment can benefit from a combined effect of different therapeutic compounds or compositions.

Kits

In some embodiments, this disclosure also provides a pharmaceutical package or kit comprising one or more containers filled with at least one compound or composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In some embodiments, the kit comprises at least two containers, at least one of which contains at least one compound or composition of this disclosure. In some embodiments, the kit contains at least two containers, and each of the at least two containers contains at least one compound or composition of this disclosure.

In some embodiments, the kit includes additional materials to facilitate delivery of the subject compounds and compositions. For example, the kit may include one or more of a catheter, tubing, infusion bag, syringe, and the like. In some embodiments, the compounds and compositions may be packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, methods, and uses described herein. This disclosure specifically contemplates any combination of the features of such compounds, compositions, methods, and uses (alone or in combination) with the features described for the various kits described in this section.

EXEMPLARY EMBODIMENTS

Some embodiments of this disclosure are Embodiment I, as follows:

Embodiment I-1

A compound of the Formula I:

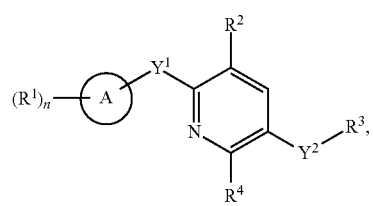

or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —C(O)N($R^a$)—, —N($R^a$)C(O)—, —S(O)$_2$N($R^a$)—, —N(R)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —NO$_2$, —CN, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, —C(O)$R^5$, or —CO$_2R^5$, wherein each alkyl, alkenyl, cycloalkenyl, alkynyl, or cycloalkyl is optionally substituted with one or more —OH, halogen, —NO$_2$, oxo, —CN, —$R^5$, —OR$^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —$R^5$, —OR$^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —NH$_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —$R^5$, —OR$^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —NH$_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —NH$_2$;

$R^4$ is —H, -D, or —$C_1$-$C_6$alkyl, wherein each alkyl is optionally substituted with one or more —OH, —NH$_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR$^7$, —SR$^7$, halogen, —$NR^7R^8$, —NO$_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-2

The compound of Embodiment I-1, wherein A is a 5- to 12-membered monocyclic or polycyclic cycloalkyl.

Embodiment I-3

The compound of Embodiment I-1, wherein A is a monocyclic or polycyclic heterocycloalkyl.

Embodiment I-4

The compound of Embodiment I-1, wherein A is monocyclic or polycyclic aryl.

Embodiment I-5

The compound of Embodiment I-1, wherein A is monocyclic or polycyclic heteroaryl.

Embodiment I-6

The compound of any one of Embodiments I-1 to 1-5, wherein $Y^1$ is —S—.

Embodiment I-7

The compound of any one of Embodiments I-1 to 1-5, wherein $Y^1$ is a direct bond.

Embodiment I-8

The compound of any one of Embodiments I-1 to 1-7, wherein $Y^2$ is —$NR^a$—.

Embodiment I-9

The compound of any one of Embodiments I-1 to 1-7, wherein $Y^2$ is —$(CR^a{}_2)_m$—.

Embodiment I-10

The compound of any one of Embodiments I-1 to 1-7, wherein $Y^2$ is —C(O)—.

Embodiment I-11

The compound of any one of Embodiments I-1 to 1-7, wherein $Y^2$ is —$C(R^a)_2$NH— or —$(CR^a{}_2)_mO$—.

Embodiment I-12

The compound of any one of Embodiments I-1 to 1-7, wherein $Y^2$ is —C(O)N($R^a$)—, —N($R^a$)C(O)—, —S(O)$_2$N($R^a$)—, —N($R^a$)S(O)$_2$—, —N($R^a$)C(S)—, or —C(S)N($R^a$)—.

Embodiment I-13

The compound of any one of Embodiments I-1 to 1-7, wherein $Y^2$ is —N($R^a$)C(O)N($R^a$)—, —N($R^a$)C(S)N($R^a$)—, —OC(O)N($R^a$)—, —N($R^a$)C(O)O—, or —C(O)N($R^a$)O—.

Embodiment I-14

The compound of any one of Embodiments I-1 to 1-7, wherein $Y^2$ is —C(O)O—, —OC(O)—, or —OC(O)O—.

Embodiment I-15

The compound of any one of Embodiments I-1 to 1-14, wherein $R^2$ is —$OR^b$.

Embodiment I-16

The compound of any one of Embodiments I-1 to 1-14, wherein $R^2$ is —$C_1$-$C_6$alkyl.

Embodiment I-17

The compound of any one of Embodiments I-1 to 1-14, wherein $R^2$ is —CN.

Embodiment I-18

The compound of any one of Embodiments I-1 to 1-14, wherein $R^2$ is —$C_2$-$C_6$alkenyl.

Embodiment I-19

The compound of any one of Embodiments I-1 to 1-14, wherein $R^2$ is —$C_4$-$C_8$cycloalkenyl.

Embodiment I-20

The compound of any one of Embodiments I-1 to 1-14, wherein $R^2$ is —$C_2$-$C_6$alkynyl.

Embodiment I-21

The compound of any one of Embodiments I-1 to 1-14, wherein $R^2$ is —$C_3$-$C_8$cycloalkyl.

Embodiment I-22

The compound of any one of Embodiments I-1 to 1-14, wherein $R^2$ is aryl.

Embodiment I-23

The compound of any one of Embodiments I-1 to 1-14, wherein $R^2$ is heterocyclyl containing 1-5 heteroatoms selected from the group consisting of N, S, P, and O.

Embodiment I-24

The compound of any one of Embodiments I-1 to 1-14, wherein $R^2$ is heteroaryl containing 1-5 heteroatoms selected from the group consisting of N, S, P, and O.

Embodiment I-25

The compound of any one of Embodiments I-1 to 1-24, wherein $R^a$ is —H.

Embodiment I-26

The compound of any one of Embodiments I-1 to 1-24, wherein $R^a$ is —OH.

Embodiment I-27

The compound of any one of Embodiments I-1 to 1-24, wherein $R^a$ is —$C_3$-$C_8$cycloalkyl.

Embodiment I-28

The compound of any one of Embodiments I-1 to 1-24, wherein $R^a$ is —$C_1$-$C_6$alkyl.

Embodiment I-29

The compound of any one of Embodiments I-1 to 1-28, wherein $R^b$ is —H.

Embodiment I-30

The compound of any one of Embodiments I-1 to 1-28, wherein $R^b$ is an optionally substituted $C_1$-$C_6$ alkyl.

Embodiment I-31

The compound of any one of Embodiments I-1 to 1-28, wherein $R^b$ is an optionally substituted —$C_3$-$C_8$cycloalkyl.

Embodiment I-32

The compound of any one of Embodiments I-1 to 1-28, wherein $R^b$ is an optionally substituted —$C_2$-$C_6$alkenyl.

Embodiment I-33

The compound of any one of Embodiments I-1 to 1-28, wherein $R^b$ is heterocyclyl containing 1-5 heteroatoms selected from the group consisting of N, S, P, and O.

Embodiment I-34

The compound of any one of Embodiments I-1 to 1-33, wherein $R^3$ is an optionally substituted —$C_1$-$C_6$alkyl.

Embodiment I-35

The compound of any one of Embodiments I-1 to 1-33, wherein $R^3$ is an optionally substituted 3- to 12-membered monocyclic or polycyclic heterocycle.

Embodiment I-36

The compound of any one of Embodiments I-1 to 1-33, wherein $R^3$ is an optionally substituted 3- to 12-membered monocyclic heterocycle.

Embodiment I-37

The compound of any one of Embodiments I-1 to I-33, wherein $R^3$ is an optionally substituted 5- to 12-membered polycyclic heterocycle.

Embodiment I-38

The compound of any one of Embodiments I-1 to I-33, wherein $R^3$ and $R^a$ together with the atom to which they are attached combine to form an optionally substituted 3- to 12-membered monocyclic heterocycle.

Embodiment I-39

The compound of any one of Embodiments I-1 to I-33, wherein $R^3$ and $R^a$ together with the atoms to which they are attached combine to form an optionally substituted 3- to 12-membered polycyclic heterocycle.

Embodiment I-40

The compound of any one of Embodiments I-1 to I-33, wherein $R^3$ and $R^a$ together with the atoms to which they are attached combine to form an optionally substituted 5- to 12-membered spiroheterocycle.

Embodiment I-41

The compound of any one of Embodiments I-1 to I-24 or 1-29 to 1-37, wherein $R^a$ and $R^4$ together with the atom to which they are attached combine to form an optionally substituted monocyclic or polycyclic 3- to 12-membered cycloalkyl.

Embodiment I-42

The compound of any one of Embodiments I-1 to I-24 or 1-29 to 1-37, wherein $R^a$ and $R^4$ together with the atom to which they are attached combine to form an optionally substituted monocyclic or polycyclic 3- to 12-membered heterocycle.

Embodiment I-43

A compound of the Formula I-A:

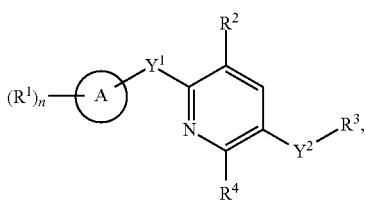

I-A or a pharmaceutically acceptable salt, prodrug, solvate, hydrate, tautomer, or isomer thereof, wherein:

A is aryl;

$Y^1$ is —S— or a direct bond;

$Y^2$ is —$NR^a$—, —$(CR^a_2)_m$—, —C(O)—, —$C(R^a)_2$NH—, —$(CR^a_2)_mO$—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, —C(O)$R^5$, or —CO$_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5S(O)_2NR^5R^6$, —$NR^5S(O)_2R^6$, —S(O)$NR^5R^6$, —S(O)$R^5$, —$NR^5S(O)NR^5R^6$, —$NR^5S(O)R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-44

A compound of the Formula I-B:

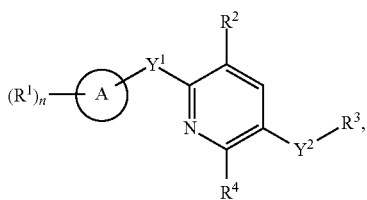

I-B or a pharmaceutically acceptable salt, prodrug, solvate, hydrate, tautomer, or isomer thereof, wherein:

A is heteroaryl;

Y¹ is —S— or a direct bond;

Y² is —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(R)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyridine ring and the bond on the right side of the Y² moiety is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —OR^b, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

R^b is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is —C₁-C₆alkyl or a 3- to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, or —NH₂;

R⁴ is —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-45

A compound of the Formula II:

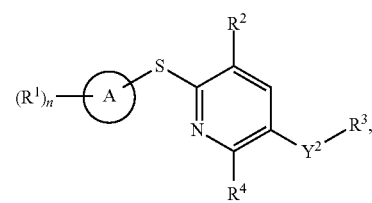

II or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-46

The compound Embodiment I-45, where the compound is of the Formula II-A:

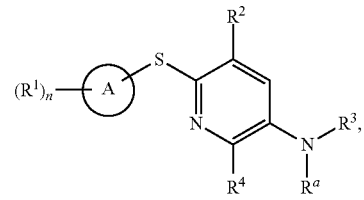

II-A or a pharmaceutically acceptable salt, prodrug, solvate, hydrate, tautomer, or isomer thereof.

Embodiment I-47

The compound of Embodiment I-46, where the compound is of the Formula II-A1:

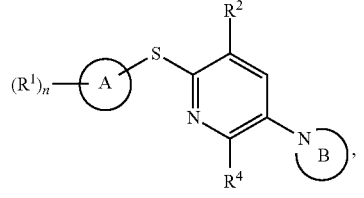

II-A1 or a pharmaceutically acceptable salt, prodrug, solvate, hydrate, tautomer, or isomer thereof, wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, or —$NH_2$.

Embodiment I-48

The compound of Embodiment I-46, wherein the compound is of the Formula II-A2:

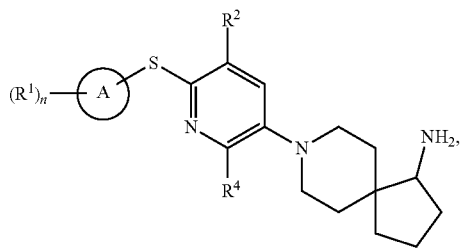

II-A2 or a pharmaceutically acceptable salt, prodrug, solvate, hydrate, tautomer, or isomer thereof.

Embodiment I-49

The compound of Embodiment I-46, wherein the compound is of the Formula II-A3:

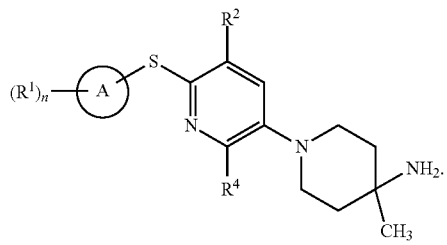

II-A3 or a pharmaceutically acceptable salt, prodrug, solvate, hydrate, tautomer, or isomer thereof.

Embodiment I-50

The compound of Embodiment I-45, wherein the compound is of the Formula II-B:

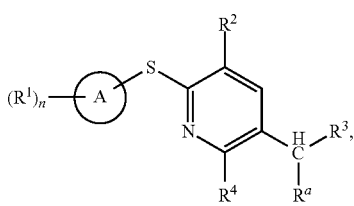

II-B or a pharmaceutically acceptable salt, prodrug, solvate, hydrate, tautomer, or isomer thereof.

Embodiment I-51

The compound of Embodiment I-50, wherein the compound is of the Formula II-B1:

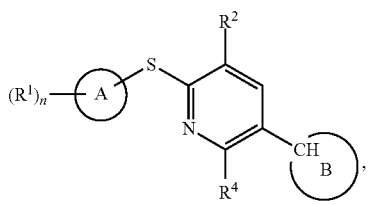

II-B1 or a pharmaceutically acceptable salt, prodrug, solvate, hydrate, tautomer, or isomer thereof, wherein:

B forms a 3- to 12-membered monocyclic or polycyclic heterocycle or a 5- to 12-membered spiroheterocycle along with the carbon atom to which it is attached, wherein the heterocycle or spiroheterocycle is optionally substituted with one or more —$C_1$-$C_6$alkyl, —OH, or —$NH_2$.

Embodiment I-52

The compound of Embodiment I-50, wherein the compound is of the Formula II-B2:

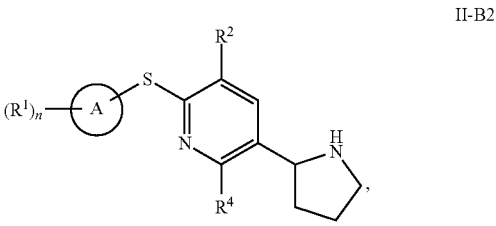

II-B2 or a pharmaceutically acceptable salt, prodrug, solvate, hydrate, tautomer, or isomer thereof.

Embodiment I-53

The compound of Embodiment I-50, wherein the compound is of the Formula II-B3:

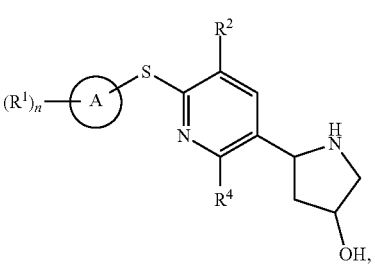

II-B3 or a pharmaceutically acceptable salt, prodrug, solvate, hydrate, tautomer, or isomer thereof.

Embodiment I-54

The compound of Embodiment I-50, wherein the compound is of the Formula II-B4:

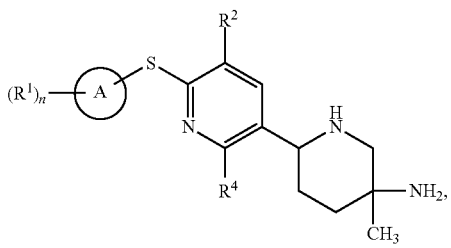

or a pharmaceutically acceptable salt, prodrug, solvate, hydrate, tautomer, or isomer thereof.

Embodiment I-55

The compound of Embodiment I-50, wherein the compound is of the Formula II-B5:

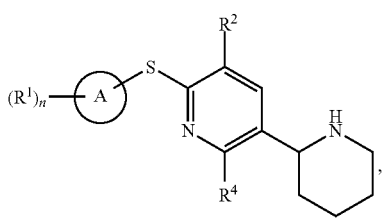

or a pharmaceutically acceptable salt, prodrug, solvate, hydrate, tautomer, or isomer thereof.

Embodiment I-56

The compound of Embodiment I-50, wherein the compound is of the Formula II-B6:

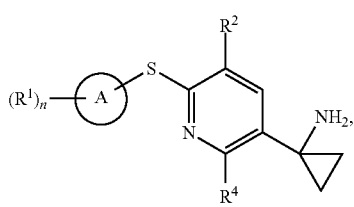

or a pharmaceutically acceptable salt, prodrug, solvate, hydrate, tautomer, or isomer thereof.

Embodiment I-57

The compound of Embodiment I-45, wherein the compound is of the Formula II-C:

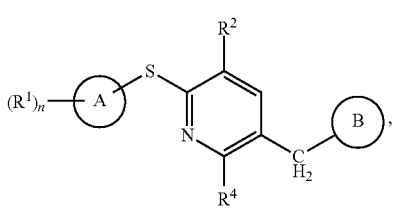

or a pharmaceutically acceptable salt, prodrug, solvate, hydrate, tautomer, or isomer thereof, wherein:

B forms a 3- to 12-membered monocyclic or polycyclic heterocycle, wherein the heterocycle or spiroheterocycle is optionally substituted with one or more —$C_1$-$C_6$alkyl, —OH, or —$NH_2$ Embodiment I-58

The compound of Embodiment I-57, wherein the compound is of the Formula II-C1:

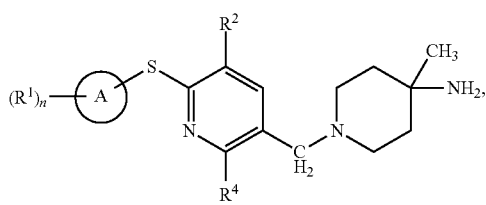

or a pharmaceutically acceptable salt, prodrug, solvate, hydrate, tautomer, or isomer thereof.

Embodiment I-59

The compound of Embodiment I-57, wherein the compound is of the Formula II-D:

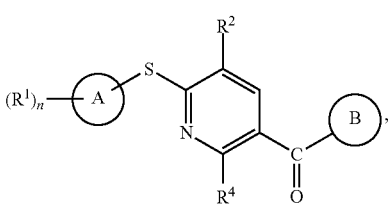

or a pharmaceutically acceptable salt, prodrug, solvate, hydrate, tautomer, or isomer thereof, wherein:

B forms a 3- to 12-membered monocyclic or polycyclic heterocycle, wherein the heterocycle or spiroheterocycle is optionally substituted with one or more —$C_1$-$C_6$alkyl, —OH, or —$NH_2$.

Embodiment I-60

The compound of Embodiment I-57, wherein the compound is of the Formula II-D1:

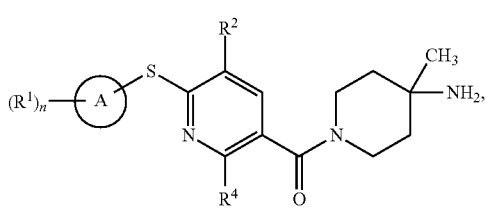

or a pharmaceutically acceptable salt, prodrug, solvate, hydrate, tautomer, or isomer thereof.

Embodiment I-61

The compound of Embodiment I-45, wherein the compound is of the Formula II-E:

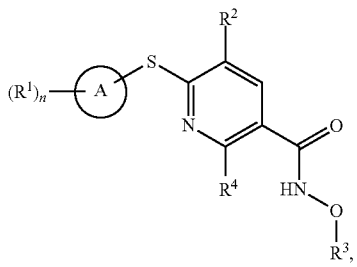

II-E or a pharmaceutically acceptable salt, prodrug, solvate, hydrate, tautomer, or isomer thereof.

Embodiment I-62

The compound of Embodiment I-45, wherein the compound is of the Formula II-F:

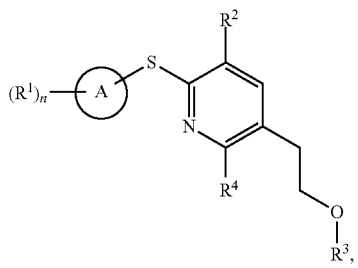

II-F or a pharmaceutically acceptable salt, prodrug, solvate, hydrate, tautomer, or isomer thereof.

Embodiment I-63

The compound of Embodiment I-45, wherein the compound is of the Formula II-G:

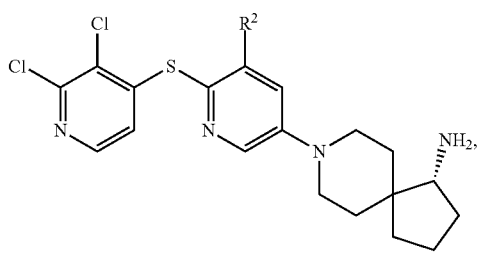

II-G or a pharmaceutically acceptable salt, prodrug, solvate, hydrate, tautomer, or isomer thereof, wherein $R^2$ is aryl or heteroaryl.

Embodiment I-64

A compound of the Formula III:

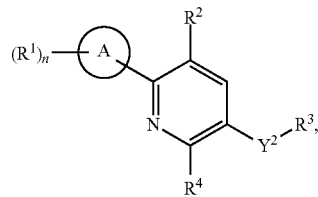

III or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^2$ is —$NR^a$—, —$(CR^a{}_2)_m$—, —C(O)—, —C($R^a$)$_2$NH—, —$(CR^a{}_2)_m$O—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyridine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, —C(O)$R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2$$NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is —H, -D, or —C$_1$-C$_6$alkyl, wherein each alkyl is optionally substituted with one or more —OH, —NH$_2$, halogen, or oxo; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-65

The compound of Embodiment I-64, wherein the compound is of the Formula III-A:

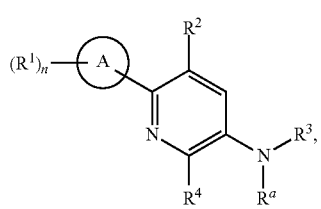

III-A or a pharmaceutically acceptable salt, prodrug, solvate, hydrate, tautomer, or isomer thereof.

Embodiment I-66

The compound of Embodiment I-65, wherein the compound is of the Formula III-A1:

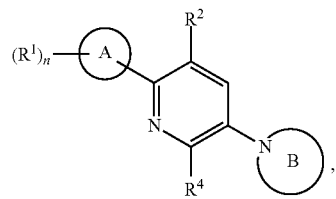

III-A1 or a pharmaceutically acceptable salt, prodrug, solvate, hydrate, tautomer, or isomer thereof, wherein B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —C$_1$-C$_6$alkyl, —OH, or —NH$_2$.

Embodiment I-67

The compound of Embodiment I-65, wherein the compound is of the Formula III-A2:

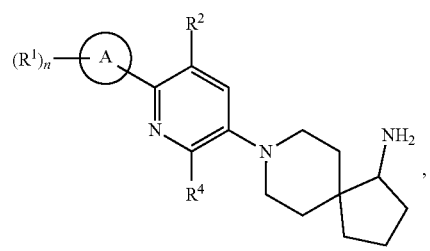

III-A2 or a pharmaceutically acceptable salt, prodrug, solvate, hydrate, tautomer, or isomer thereof.

Embodiment I-68

The compound of Embodiment I-65, wherein the compound is of the Formula III-A3:

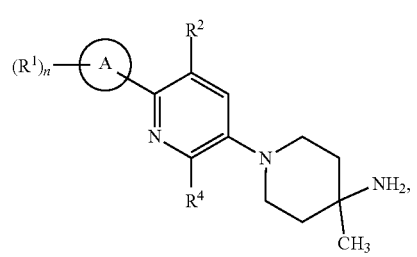

III-A3 or a pharmaceutically acceptable salt, prodrug, solvate, hydrate, tautomer, or isomer thereof.

Embodiment I-69

A compound selected from the group consisting of:

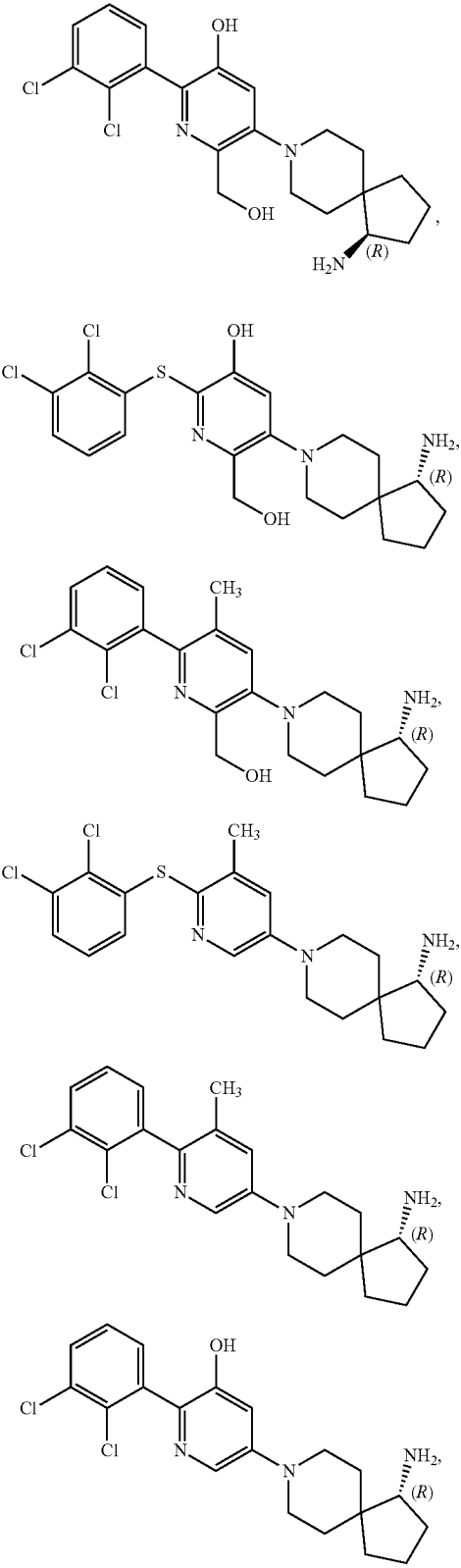

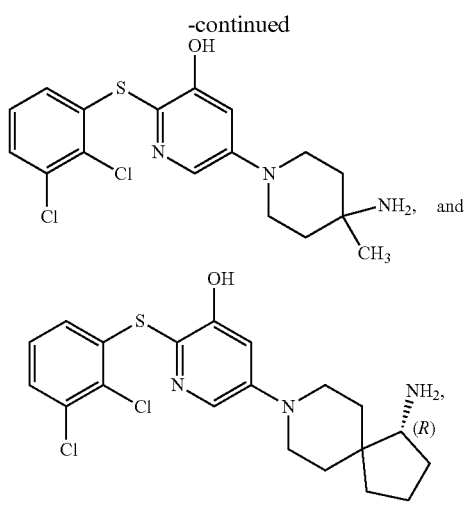

or a pharmaceutically acceptable salt, prodrug, solvate, hydrate, tautomer, or isomer thereof.

Embodiment I-70

A pharmaceutical composition comprising a compound of any one of Embodiments I-1 to 1-69 and a pharmaceutically acceptable carrier.

Embodiment I-71

A method of treating a disease associated with SHP2 modulation in a subject in need thereof, comprising administering to the subject an effective amount of a compound of any one of Embodiments I-1 to 1-69.

Embodiment I-72

The method of Embodiment I-71, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-73

A compound of any one of Embodiments I-1 to 1-69 for use in treating or preventing a disease associated with SHP2 modulation.

Embodiment I-74

Use of a compound of any one of Embodiments I-1 to 1-69 in the manufacture of a medicament for treating or preventing a disease associated with SHP2 modulation.

Embodiment I-75

A compound of the Formula I-X:

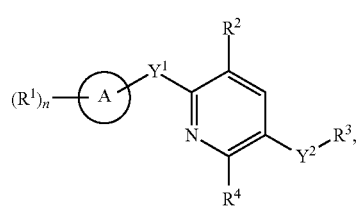

I-X or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

$R^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^3$ is —H, —C$_1$-C$_6$alkyl, or a 3- to 12-membered monocyclic or polycyclic heterocycle, wherein each alkyl or heterocycle is optionally substituted with one or more —C$_1$-C$_6$alkyl, —OH, or —NH$_2$; or $R^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

$R^4$ is —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or $R^a$ and $R^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-76

A compound of the Formula I-Y:

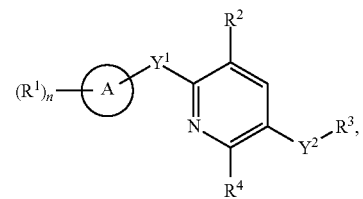

I-Y or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-

$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, Oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_n$OH, —$C_1$-$C_6$alkyl, —$CF_3$, —$CHF_2$, or —$CH_2F$;

$R^3$ is —H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$$NH_2$, —$COOR^b$, —$CONHR^b$, —$CONH(CH_2)_n$$COOR^b$, —$NHCOOR^b$, —$CF_3$, —$CHF_2$, or —$CH_2F$;

$R^4$ is —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$NH(CH_2)_n$OH, —$C(O)NH(CH_2)_n$OH, —$C(O)NH(CH_2)_n$$R^b$, —$C(O)R^b$, $NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-77

A compound of the Formula I-Z:

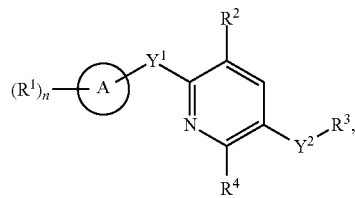

I-Z or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S—, a direct bond, —NH—, —$S(O)_2$—, —$S(O)_2$—NH—, —$C(=CH_2)$—, —CH—, or —$S(O)$—;

$Y^2$ is —$NR^a$—, —$(CR^a{}_2)_m$—, —$C(O)$—, —$C(R^a)_2$NH—, —$(CR^a{}_2)_m$O—, —$C(O)N(R^a)$—, —$N(R^a)C(O)$—, —$S(O)_2N(R^a)$—, —$N(R)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, or —$OC(O)O$—; wherein the bond on the left side of $Y^2$, as drawn, is bound to the pyridine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

R² is —ORᵇ, —CN, —C₁-C₆alkyl, —C₂-C₆alkenyl, —C₄-C₈cycloalkenyl, —C₂-C₆alkynyl, —NH₂, halogen, —C(O)ORᵇ, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, heteroaryl, —(CH₂)ₙOH, —C₁-C₆alkyl, —CF₃, —CHF₂, or —CH₂F;

R³ is —H, —C₁-C₆alkyl, a 3- to 12-membered monocyclic or polycyclic heterocycle, C₃-C₈cycloalkyl, or —(CH₂)ₙ—Rᵇ, wherein each alkyl, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, —OH, —NH₂, heteroaryl, heterocyclyl, —(CH₂)ₙNH₂, —COORᵇ, —CONHRᵇ, —CONH(CH₂)ₙCOORᵇ, —NHCOORᵇ, —CF₃, —CHF₂, or —CH₂F;

R⁴ is —H, -D, —C₁-C₆alkyl, —NH—NHR⁵, —NH—OR⁵, —O—NR⁵R⁶, —NHR⁵, —OR⁵, —NHC(O)R⁵, —NHC(O)NHR⁵, —NHS(O)₂R⁵, —NHS(O)₂NHR⁵, —S(O)₂OH, —C(O)OR⁵, —NH(CH₂)ₙOH, —C(O)NH(CH₂)ₙOH, —C(O)NH(CH₂)ₙRᵇ, —C(O)Rᵇ, NH₂, —OH, —CN, —C(O)NR⁵R⁶, —S(O)₂NR⁵R⁶, C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH₂, halogen, or oxo; wherein each aryl or heteroaryl is optionally substituted with one or more —OH, —NH₂, or halogen; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo; wherein the heterocycle optionally comprises —S(O)₂— in the heterocycle;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Some embodiments of this disclosure are Embodiment II, as follows:

Embodiment II-1

A compound of Formula I-Y1:

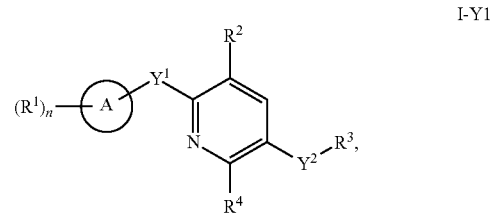

I-Y1 or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

Y¹ is —S— or a direct bond;

Y² is —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyridine ring and the bond on the right side of the Y² moiety, as drawn, is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, —NO₂, oxo, —CN, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is —OH, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is —H, —C$_1$-C$_6$alkyl, a 3- to 12-membered monocyclic or polycyclic heterocycle, —C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^4$ is —H, -D, —C$_1$-C$_6$alkyl, —NH—NHR$^5$, —NH—OR$^5$, —O—NR$^5$R$^6$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —OH, —CN, —C(O)NR$^5$R$^6$, —S(O)$_2$ NR$^5$R$^6$, C$_3$-C$_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment II-2

The compound of Embodiment II-1, wherein Y$^2$ is —NR$^a$—.

Embodiment II-3

The compound of Embodiment II-1, wherein Y$^2$ is —(CR$^a_2$)$_m$—.

Embodiment II-4

The compound of any one of Embodiments II-1 to II-3, wherein Y$^1$ is —S—.

Embodiment II-5

The compound of any one of Embodiments II-1 to II-3, wherein Y$^1$ is a direct bond.

Embodiment II-6

The compound of any one of Embodiments II-1 to II-5, wherein R$^3$ is an optionally substituted 3- to 12-membered monocyclic or polycyclic heterocycle.

Embodiment II-7

The compound of Embodiment II-6, wherein R$^3$ is an optionally substituted 3- to 12-membered monocyclic heterocycle.

Embodiment II-8

The compound of Embodiment II-6, wherein R$^3$ is an optionally substituted 3- to 12-membered polycyclic heterocycle.

Embodiment II-9

The compound of any one of Embodiments II-1 to II-8, wherein R$^a$ is —H.

Embodiment II-10

The compound of any one of Embodiments II-1 to II-5, wherein R$^3$ and R$^a$ together with the atom to which they are attached combine to form a 3- to 12-membered monocyclic heterocycle, which is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

Embodiment II-11

The compound of any one of Embodiments II-1 to II-5, wherein R$^3$ and R$^a$ together with the atoms to which they are attached combine to form a 3- to 12-membered polycyclic heterocycle, which is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

Embodiment II-12

The compound of any one of Embodiments II-1 to II-5, wherein R$^3$ and R$^a$ together with the atoms to which they are attached combine to form a 5- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

Embodiment II-13

The compound of Embodiment II-12, wherein $R^3$ and $R^a$ together with the atoms to which they are attached combine to form a 10- to 12-membered spiroheterocycle, which is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$.

Embodiment II-14

The compound of any one of Embodiments II-10 to II-13, wherein $R^b$ is —H.

Embodiment II-15

The compound of any one of Embodiments II-10 to II-13, wherein $R^b$ is an optionally substituted —$C_1$-$C_6$alkyl.

Embodiment II-16

The compound of any one of Embodiments II-10 to II-13, wherein $R^b$ is an optionally substituted —$C_3$-$C_8$cycloalkyl.

Embodiment II-17

The compound of any one of Embodiments II-10 to II-13, wherein $R^b$ is an optionally substituted —$C_2$-$C_6$alkenyl.

Embodiment II-18

The compound of Embodiment II-1 or 11-2, wherein the compound is a compound of Formula I-Y6:

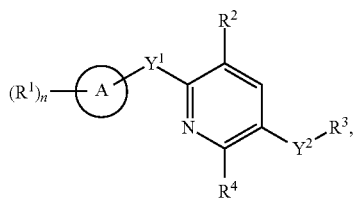

I-Y6 or a pharmaceutically acceptable salt, prodrug, solvate, hydrate, tautomer, or isomer thereof, wherein:
A is a 5- to 12-membered monocyclic or polycyclic aryl or heteroaryl;
$Y^1$ is —S—;
$Y^2$ is —$NR^a$—; wherein the bond on the left side of $Y^2$, as drawn, is bound to the pyridine ring and the bond on the right side of the $Y^2$ moiety, as drawn, is bound to $R^3$;
$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, —$CF_3$, —$CHF_2$, or —$CH_2F$;
$R^1$ is independently, at each occurrence, —H, —$C_1$-$C_6$alkyl, —OH, halogen, or —$NR^5R^6$;
$R^2$ is —$C_1$-$C_6$alkyl or —OH;
$R^4$ is —H, —$C_1$-$C_6$alkyl, —$C_1$-$C_6$haloalkyl, —$C_1$-$C_6$hydroxyalkyl, —$CH_2OH$, —$CF_2OH$, or —CHFOH, wherein alkyl is optionally substituted with one or more —OH, —$NH_2$, halogen, or oxo; or
$R^5$ and $R^6$ are each independently, at each occurrence, —H or —$C_1$-$C_6$alkyl; and
n is independently, at each occurrence, 1, 2, 3, 4, 5, 6, 7, 8, 9, or 10.

Embodiment II-19

The compound of Embodiment II-1 or 11-2, wherein the compound is a compound of Formula I-Y7:

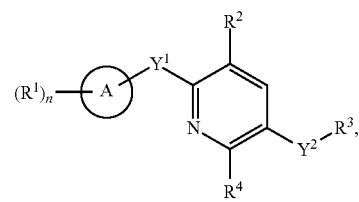

I-Y7 or a pharmaceutically acceptable salt, prodrug, solvate, hydrate, tautomer, or isomer thereof, wherein:
A is a 5- to 12-membered monocyclic or polycyclic aryl or heteroaryl;
$Y^1$ is a direct bond;
$Y^2$ is —$NR^a$—; wherein the bond on the left side of $Y^2$, as drawn, is bound to the pyridine ring and the bond on the right side of the $Y^2$ moiety, as drawn, is bound to $R^3$;
$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, —$CF_3$, —$CHF_2$, or —$CH_2F$;
$R^1$ is independently, at each occurrence, —H, —$C_1$-$C_6$alkyl, —OH, halogen, or —$NR^5R^6$;
$R^2$ is —$C_1$-$C_6$alkyl or —OH;
$R^4$ is —H, —$C_1$-$C_6$alkyl, —$C_1$-$C_6$haloalkyl, —$C_1$-$C_6$hydroxyalkyl, —$CH_2OH$, —$CF_2OH$, or —CHFOH, wherein alkyl is optionally substituted with one or more —OH, —$NH_2$, halogen, or oxo; or
$R^5$ and $R^6$ are each independently, at each occurrence, —H or —$C_1$-$C_6$alkyl; and
n is independently, at each occurrence, 1, 2, 3, 4, 5, 6, 7, 8, 9, or 10.

Embodiment II-20

The compound of Embodiment II-18 or II-19, wherein $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, —$CF_3$, —$CHF_2$, or —$CH_2F$.

Embodiment II-21

The compound of Embodiment II-18 or II-19, wherein $R^3$ and $R^a$ together with the atoms to which they are attached combine to form a 3- to 12-membered polycyclic heterocycle, which is optionally substituted with one or more —$C_1$-$C_6$alkyl, —OH, —$NH_2$, —$CF_3$, —$CHF_2$, or —$CH_2F$.

Embodiment II-22

The compound of Embodiment II-18 or II-19, wherein $R^3$ and $R^a$ together with the atoms to which they are attached combine to form a 5- to 12-membered spiroheterocycle, which is optionally substituted with one or more —$C_1$-$C_6$alkyl, —OH, —$NH_2$, —$CF_3$, —$CHF_2$, or —$CH_2F$.

Embodiment II-23

The compound of Embodiment II-22, wherein $R^3$ and $R^a$ together with the atoms to which they are attached combine to form a 10- to 12-membered spiroheterocycle, which is optionally substituted with one or more —$C_1$-$C_6$alkyl, —OH, —$NH_2$, —$CF_3$, —$CHF_2$, or —$CH_2F$.

Embodiment II-24

The compound of any one of Embodiments II-1 to II-17, wherein A is a monocyclic or polycyclic cycloalkyl.

Embodiment II-25

The compound of any one of Embodiments II-1 to II-17, wherein A is a monocyclic or polycyclic heterocycloalkyl.

Embodiment II-26

The compound of any one of Embodiments II-1 to II-23, wherein A is a monocyclic or polycyclic aryl.

Embodiment II-27

The compound of any one of Embodiments II-1 to II-23, wherein A is a monocyclic or polycyclic heteroaryl.

Embodiment II-28

The compound of Embodiment II-26, wherein A is phenyl.

Embodiment II-29

The compound of Embodiment II-27, wherein A is pyridinyl.

Embodiment II-30

The compound of any one of Embodiments II-1 to II-29, wherein n is 1 or 2.

Embodiment II-31

The compound of any one of Embodiments II-1 to II-30, wherein $R^1$ is independently, at each occurrence, —H, —$C_1$-$C_6$alkyl, halogen, or —$NR^5R^6$.

Embodiment II-32

The compound of any one of Embodiments II-1 to II-31, wherein $R^1$ is independently, at each occurrence, —H, methyl, fluoro, chloro, or —$NH_2$.

Embodiment II-33

The compound of any one of Embodiments II-1 to II-32, wherein $R^2$ is —OH.

Embodiment II-34

The compound of any one of Embodiments II-1 to II-32, wherein $R^2$ is —$C_1$-$C_6$alkyl.

Embodiment II-35

The compound of Embodiment II-34, wherein $R^2$ is methyl.

Embodiment II-36

The compound of any one of Embodiments II-1 to II-35, wherein $R^4$ is —$C_1$-$C_6$alkyl, which is optionally substituted with one or more —OH, —$NH_2$, halogen, or oxo.

Embodiment II-37

The compound of Embodiment II-36, wherein $R^4$ is —$C_1$-$C_6$alkyl, which is substituted with one or more —OH.

Embodiment II-38

The compound of Embodiment II-37, wherein $R^4$ is —$CH_2$—OH.

Embodiment II-39

The compound of any one of Embodiments II-1 to II-35, wherein $R^4$ is —H.

Embodiment II-40

The compound of any one of Embodiments II-1 to II-36, wherein $R^4$ is —$CF_2OH$ or —CHFOH.

Embodiment II-41

A compound, or a pharmaceutically acceptable salt, prodrug, solvate, hydrate, tautomer, or isomer thereof, selected from the group consisting of:

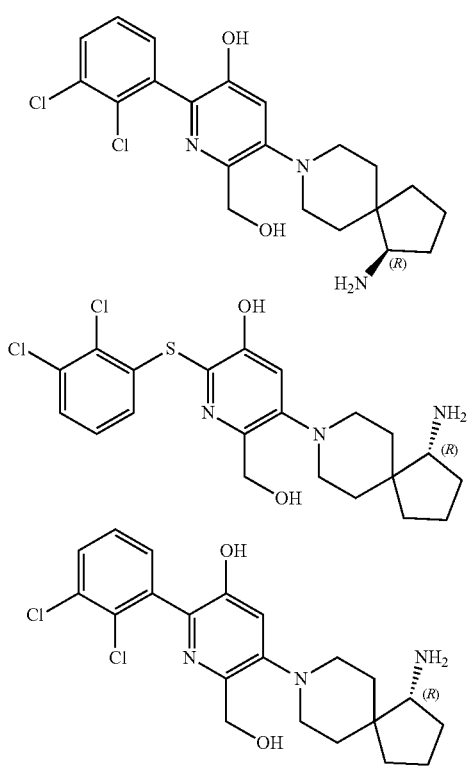

-continued
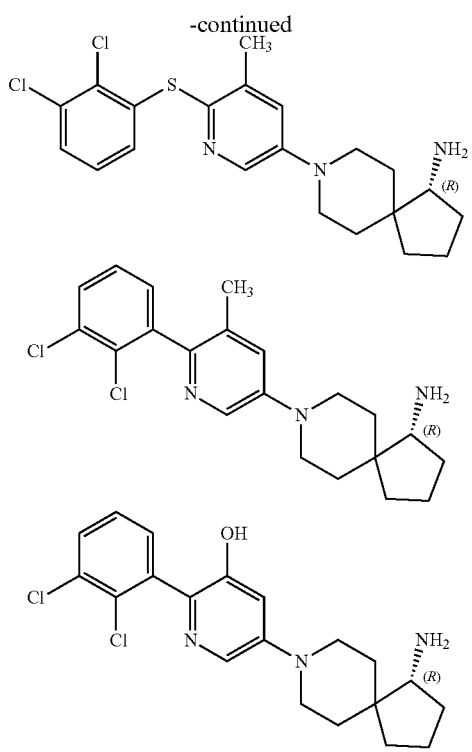
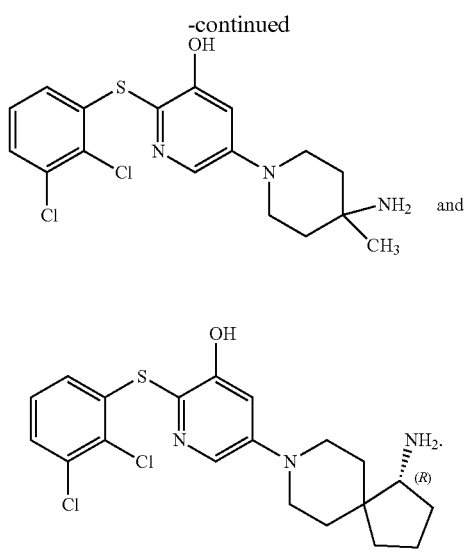
Embodiment II-42
A compound, or a pharmaceutically acceptable salt, prodrug, solvate, hydrate, tautomer, or isomer thereof, selected from the group consisting of:
| Example | |
|---|---|
| 1 | 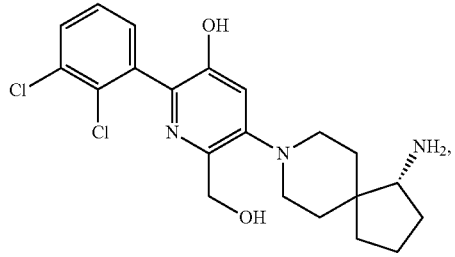 [SMILES: N[C@@H]1CCCC12CCN(c1cc(O)c(-c3cccc(Cl)c3Cl)nc1CO)CC2] |
| 2 | 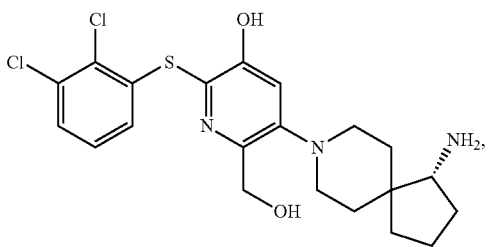 [SMILES: N[C@@H]1CCCC12CCN(c1cc(O)c(Sc3cccc(Cl)c3Cl)nc1CO)CC2] |
| 3 | 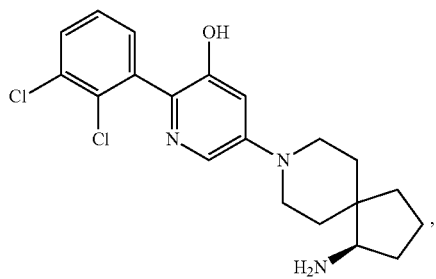 [SMILES: N[C@@H]1CCCC12CCN(c1cnc(-c3cccc(Cl)c3Cl)c(O)c1)CC2 ; ","] |

| Example | |
|---|---|
| 4 | 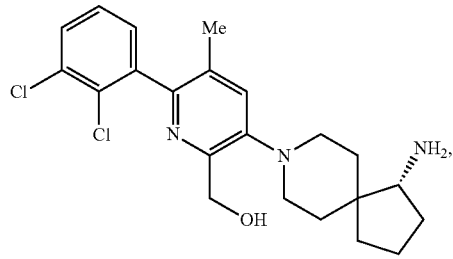 [SMILES: Cc1cc(N2CCC3(CCC[C@H]3N)CC2)c(CO)nc1-c1cccc(Cl)c1Cl] |
| 5 | 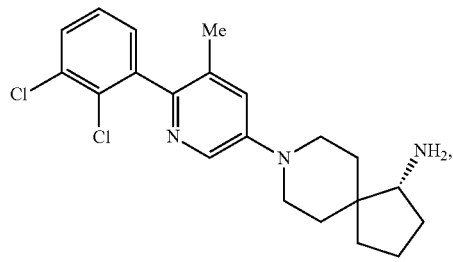 [SMILES: Cc1cc(N2CCC3(CCC[C@H]3N)CC2)cnc1-c1cccc(Cl)c1Cl] |
| 6 | 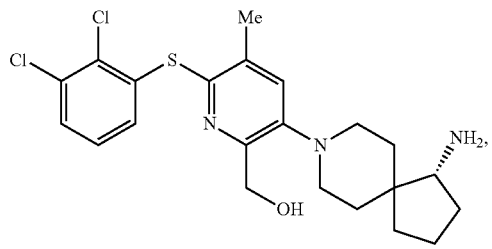 [SMILES: Cc1cc(N2CCC3(CCC[C@H]3N)CC2)c(CO)nc1Sc1cccc(Cl)c1Cl] |
| 7 | 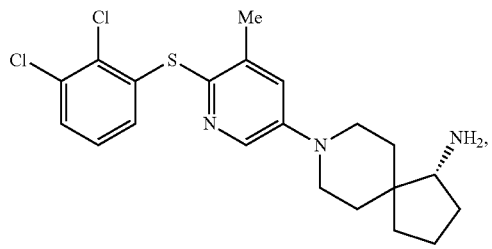 [SMILES: Cc1cc(N2CCC3(CCC[C@H]3N)CC2)cnc1Sc1cccc(Cl)c1Cl] |
| 8 | 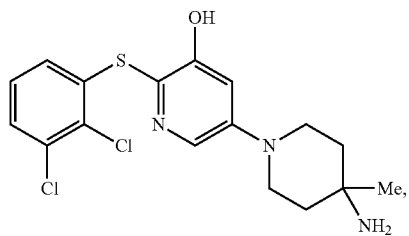 [SMILES: CC1(N)CCN(c2cnc(Sc3cccc(Cl)c3Cl)c(O)c2)CC1] |
| 9 | 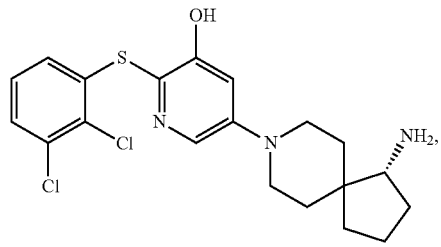 [SMILES: N[C@@H]1CCCC12CCN(c1cnc(Sc3cccc(Cl)c3Cl)c(O)c1)CC2] |

-continued
| Example | |
|---|---|
| 10 | 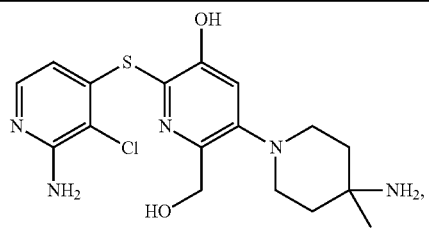 |
| 11 | 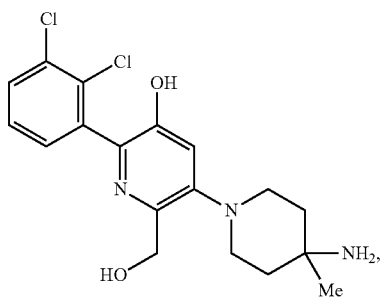 [SMILES: CC1(N)CCN(c2cc(O)c(-c3cccc(Cl)c3Cl)nc2CO)CC1] |
| 12 | 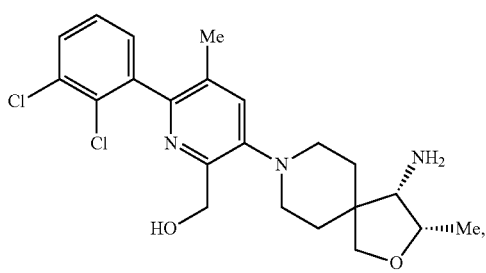 [SMILES: Cc1cc(N2CCC3(CC2)CO[C@@H](C)[C@H]3N)c(CO)nc1-c1cccc(Cl)c1Cl] |
| 13 | 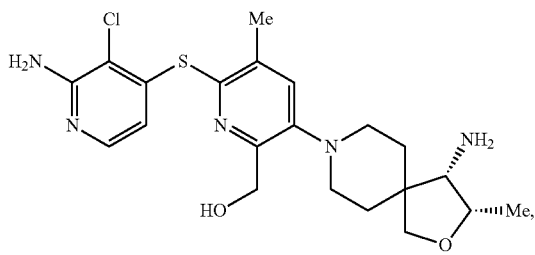 [SMILES: Cc1cc(N2CCC3(CC2)CO[C@@H](C)[C@H]3N)c(CO)nc1Sc1ccnc(N)c1Cl] |
| 14 | 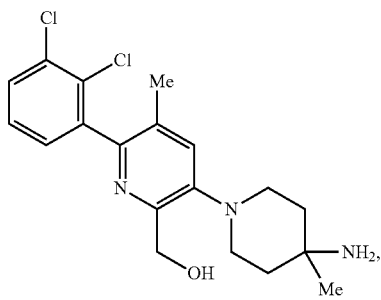 [SMILES: Cc1cc(N2CCC(C)(N)CC2)c(CO)nc1-c1cccc(Cl)c1Cl] |
| 15 | 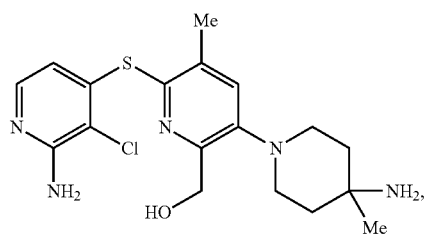 [SMILES: Cc1cc(N2CCC(C)(N)CC2)c(CO)nc1Sc1ccnc(N)c1Cl] |

-continued

| Example | |
|---|---|
| 16 | 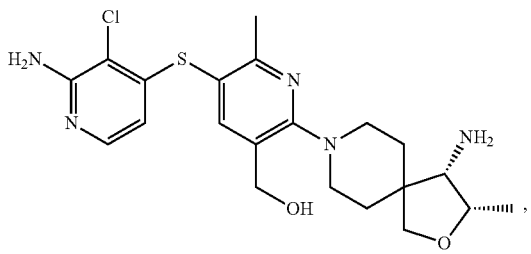 [SMILES: Cc1nc(N2CCC3(CC2)CO[C@@H](C)[C@H]3N)c(CO)cc1Sc1ccnc(N)c1Cl ; ","] |
| 17 | 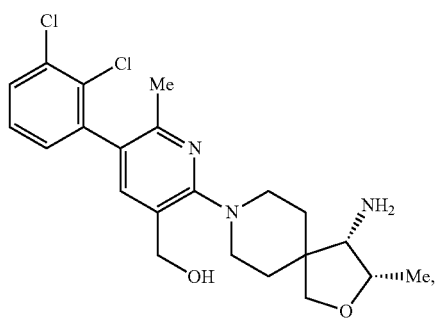 [SMILES: Cc1nc(N2CCC3(CC2)CO[C@@H](C)[C@H]3N)c(CO)cc1-c1cccc(Cl)c1Cl] |
| 18 | 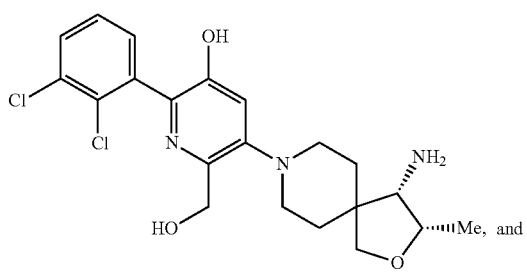 [SMILES: C[C@@H]1OCC2(CCN(c3cc(O)c(-c4cccc(Cl)c4Cl)nc3CO)CC2)[C@@H]1N ; "and"] |
| 19 | 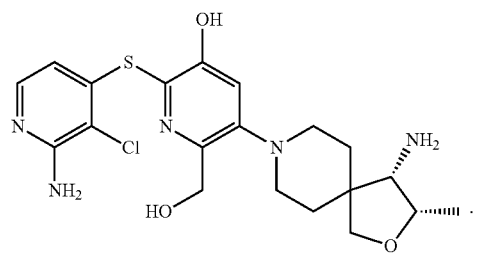 |

Embodiment II-43

A pharmaceutical composition comprising a compound of any one of Embodiments II-1 to II-42, or a pharmaceutically acceptable salt, prodrug, solvate, hydrate, tautomer, or isomer thereof, and a pharmaceutically acceptable carrier.

Embodiment II-44

A method of treating a disease associated with SHP2 modulation in a subject in need thereof, comprising administering to the subject an effective amount of a compound of any one of Embodiments II-1 to II-42, or a pharmaceutically acceptable salt, prodrug, solvate, hydrate, tautomer, or isomer thereof.

Embodiment II-45

The method of Embodiment II-44, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-46

A compound of any one of Embodiments II-1 to II-42, or a pharmaceutically acceptable salt, prodrug, solvate, hydrate, tautomer, or isomer thereof, for use as a medicament.

Embodiment II-47

A compound of any one of Embodiments II-1 to II-42, or a pharmaceutically acceptable salt, prodrug, solvate,

123 hydrate, tautomer, or isomer thereof, for use in treating or preventing a disease associated with SHP2 modulation.

Embodiment II-48

Use of a compound of any one of Embodiments II-1 to 11-42, or a pharmaceutically acceptable salt, prodrug, solvate, hydrate, tautomer, or isomer thereof, in the manufacture of a medicament for treating or preventing a disease associated with SHP2 modulation.

Embodiment II-49

A method of treating a disease associated with SHP2 modulation in a subject in need thereof, comprising administering to the subject an effective amount of a pharmaceutical composition of Embodiment II-43.

Embodiment II-50

The method of Embodiment II-49, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-51

A pharmaceutical composition of Embodiment II-43 for use as a medicament.

Embodiment II-52

A pharmaceutical composition of Embodiment II-43 for use in treating or preventing a disease associated with SHP2 modulation.

Embodiment II-53

Use of a pharmaceutical composition of Embodiment II-43 in the manufacture of a medicament for treating or preventing a disease associated with SHP2 modulation.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

| | |
|---|---|
| CH₂Cl₂, DCM | Methylene chloride, Dichloromethane |
| CH₃CN, MeCN | Acetonitrile |
| CuI | Copper (I) iodide |
| DIPEA | Diisopropylethyl amine |
| DMF | N,N-Dimethylformamide |
| EtOAc | Ethyl acetate |
| hr | hour |
| H₂O | Water |

-continued

| | |
|---|---|
| HCl | Hydrochloric acid |
| K₃PO₄ | Potassium phosphate (tribasic) |
| MeOH | Methanol |
| Na₂SO₄ | Sodium sulfate |
| NMP | N-methyl pyrrolidone |
| Pd(dppf)Cl₂ | [1,1'-Bis(diphenylphosphino)ferrocene]dichloropalladium(II) |

Example 1. Synthesis of 5-[(4R)-4-amino-8-azaspiro[4.5]decan-8-yl]-2-(2,3-dichlorophenyl)-6-(hydroxymethyl)pyridin-3-ol

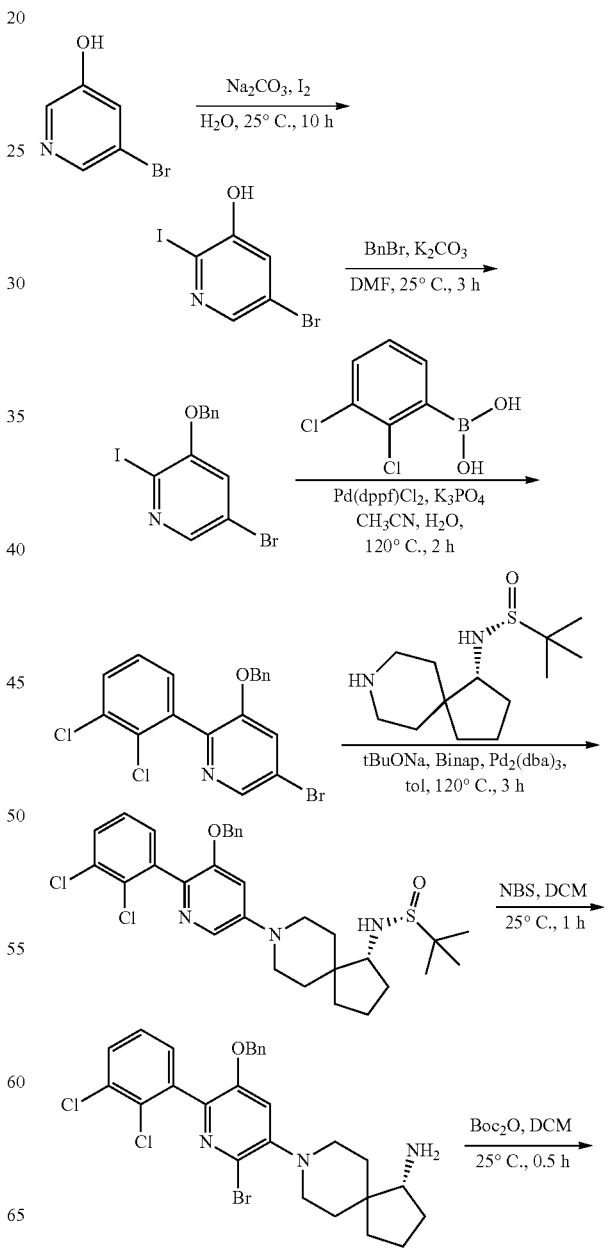

-continued

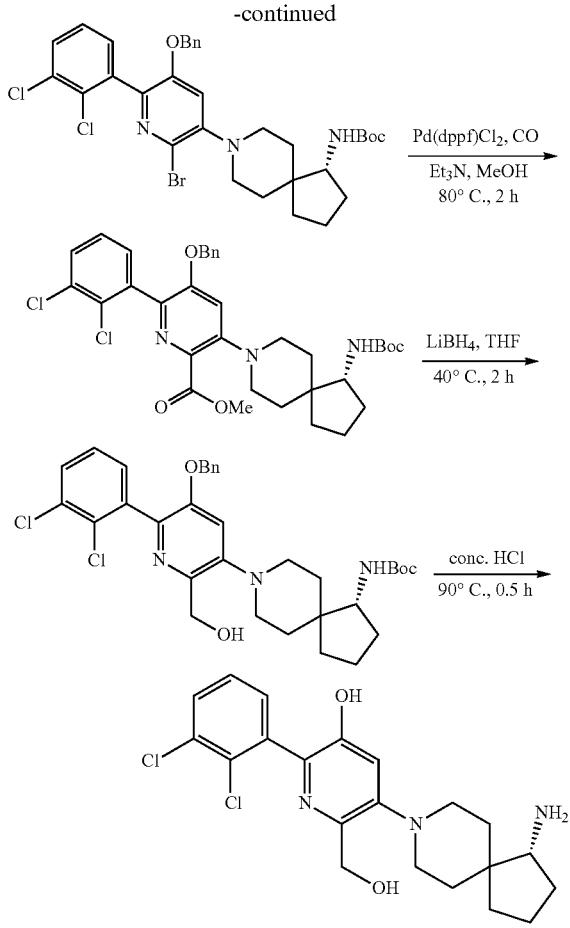

Step 1

To a solution of 5-bromopyridin-3-ol (24 g, 137.9 mmol) in H$_2$O (300 mL) was added Na$_2$CO$_3$ (29.2 g, 275.86 mmol) and I$_2$ (35.0 g, 137.93 mmol). The mixture was stirred at 25° C. for 10 hrs. The reaction mixture was quenched by the addition of HCl (1 N) 100 mL at 0° C. (pH=6), extracted with EtOAc and the combined organic layers were washed with brine, dried with Na$_2$SO$_4$, filtered and concentrated under reduced pressure to afford crude 5-bromo-2-iodo-pyridin-3-ol (30 g) as a yellow solid which was submitted to the next step without further purification. LCMS (ESI): m/z [M+H] calcd for C$_5$H$_4$BrINO: 299.8; found 299.8.

Step 2.

To a solution of 5-bromo-2-iodo-pyridin-3-ol (29 g, 96.7 mmol) in DMF (400 mL) was added K$_2$CO$_3$ (20.0 g, 145.05 mmol) and benzyl bromide (18.2 g, 106.37 mmol, 12 mL). The mixture was stirred at 25° C. for 3 hrs. The reaction mixture was diluted with H$_2$O (200 mL) and extracted with EtOAc. The combined organic layers were washed with brine, dried over Na$_2$SO$_4$, filtered and concentrated under reduced pressure. The crude residue was purified by column chromatography to afford 3-benzyloxy-5-bromo-2-iodo-pyridine (33 g, 88% yield) as a red solid. $^1$H NMR (400 MHz, Chloroform-d) δ ppm 8.10 (s, 1H) 7.48-7.34 (m, 5H) 7.15 (s, 1H) 5.16 (s, 2H).

Step 3.

To a solution of 3-benzyloxy-5-bromo-2-iodo-pyridine (1.2 g, 3.08 mmol) and (2,3-dichlorophenyl)boronic acid (588 mg, 3.08 mmol) in CH$_3$CN (20 mL) and H$_2$O (2 mL) was added K$_3$PO$_4$ (2 g, 9.24 mmol) and Pd(dppf)Cl$_2$.CH$_2$Cl$_2$ (252 mg, 308.0 μmol) at 25° C. under N$_2$. The mixture was stirred at 120° C. for 2 hrs. The reaction mixture was diluted with H$_2$O 20 mL and extracted with EtOAc. The combined organic layers were washed with brine 100 mL, dried over Na$_2$SO$_4$, filtered and concentrated under reduced pressure. The remaining residue was purified by column chromatography to afford 3-benzyloxy-5-bromo-2-(2,3-dichlorophenyl)pyridine (700 mg, 1.71 mmol, 56% yield) as a colorless oil. $^1$H NMR (400 MHz, Chloroform-d) δ ppm 8.36 (s, 1H) 7.51-7.47 (m, 2H) 7.34-7.26 (m, 6H) 5.09 (s, 2H).

Step 4.

To a solution of 3-benzyloxy-5-bromo-2-(2,3-dichlorophenyl)pyridine (680 mg, 1.66 mmol) and N-[(4R)-8-azaspiro[4.5]decan-4-yl]-2-methyl-propane-2-sulfinamide (643 mg, 2.49 mmol) in toluene (10 mL) was added t-BuONa (319 mg, 3.32 mmol), [1-(2-diphenylphosphanyl-1-naphthyl)-2-naphthyl]-diphenyl-phosphane (103 mg, 166 μmol) and Pd$_2$(dba)$_3$ (76 mg, 83 μmol) at 25° C. under N$_2$. The mixture was stirred at 120° C. for 3 hrs. The reaction mixture was concentrated under reduced pressure and the remaining residue was purified by column chromatography to afford N-[(4R)-8-[5-benzyloxy-6-(2,3-dichlorophenyl)-3-pyridyl]-8-azaspiro[4.5]decan-4-yl]-2-methyl-propane-2-sulfinamide (700 mg, 72% yield) as a yellow solid. LCMS (ESI): m/z [M+H] calcd for C$_{31}$H$_{38}$Cl$_2$N$_3$O$_2$S: 586.2; found 586.1.

Step 5.

To a solution of N-[(4R)-8-[5-benzyloxy-6-(2,3-dichlorophenyl)-3-pyridyl]-8-azaspiro[4.5]decan-4-yl]-2-methyl-propane-2-sulfinamide (1.15 g, 1.96 mmol) in DCM (15 mL) was added NBS (1.05 g, 5.88 mmol) at 0° C. The mixture was stirred at 25° C. for 1 hr. The reaction mixture was quenched by the addition of saturated NaHSO$_3$ (5 mL). To the solution was then added TEA (540 mg, 5.3 mmol, 740.2 μL) and Boc$_2$O (777 mg, 3.56 mmol, 818 μL). The resulting mixture was stirred at 25° C. for 0.5 hrs. The reaction mixture was concentrated under reduced pressure and the crude residue was purified by column chromatography to afford tert-butyl N-[(4R)-8-[5-benzyloxy-2-bromo-6-(2,3-dichlorophenyl)-3-pyridyl]-8-azaspiro[4.5]decan-4-yl]carbamate (900 mg, 76% yield) as a yellow oil. $^1$H NMR (400 MHz, Chloroform-d) δ ppm 7.49-7.33 (m, 1H) 7.32-7.28 (m, 9H) 5.09 (s, 1H) 4.42-4.54 (m, 1H) 3.85-3.83 (d, J=7.95 Hz, 1H) 3.36-3.24 (m, 1H) 2.85-2.80 (t, J=10.27 Hz, 1H) 1.95-1.76 (m, 1H) 1.90-1.87 (m, 1H) 1.81-1.62 (m, 3H) 1.60-1.52 (m, 3H) 1.49-1.45 (m, 10H); LCMS (ESI): m/z [M+H] calcd for C$_{32}$H$_{36}$BrCl$_2$N$_3$O$_3$: 662.1; found 662.0.

Step 6.

To a solution of (R)-tert-butyl (8-(5-(benzyloxy)-2-bromo-6-(2,3-dichlorophenyl)pyridin-3-yl)-8-azaspiro[4.5]decan-1-yl)carbamate (700 mg, 1.06 mmol) in MeOH (10 mL) and THF (10 mL) was added Pd(dppf)Cl$_2$ (155 mg, 212 μmol) and Et$_3$N (322 mg, 3.18 mmol, 441 μL) at 25° C. The mixture was stirred at 80° C. for 2 hrs under CO (50 psi). The reaction mixture was filtered and the filtrate was concentrated under reduced pressure. The remaining residue was purified by column chromatography to afford (R)-methyl 5-(benzyloxy)-3-(1-((tert-butoxycarbonyl)amino)-8-azaspiro[4.5]decan-8-yl)-6-(2,3-dichlorophenyl)picolinate (400 mg, 59% yield) as a red solid. $^1$H NMR (400 MHz, Chloroform-d) δ ppm 7.40-7.38 (dd, J=7.89, 1.53 Hz, 1H) 7.25-7.14 (m, 8H) 6.83 (s, 1H) 5.05 (s, 2H) 4.39-4.36 (d, J=9.05 Hz, 1H) 3.83-3.70 (m, 3H) 3.19-3.16 (d, J=7.95 Hz, 1H) 2.87-2.85 (dd, J=17.55, 13.02 Hz, 2H) 2.83-2.82 (m, 2H) 2.02-1.95 (m, 1H) 1.88-1.52 (m, 7H) 1.59-1.38 (m, 10H); LCMS (ESI): m/z [M+H] calcd for C$_{34}$H$_{40}$Cl$_2$N$_3$O$_5$: 640.2; found 640.1.

Step 7.

To a solution of (R)-methyl 5-(benzyloxy)-3-(1-((tert-butoxycarbonyl)amino)-8-azaspiro[4.5]decan-8-yl)-6-(2,3-dichlorophenyl)picolinate (400 mg, 624.4 µmol) in THF (5 mL) was added LiBH$_4$ (27 mg, 1.25 mmol) at 0° C. The mixture was stirred at 40° C. for 2 hrs. The reaction mixture was quenched by addition H$_2$O (5 mL) at 0° C., and extracted with EtOAc. The combined organic layers were washed with brine, dried over Na$_2$SO$_4$, filtered and concentrated under reduced pressure to afford (R)-tert-butyl (8-(5-(benzyloxy)-6-(2,3-dichlorophenyl)-2-(hydroxymethyl)pyridin-3-yl)-8-azaspiro[4.5]decan-1-yl)carbamate (350 mg, crude) as a yellow oil. LCMS (ESI): m/z [M+H] calcd for C$_{33}$H$_{40}$C$_{12}$N$_3$O$_4$: 612.2; found 612.2 Step 8.

A solution of tert-butyl N-[(4R)-8-[5-benzyloxy-6-(2,3-dichlorophenyl)-2-(hydroxymethyl)-3-pyridyl]-8-azaspiro[4.5]decan-4-yl]carbamate (200 mg, 326.49 µmol) in HCl/MeOH (5.00 mL, 4 N) was stirred at 90° C. for 0.5 hrs. The reaction mixture was concentrated under reduced pressure and the resulting residue was purified by prep-HPLC to afford 5-[(4R)-4-amino-8-azaspiro[4.5]decan-8-yl]-2-(2,3-dichlorophenyl)-6-(hydroxymethyl)pyridin-3-ol (100 mg, 236.77 µmol, 73% yield) as a white solid. $^1$H NMR (400 MHz, Chloroform-d) δ ppm 8.53 (s, 1H) 7.57-7.54 (m, 1H) 7.36-7.31 (d, 2H) 7.30-7.06 (m, 1H) 4.66 (s, 2H) 3.26-3.14 (m, 3H) 2.92-2.86 (m, 2H) 1.90-1.85 (m, 2H) 1.84-1.57 (m, 10H); LCMS (ESI): m/z [M+H] calcd for C$_{21}$H$_{26}$Cl$_2$N$_3$O$_2$: 422.1; found 422.1.

Example 2. Synthesis of 5-[(1R)-1-amino-8-azaspiro[4.5]decan-8-yl]-2-[(2,3-dichlorophenyl)sulfanyl]-6-(hydroxymethyl)pyridin-3-ol

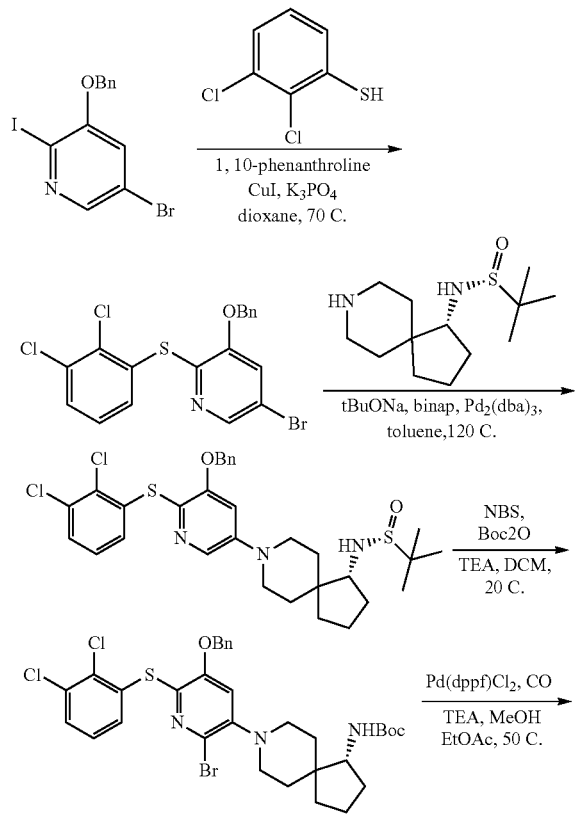

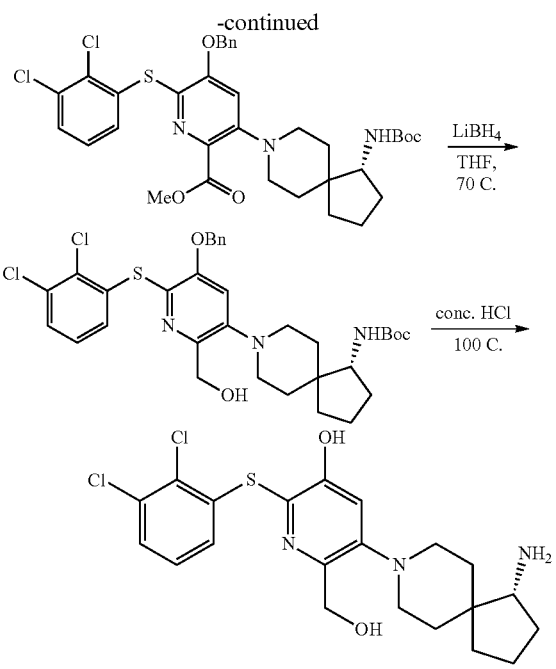

Step 1.

To a mixture of 3-(benzyloxy)-5-bromo-2-iodopyridine (5.0 g, 12.82 mmol) and 2,3-dichlorobenzenethiol (2.3 g, 12.82 mmol) in dioxane (50 mL) under N$_2$ was added CuI (244 mg, 1.28 mmol), K$_3$PO$_4$ (3.3 g, 15.38 mmol) and 1,10-phenanthroline (231 mg, 1.28 mmol). The mixture was stirred at 70° C. for 3 hrs, then poured into 50 mL of H$_2$O and the aqueous phase was extracted with EtOAc. The combined organic phases were washed with brine, dried with anhydrous Na$_2$SO$_4$, filtered and concentrated in vacuum. The residue was purified by silica gel chromatography to give 3-(benzyloxy)-5-bromo-2-((2,3-dichlorophenyl)thio)pyridine (4.6 g, 81% yield). $^1$H NMR (400 MHz, Chloroform-d) δ ppm 8.10 (d, J=17.10 Hz, 1H) 7.59-7.37 (m, 7H) 7.37-7.16 (m, 2H) 5.22 (d, J=17.54 Hz, 2H).

Step 2.

In a microwave tube 3-(benzyloxy)-5-bromo-2-((2,3-dichlorophenyl)thio)pyridine (1.1 g, 2.49 mmol), N-[(4R)-8-azaspiro[4.5]decan-4-yl]-2-methyl-propane-2-sulfinamide (967 mg, 3.74 mmol), t-BuONa (479 mg, 4.99 mmol), Pd$_2$(dba)$_3$ (114 mg, 124.67 µmol) and BINAP (155 mg, 249.34 µmol) were dissolved in toluene (10 mL). The sealed tube was heated at 120° C. for 3 hrs in the microwave after which the reaction mixture was cooled to room temperature and poured into 100 mL of H$_2$O. The organic phase was washed with brine, dried over anhydrous Na$_2$SO$_4$, filtered and concentrated under vacuum. The crude residue was purified by silica gel chromatography to give (R)—N—((R)-8-(5-(benzyloxy)-6-((2,3-dichlorophenyl)thio)pyridin-3-yl)-8-azaspiro[4.5]decan-1-yl)-2-methylpropane-2-sulfinamide (5.1 g, 83% yield) as a yellow solid. Note: 4 identical reactions were carried out in parallel and combined for work up and purification. $^1$H NMR (400 MHz, Chloroform-d) δ ppm 7.92 (d, J=2.32 Hz, 1H) 7.39-7.31 (m, 3H) 7.30-7.25 (m, 3H) 7.03 (t, J=7.95 Hz, 1H) 6.94 (dd, J=7.95, 1.10 Hz, 1H) 6.76 (d, J=2.32 Hz, 1H) 5.11 (s, 2H) 3.57 (t, J=12.90 Hz, 2H) 3.43-3.34 (m, 1H) 3.22 (d, J=5.26 Hz, 1H) 3.01-2.87 (m, 2H) 2.20-2.09 (m, 1H) 1.94 (td, J=12.53, 4.40 Hz, 1H) 1.88-1.65 (m, 5H) 1.58-1.51 (m, 1H) 1.46 (d, J=13.57 Hz, 2H) 1.25 (s, 9H).

Step 3.

To a solution of (R)—N—((R)-8-(5-(benzyloxy)-6-((2,3-dichlorophenyl)thio)pyridin-3-yl)-8-azaspiro[4.5]decan-1-yl)-2-methylpropane-2-sulfinamide (3.0 g, 4.85 mmol) in DCM (50 mL) was added NBS (2.6 g, 14.55 mmol) and the reaction was stirred at 20° C. for 2 hrs. Then TEA (1.47 g, 14.55 mmol, 2 mL) and Boc$_2$O (2.12 g, 9.70 mmol, 2.2 mL) were added and the mixture was stirred for 1 additional hr. The reaction mixture was poured into H$_2$O and extracted with DCM. The combined organic phases were washed with brine, dried with anhydrous Na$_2$SO$_4$, filtered and concentrated under vacuum. The crude residue was purified by silica gel chromatography to give (R)-tert-butyl (8-(5-(benzyloxy)-2-bromo-6-((2,3-dichlorophenyl)thio)pyridin-3-yl)-8-azaspiro[4.5]decan-1-yl)carbamate (2.4 g, 3.42 mmol, 71% yield).

Step 4.

To a solution of (R)-tert-butyl (8-(5-(benzyloxy)-2-bromo-6-((2,3-dichlorophenyl)thio)pyridin-3-yl)-8-azaspiro[4.5]decan-1-yl yl)carbamate (2.37 g, 3.42 mmol) in MeOH (30 mL) and EtOAc (30 mL) was added Pd(dppf)Cl$_2$ (250 mg, 342 μmol) and TEA (692 mg, 6.84 mmol, 947 μL). After sealing the reaction vessel the resulting suspension was degassed. The head space of the reaction was evacuated and backfilled with CO several times. The mixture was stirred under CO (50 psi) at 50° C. for 15 hrs, then filtered and concentrated under vacuum. The crude residue was purified silica gel chromatography to give (R)-methyl 5-(benzyloxy)-3-(1-((tert-butoxycarbonyl)amino)-8-azaspiro[4.5]decan-8-yl)-6-((2,3-dichlorophenyl)thio)picolinate (1.5 g, 65% yield). LCMS (ESI): m/z [M+H] calculated for C$_{34}$H$_{40}$Cl$_2$N$_3$O$_5$S: 672.2; found 672.1; $^1$H NMR (400 MHz, Chloroform-d) δ ppm 7.38-7.27 (m, 5H) 7.24-7.18 (m, 2H) 7.06-6.97 (m, 2H) 6.83 (s, 1H) 5.13 (s, 2H) 4.45 (br d, J=9.54 Hz, 1H) 3.92-3.86 (m, 3H) 3.86-3.76 (m, 1H) 3.29-3.16 (m, 2H) 3.01-2.89 (m, 2H) 2.16-2.07 (m, 1H) 1.95-1.85 (m, 1H) 1.79-1.62 (m, 5H) 1.47 (s, 9H).

Step 5.

To a solution of methyl (R)-methyl 5-(benzyloxy)-3-(1-((tert-butoxycarbonyl)amino)-8-azaspiro[4.5]decan-8-yl)-6-((2,3-dichlorophenyl)thio)picolinate (1.4 g, 2.08 mmol) in THF (25 mL) was added LiBH$_4$ (272 mg, 12.48 mmol). After stirring at 70° C. for 2 hrs the reaction was cooled to room temperature, poured into H$_2$O and extracted with EtOAc. The combined organic phases were washed with brine, dried with anhydrous Na$_2$SO$_4$, filtered and concentrated under vacuum. The crude residue was purified by silica gel chromatography to give (R)-tert-butyl (8-(5-(benzyloxy)-6-((2,3-dichlorophenyl)thio)-2-(hydroxymethyl)pyridin-3-yl)-8-azaspiro[4.5]decan-1-yl)carbamate (1.04 g, 78% yield). $^1$H NMR (400 MHz, Chloroform-d) δ ppm 7.44-7.32 (m, 6H) 7.31-7.26 (m, 1H) 7.16-7.10 (m, 1H) 6.94 (s, 1H) 5.16 (s, 2H) 4.57-4.52 (m, 2H) 4.42 (br d, J=9.17 Hz, 1H) 3.84-3.67 (m, 2H) 2.95-2.85 (m, 2H) 2.71 (t, J=11.19 Hz, 2H) 2.14-2.06 (m, 1H) 1.88-1.78 (m, 1H) 1.77-1.59 (m, 5H) 1.49-1.43 (m, 9H). LCMS (ESI): m/z [M+H] calculated for C$_{33}$H$_{40}$Cl$_2$N$_3$O$_4$S: 644.2; found 644.2.

Step 6.

A solution of (R)-tert-butyl (8-(5-(benzyloxy)-6-((2,3-dichlorophenyl)thio)-2-(hydroxymethyl)pyridin-3-yl)-8-azaspiro[4.5]decan-1-yl)carbamate (500 mg, 775.61 μmol) in conc. HCl (15 mL) was heated to 100° C. for 2 hrs and then cooled to room temperature, filtered and concentrated under reduced pressure. The residue was purified by prep-HPLC to afford 5-[(1R)-1-amino-8-azaspiro[4.5]decan-8-yl]-2-[(2,3-dichlorophenyl)sulfanyl]-6-(hydroxymethyl)pyridin-3-ol (60 mg, 17% yield) as a white solid. $^1$H NMR (400 MHz, Methanol-d$_4$) δ ppm 7.28 (dd, J=7.89, 1.32 Hz, 1H) 7.07 (t, J=8.11 Hz, 1H) 6.94 (s, 1H) 6.81 (dd, J=8.33, 1.32 Hz, 1H) 4.58-4.55 (m, 2H) 3.19-3.05 (m, 3H) 2.86 (t, J=11.84 Hz, 2H) 2.19-2.09 (m, 1H) 2.04 (s, 1H) 1.93-1.57 (m, 7H) 1.56-1.43 (m, 2H). LCMS (ESI): m/z [M+H] calculated for C$_{21}$H$_{26}$Cl$_2$N$_3$O$_2$S: 454.1; found 454.1.

Example 3. Synthesis of 5-[(1R)-1-amino-8-azaspiro[4.5]decan-8-yl]-2-(2,3-dichlorophenyl)pyridin-3-ol

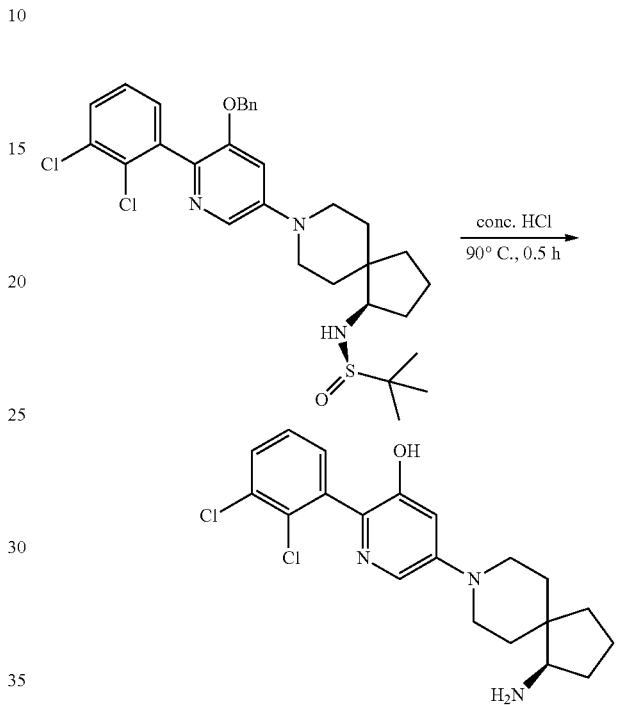

A solution of (R)—N—((R)-8-(5-(benzyloxy)-6-(2,3-dichlorophenyl)pyridin-3-yl)-8-azaspiro[4.5]decan-1-yl)-2-methylpropane-2-sulfinamide (700 mg, 1.19 mmol) in conc. HCl (10 mL) was stirred at 90° C. for 0.5 hrs. The solution was concentrated under reduced pressure. The remaining residue was purified by prep-HPLC to afford 5-[(1R)-1-amino-8-azaspiro[4.5]decan-8-yl]-2-(2,3-dichlorophenyl)pyridin-3-ol (61 mg, 13% yield) as a white solid. $^1$H NMR (400 MHz, Chloroform-d) δ ppm 8.421 (s, 1H) 7.738-7.795 (m, 1H) 7.471-7.491 (d, 1H) 7.193-7.289 (m, 2H) 6.811 (s, 1H) 3.561-3.651 (m, 2H) 3.164-3.198 (m, 1H) 2.917-2.974 (m, 2H) 1.701-1.814 (m, 1H) 1.489-1.690 (m, 9H). LCMS (ESI): m/z [M+H] calcd for C$_{20}$H$_{24}$Cl$_2$N$_3$O: 392.1; found 392.3.

Example 4. Synthesis of {3-[(1R)-1-amino-8-azaspiro[4.5]decan-8-yl]-6-(2,3-dichlorophenyl)-5-methylpyridin-2-yl}methanol

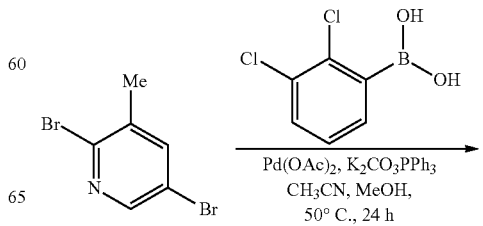

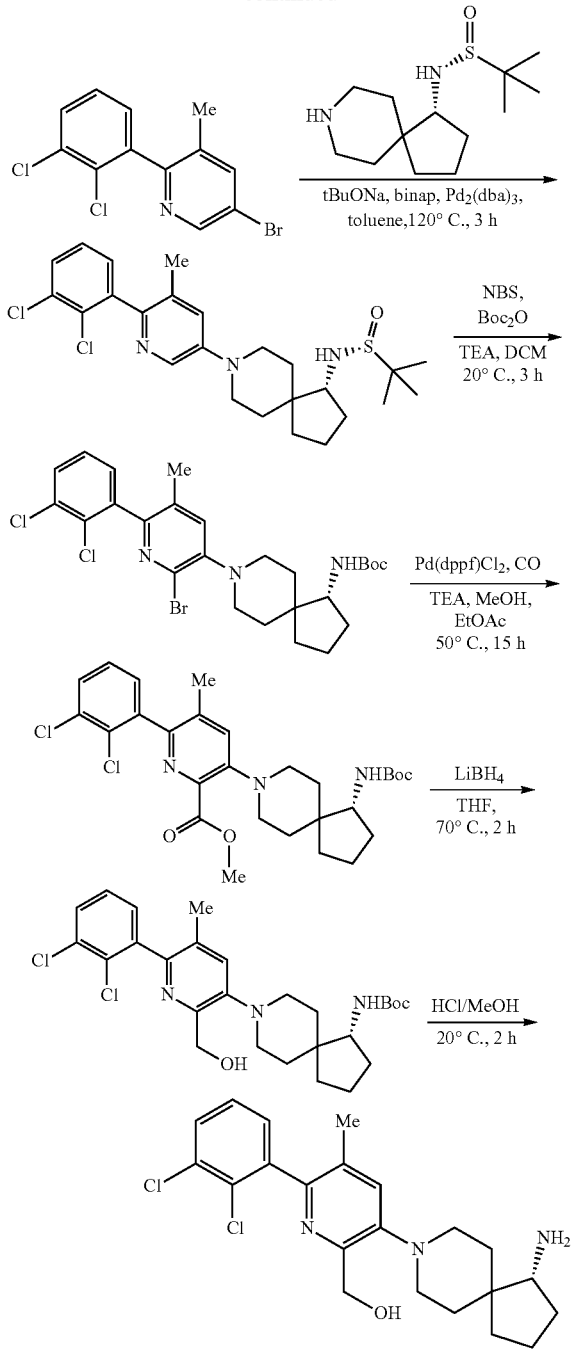

Step 1.

A mixture of 2,5-dibromo-3-methylpyridine (5.0 g, 19.93 mmol), (2,3-dichlorophenyl)boronic acid (4.2 g, 21.92 mmol), Pd(OAc)₂ (447 mg, 1.99 mmol), PPh₃ (1.1 g, 3.99 mmol), and K₂CO₃ (5.5 g, 39.86 mmol) in CH₃CN (150 mL) and MeOH (75 mL) was stirred at 50° C. under nitrogen atmosphere for 24 hrs. The reaction mixture was poured into 50 mL of H₂O and the aqueous phase was extracted with EtOAc. The combined organic phases were washed with brine, dried with anhydrous Na₂SO₄, filtered and concentrated under reduced pressure. The resulting residue was purified by column chromatography to afford 5-bromo-2-(2,3-dichlorophenyl)-3-methylpyridine (5.1 g, 81% yield) as a light yellow oil. ¹H NMR (400 MHz, Chloroform-d) δ ppm 8.57 (d, J=9.21 Hz, 1H) 7.76 (d, J=8.77 Hz, 1H) 7.52 (t, J=8.33 Hz, 1H) 7.35-7.25 (m, 1H) 7.23-7.15 (m, 1H) 2.13 (d, J=9.21 Hz, 3H).

Step 2.

A mixture of 5-bromo-2-(2,3-dichlorophenyl)-3-methylpyridine (900 mg, 2.84 mmol), N-[(4R)-8-azaspiro[4.5]decan-4-yl]-2-methyl-propane-2-sulfinamide (1.1 g, 4.26 mmol), t-BuONa (546 mg, 5.68 mmol), Pd₂(dba)3 (130 mg, 141.9 μmol) and BINAP (177 mg, 284 μmol) in toluene (12 mL) was heated at 120° C. for 3 hrs. The reaction mixture was poured into 50 mL of H₂O and the aqueous phase was washed with EtOAc. The combined organic phase were washed with brine, dried with anhydrous Na₂SO₄, filtered and concentrated under reduced pressure. The resulting residue was purified by column chromatography to afford (R)—N—((R)-8-(6-(2,3-dichlorophenyl)-5-methylpyridin-3-yl)-8-azaspiro[4.5]decan-1-yl)-2-methylpropane-2-sulfinamide (4.0 g, 95% yield) as a white solid. ¹H NMR (400 MHz, Methanol-d₄) δ ppm 8.08 (d, J=2.69 Hz, 1H) 7.61 (dd, J=8.01, 1.41 Hz, 1H) 7.43-7.37 (m, 1H) 7.33 (d, J=2.57 Hz, 1H) 7.26 (dd, J=7.64, 1.41 Hz, 1H) 3.73 (td, J=7.83, 3.79 Hz, 2H) 2.96 (qd, J=12.25, 2.75 Hz, 2H) 2.12-2.03 (m, 4H) 1.96-1.62 (m, 5H) 1.61-1.38 (m, 3H) 1.27-1.20 (m, 9H).

Step 3.

To a mixture of (R)—N—((R)-8-(6-(2,3-dichlorophenyl)-5-methylpyridin-3-yl)-8-azaspiro[4.5]decan-1-yl)-2-methylpropane-2-sulfinamide (4 g, 8.09 mmol) in DCM (50 mL) was added NBS (4.32 g, 24.27 mmol) at 20° C. and stirred for 2 hrs. To the mixture was added TEA (2.46 g, 24.27 mmol, 3.3 mL) and Boc₂O (3.53 g, 16.18 mmol, 3.72 mL) at 20° C. and stirred for 1 hr. The reaction mixture was poured into 100 mL of H₂O and the aqueous phase was washed with DCM. The combined organic phases were washed with brine, dried with anhydrous Na₂SO₄, filtered and concentrated under reduced pressure. The resulting residue was purified by column chromatography to afford (R)-tert-butyl (8-(2-bromo-6-(2,3-dichlorophenyl)-5-methylpyridin-3-yl)-8-azaspiro[4.5]decan-1-yl)carbamate (1.4 g, 30% yield) as a white solid. ¹H NMR (400 MHz, Chloroform-d) δ ppm 7.50 (dd, J=7.89, 1.75 Hz, 1H) 7.21-7.18 (m, 3H) 4.47 (br d, J=9.65 Hz, 1H) 3.83 (d, J=7.89 Hz, 1H) 3.42-3.25 (m, 2H) 2.87 (t, J=10.30 Hz, 2H) 2.15-2.06 (m, 3H) 1.96 (t, J=12.06 Hz, 2H) 1.83-1.64 (m, 16H) LCMS (ESI): m/z [M+Na] calculated for C₂₆H₃₂BrCl₂N₃ONa: 592.1; found 592.0.

Step 4.

To a solution of (R)-tert-butyl (8-(2-bromo-6-(2,3-dichlorophenyl)-5-methylpyridin-3-yl)-8-azaspiro[4.5]decan-1-yl)carbamate (1.4 g, 2.46 mmol) in MeOH (20 mL) and EtOAc (20 mL) was added TEA (498 mg, 4.9 mmol, 681 μL) and Pd(dppf)Cl₂ (180 mg, 246 μmol) under N₂. The suspension was degassed under vacuum and purged with CO several times. The resultant mixture was stirred under CO (50 psi) at 50° C. for 15 hrs. The reaction mixture was filtered and the filtrate was concentrated under reduced pressure. The resultant residue was purified by column chromatography to afford (R)-methyl 3-(1-((tert-butoxycarbonyl)amino)-8-azaspiro[4.5]decan-8-yl)-6-(2,3-dichlorophenyl)-5-methylpicolinate (1 g, 1.82 mmol, 74% yield) as a yellow solid. ¹H NMR (400 MHz, Chloroform-d) δ ppm 7.48 (dd, J=7.70, 1.96 Hz, 1H) 7.28 (m, 2H) 7.25-7.23 (m, 1H) 7.22 (d, J=2.08 Hz, 1H) 4.45 (br d, J=9.29 Hz, 1H) 3.96-3.89 (m, 3H) 3.87-3.71 (m, 1H) 3.34-3.20 (m, 2H) 3.04-2.89 (m, 2H) 2.14 (s, 3H) 2.09 (dd, J=12.96, 5.50 Hz, 1H) 1.95-1.85 (m, 1H) 1.79-1.63 (m, 4H) 1.46 (s, 10H). LCMS (ESI): m/z [M+H] calculated for C₂₈H₃₆Cl₂N₃O₄: 548.2; found 548.2.

Step 5.

To a solution of (R)-methyl 3-(1-((tert-butoxycarbonyl)amino)-8-azaspiro[4.5]decan-8-yl)-6-(2,3-dichlorophenyl)-5-methylpicolinate (800 mg, 1.46 mmol) in THF (15 mL) was added LiBH$_4$ (191 mg, 8.76 mmol) in one portion, and the resultant mixture was stirred at 70° C. for 2 hrs. The reaction mixture was poured into 30 mL of H$_2$O and the aqueous phase was washed with EtOAc. The combined organic phases were washed with brine, dried with anhydrous Na$_2$SO$_4$, filtered and concentrated under reduced pressure. The resultant residue was purified by column chromatography to afford (R)-tert-butyl (8-(6-(2,3-dichlorophenyl)-2-(hydroxymethyl)-5-methylpyridin-3-yl)-8-azaspiro[4.5]decan-1-yl)carbamate (570 mg, 75% yield) as a white solid. $^1$H NMR (400 MHz, Chloroform-d) δ ppm 7.52 (dd, J=8.01, 1.16 Hz, 1H) 7.31-7.28 (m, 2H) 7.23-7.18 (m, 1H) 4.73 (s, 2H) 4.57 (br s, 1H) 4.46 (d, J=9.41 Hz, 1H) 3.82 (br d, J=8.19 Hz, 1H) 3.04 (d, J=4.52 Hz, 2H) 2.88-2.79 (m, 2H) 2.14 (s, 3H) 2.11-2.06 (m, 1H) 1.94-1.85 (m, 1H) 1.80-1.62 (m, 4H) 1.48 (s, 10H). LCMS (ESI): m/z [M+H] calculated for C$_{27}$H$_{36}$Cl$_2$N$_3$O$_3$: 520.2; found 520.2.

Step 6.

A solution of (R)-tert-butyl (8-(6-(2,3-dichlorophenyl)-2-(hydroxymethyl)-5-methylpyridin-3-yl)-8-azaspiro[4.5]decan-1-yl)carbamate (520 mg, 1 mmol) in HCl/MeOH (10 mL) was stirred at 20° C. for 2 hrs. The reaction was filtered and the filtrate concentrated under reduced pressure. The resultant residue was purified by prep-HPLC to afford {3-[(1R)-1-amino-8-azaspiro[4.5]decan-8-yl]-6-(2,3-dichlorophenyl)-5-methylpyridin-2-yl}methanol (210 mg, 50% yield) as a white solid. $^1$H NMR (400 MHz, Methanol-d$_4$) δ ppm 7.62 (dd, J=8.11, 1.53 Hz, 1H) 7.54 (s, 1H) 7.41 (t, J=7.67 Hz, 1H) 7.27 (dd, J=7.67, 1.53 Hz, 1H) 4.74 (br d, J=3.95 Hz, 2H) 3.30-3.24 (m, 1H) 3.24-3.10 (m, 2H) 2.96 (br t, J=11.62 Hz, 2H) 2.23 (br s, 1H) 2.12 (s, 3H) 1.99-1.69 (m, 7H) 1.60 (br t, J=11.62 Hz, 2H). LCMS (ESI): m/z [M+H] calculated for C$_{22}$H$_{28}$Cl$_2$N$_3$O: 420.2; found 420.1.

Example 5. Synthesis of (1R)-8-[6-(2,3-dichlorophenyl)-5-methylpyridin-3-yl]-8-azaspiro[4.5]decan-1-amine

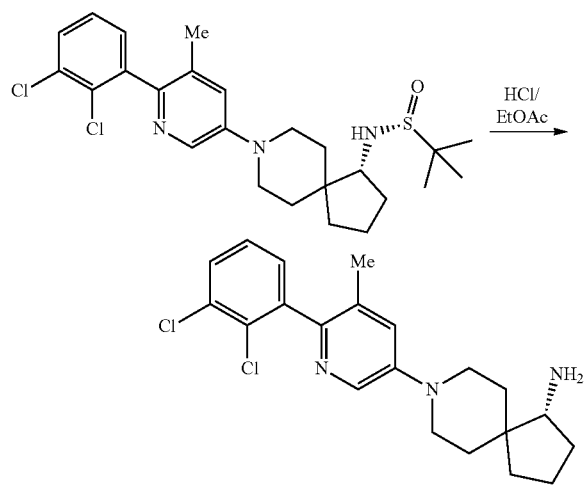

A mixture of (R)—N—((R)-8-(6-(2,3-dichlorophenyl)-5-methylpyridin-3-yl)-8-azaspiro[4.5]decan-1-yl)-2-methylpropane-2-sulfinamide (770 mg, 1.5 mmol) in HCl/EtOAc (20 mL) was stirred at 25° C. under N$_2$ for 3 hrs. The reaction mixture was filtered and concentrated under reduced pressure. The resulting residue was purified by prep-HPLC to afford (R)-8-(6-(2,3-dichlorophenyl)-5-methylpyridin-3-yl)-8-azaspiro[4.5]decan-1-amine (190 mg, 31% yield) as a white solid. $^1$H NMR (400 MHz, Methanol-d$_4$) δ ppm 8.09 (d, J=2.43 Hz, 1H) 7.61 (d, J=8.16 Hz, 1H) 7.33-7.42 (m, 2H) 7.24 (d, J=7.72 Hz, 1H) 3.65-3.79 (m, 2H) 3.25 (t, J=6.73 Hz, 1H) 3.21-3.27 (m, 1H) 2.97-3.07 (m, 2H) 2.17-2.29 (m, 1H) 2.09 (s, 3H) 1.68-1.92 (m, 8H) 1.53-1.65 (m, 2H) LCMS (ESI): m/z [M+H] calculated for C$_{21}$H$_{26}$Cl$_2$N$_3$: 390.1; found 390.1.

Example 6. Synthesis of {3-[(1R)-1-amino-8-azaspiro[4.5]decan-8-yl]-6-[(2,3-dichlorophenyl)sulfanyl]-5-methylpyridin-2-yl}methanol

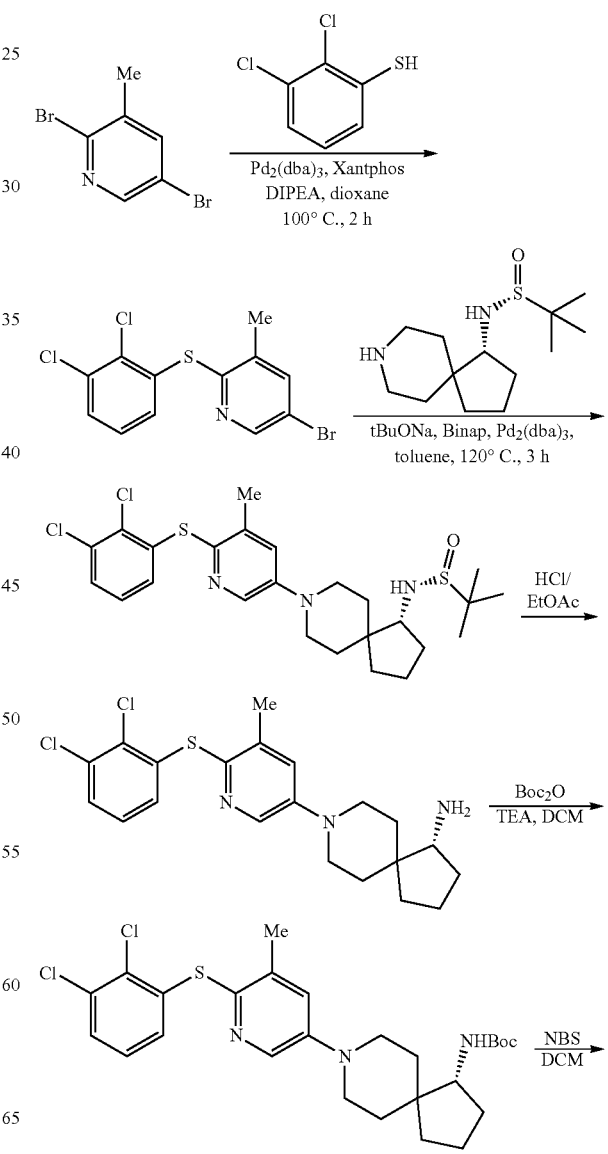

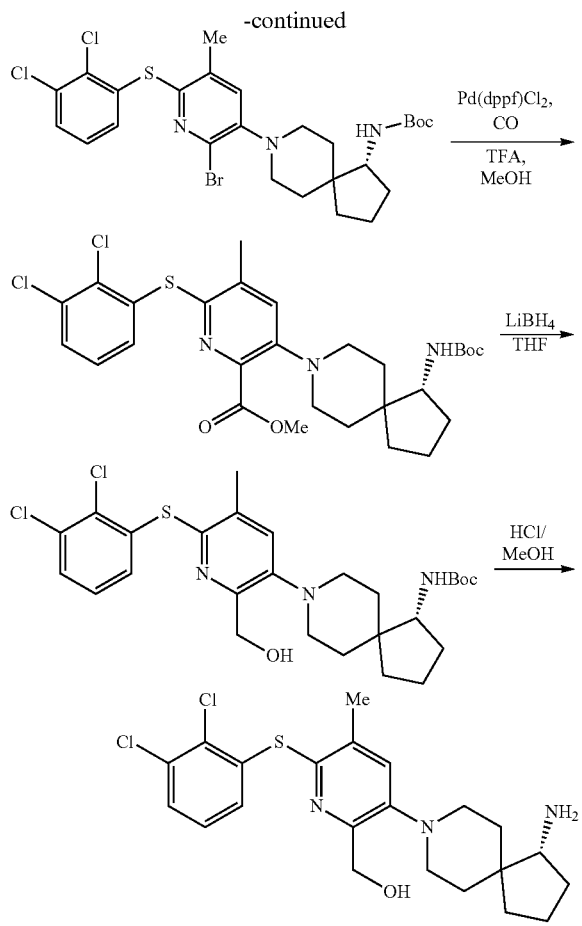

Step 1.

To a solution of 2,3-dichlorobenzenethiol (2.57 g, 14.35 mmol) and 2,5-dibromo-3-methyl-pyridine (3 g, 11.96 mmol) in dioxane (30 mL) was added Pd$_2$(dba)$_3$ (110 mg, 120 μmol), Xantphos (138 mg, 239 μmol) and DIPEA (3.1 g, 23.92 mmol, 4.2 mL) at 25° C. under N$_2$. The reaction mixture was stirred at 90° C. for 3 hrs. The reaction mixture was concentrated under reduced pressure and the resulting residue was purified by column chromatography to afford 5-bromo-2-(2, 3-dichlorophenyl) sulfanyl-3-methyl-pyridine (2.8 g, 67% yield) as a white solid. $^1$H NMR (400 MHz, Chloroform-d) δ ppm 8.27-8.26 (d, J=2.08 Hz, 1H) 7.59-7.48 (d, J=1.59 Hz, 1H) 7.45-7.39 (dd, J=8.01, 1.53 Hz, 1H) 7.39-7.37 (dd, J=7.82, 1.47 Hz, 1H) 7.37-7.18 (m, 1H) 2.37 (s, 3H).

Step 2.

To a solution of 5-bromo-2-(2,3-dichlorophenyl)sulfanyl-3-methyl-pyridine (1 g, 2.86 mmol) and N-[(4R)-8-azaspiro[4.5]decan-4-yl]-2-methyl-propane-2-sulfinamide (961 mg, 3.72 mmol) in toluene (10 mL) was added t-BuONa (550 mg, 5.72 mmol), [1-(2-diphenylphosphanyl-1-naphthyl)-2-naphthyl]-diphenyl-phosphane (178 mg, 286 μmol) and Pd$_2$(dba)$_3$ (131 mg, 143 μmol) at 25° C. The reaction mixture was stirred at 130° C. for 3 hrs. The reaction mixture was concentrated under reduced pressure and the resulting crude residue was purified by column chromatography to afford N-[(4R)-8-[6-(2, 3-dichlorophenyl) sulfanyl-5-methyl-3-pyridyl]-8-azaspiro[4.5]decan-4-yl]-2-methyl-propane-2-sulfinamide (1.5 g, 50% yield) as a yellow oil.

Step 3.

A solution of N-[(4R)-8-[6-(2,3-dichlorophenyl)sulfanyl-5-methyl-3-pyridyl]-8-azaspiro[4.5]decan-4-yl]-2-methyl-propane-2-sulfinamide (1.50 g, 2.85 mmol) in HCl/EtOAc (20 mL) was stirred at 25° C. for 0.5 hrs. The reaction mixture was concentrated under reduce pressure to afford crude (4R)-8-[6-(2,3-dichlorophenyl)sulfanyl-5-methyl-3-pyridyl]-8-azaspiro[4.5]decan-4-amine (1.5 g, crude, HCl salt) as a yellow solid. The crude residue was used in the next step without further purification. LCMS (ESI): m/z [M+H] calcd for C$_{21}$H$_{26}$Cl$_2$N$_3$S: 422.1; found 422.0.

Step 4.

To a solution of (4R)-8-[6-(2, 3-dichlorophenyl) sulfanyl-5-methyl-3-pyridyl]-8-azaspiro[4.5]decan-4-amine (1.5 g, 3.55 mmol) in DCM (15 mL) was added Boc$_2$O (1.16 g, 5.33 mmol, 1.2 mL) and TEA (1.1 g, 10.65 mmol, 1.5 mL). The reaction mixture was stirred at 25° C. for 1 hr. The reaction mixture was concentrated under reduced pressure and the crude residue was purified by column chromatography (to afford tert-butyl N-[(4R)-8-[6-(2, 3-dichlorophenyl) sulfanyl-5-methyl-3-pyridyl]-8-azaspiro[4.5]decan-4-yl]carbamate (600 mg, 32% yield) as a yellow oil. LCMS (ESI): m/z [M+H] calcd for C$_{26}$H$_{34}$Cl$_2$N$_3$O$_2$S: 522.2; found 522.1.

Step 5.

To a solution of tert-butyl N-[(4R)-8-[6-(2,3-dichlorophenyl)sulfanyl-5-methyl-3-pyridyl]-8-azaspiro[4.5]decan-4-yl]carbamate (600 mg, 1.15 mmol) in DCM (8 mL) was added NBS (409.35 mg, 2.30 mmol) at 0° C. The reaction mixture was stirred at 25° C. for 1 hr. The reaction mixture was concentrated under reduced pressure and the resulting residue was purified by column chromatography to afford tert-butyl N-[(4R)-8-[2-bromo-6-(2, 3-dichlorophenyl) sulfanyl-5-methyl-3-pyridyl]-8-azaspiro[4.5]decan-4-yl]carbamate (300 mg, 43% yield) as a yellow oil. LCMS (ESI): m/z [M+H] calcd for C$_{26}$H$_{33}$BrCl$_2$N$_3$O$_2$S: 602.1; found 602.0.

Step 6.

To a solution of tert-butyl N-[(4R)-8-[2-bromo-6-(2,3-dichlorophenyl)sulfanyl-5-methyl-3-pyridyl]-8-azaspiro[4.5]decan-4-yl]carbamate (400 mg, 665 μmol) in THF (5 mL) and MeOH (5 mL) was added Pd(dppf)Cl$_2$ (97 mg, 133 μmol) and TEA (202 mg, 2.00 mmol, 277 μL) at 20° C. The mixture was stirred at 50° C. for 1 hr under CO (50 psi). The reaction mixture was concentrated under reduced pressure and the resulting crude residue was purified by column chromatography (SiO$_2$, Petroleum ether:Ethyl acetate=30:1 to 10:1) to afford methyl 3-[(4R)-4-(tert-butoxycarbonylamino)-8-azaspiro[4.5]decan-8-yl]-6-(2, 3-dichlorophenyl) sulfanyl-5-methyl-pyridine-2-carboxylate (500 mg, crude) as a yellow solid. The crude residue was used in the next step without further purification. LCMS (ESI): m/z [M+H] calcd for C$_{28}$H$_{36}$Cl$_2$N$_3$O$_4$S: 580.2; found 580.1.

Step 7.

To a solution of methyl 3-[(4R)-4-(tert-butoxycarbonylamino)-8-azaspiro[4.5]decan-8-yl]-6-(2, 3-dichlorophenyl) sulfanyl-5-methyl-pyridine-2-carboxylate (500 mg, 861 μmol) in THF (20 mL) was added LiBH$_4$ (38 mg, 1.72 mmol) at 0° C. The mixture was stirred at 35° C. for 2 hrs. The reaction mixture was quenched by the addition of H$_2$O (5 mL) at 0° C., diluted with H$_2$O (20 mL) and extracted with EtOAc. The combined organic layers were washed with brine, dried over Na$_2$SO$_4$, filtered and concentrated under reduced pressure to afford tert-butyl N-[(4R)-8-[6-(2, 3-dichlorophenyl) sulfanyl-2-(hydroxymethyl)-5-methyl-3-pyridyl]-8-azaspiro[4.5]decan-4-yl]carbamate (400 mg, crude) as a yellow solid. The crude residue was used in the next step without further purification. LCMS (ESI): m/z [M+H] calcd for C$_{27}$H$_{36}$Cl$_2$N$_3$O$_3$SH: 552.2; found 552.0.

Step 8.

A solution of tert-butyl N-[(4R)-8-[6-(2, 3-dichlorophenyl) sulfanyl-2-(hydroxymethyl)-5-methyl-3-pyridyl]-8-azaspiro[4.5]decan-4-yl]carbamate (400 mg, 724 mol) in HCl/MeOH (10 mL) was stirred at 25° C. for 0.5 hrs. The reaction mixture was concentrated under reduced pressure and the remaining residue was purified by prep-HPLC to afford {3-[(1R)-1-amino-8-azaspiro[4.5]decan-8-yl]-6-[(2, 3-dichlorophenyl)sulfanyl]-5-methylpyridin-2-yl}methanol (76 mg, 23% yield) as a white solid. $^1$H NMR (400 MHz, Chloroform-d) δ ppm 8.53 (s, 1H) 7.46-7.43 (m, 1H) 7.20-7.16 (m, 2H) 7.05-7.03 (m, 2H) 4.58 (s, 2H) 3.24-3.21 (m, 1H) 2.92-3.08 (m, 2H) 2.89-2.86 (m, 2H) 2.35 (s, 2H) 1.88-1.86 (m, 1H) 1.85-1.54 (m, 10H). LCMS (ESI): m/z [M+H] calcd for $C_{22}H_{28}Cl_2N_3OS$: 452.1; found 452.1.

Example 7. Synthesis of (1R)-8-{6-[(2,3-dichlorophenyl)sulfanyl]-5-methylpyridin-3-yl}-8-azaspiro [4.5]decan-1-amine

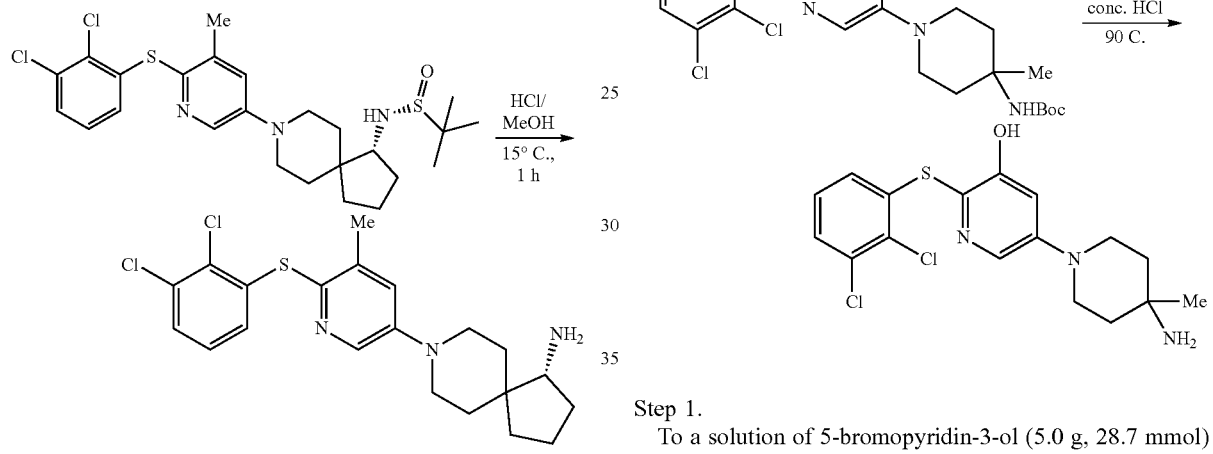

A mixture of (R)—N—((R)-8-(6-((2,3-dichlorophenyl) thio)-5-methylpyridin-3-yl)-8-azaspiro[4.5]decan-1-yl)-2-methylpropane-2-sulfinamide (500 mg, 949 μmol) in HCl/MeOH (5 mL) was stirred at 15° C. for 1 hr. The mixture was concentrated under reduced pressure and the resulting crude residue was purified by prep-HPLC to afford (R)-8-(6-((2, 3-dichlorophenyl)thio)-5-methylpyridin-3-yl)-8-azaspiro [4.5]decan-1-amine (170 mg, 42% yield) as a yellow solid. $^1$H NMR (400 MHz, Methanol-d$_4$) δ ppm 8.36 (s, 1H), 8.00 (s, 1H), 7.49 (d, J=8.0 Hz, 1H), 7.25 (t, J=8.0 Hz, 1H), 6.85 (d, J=8.0 Hz, 1H), 4.02-3.92 (m, 2H), 3.30-3.23 (m, 2H), 2.44 (s, 3H), 2.25-1.20 (m, 1H), 1.93-1.63 (m, 10H). LCMS (ESI): m/z [M+H] calculated for $C_{21}H_{26}Cl_2N_3S$: 422.1; found 422.0.

Example 8. Synthesis of 5-(4-amino-4-methylpiperidin-1-yl)-2-[(2,3-dichlorophenyl) sulfanyl]pyridin-3-ol

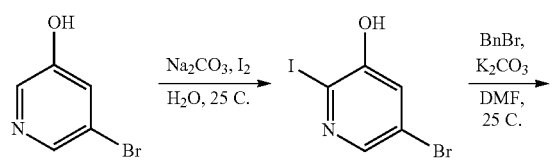

-continued

[structures of intermediates with reagents: CuI, K$_3$PO$_4$, 1,10-phenanthroline, dioxane, 70 C.; tBuONa, binap, Pd$_2$(dba)$_3$ toluene, 120 C.; conc. HCl, 90 C.]

Step 1.

To a solution of 5-bromopyridin-3-ol (5.0 g, 28.7 mmol) in H$_2$O (300 mL) was added Na$_2$CO$_3$ (6.1 g, 57.5 mmol) and I$_2$ (7.3 g, 28.7 mmol). The mixture was stirred at 25° C. for 3 hrs. The reaction mixture was extracted with EtOAc and the combined organic layers were washed with brine, dried over Na$_2$SO$_4$, filtered and concentrated under reduced pressure. The crude residue was purified by silica gel chromatography to give 5-bromo-2-iodopyridin-3-ol (7.5 g, 87% yield). $^1$H NMR (400 MHz, Chloroform-d) δ ppm 8.09 (s, 1H) 7.39 (s, 1H).

Step 2.

To a solution of 5-bromo-2-iodopyridin-3-ol (4 g, 13.34 mmol) in DMF (20 mL) was added K$_2$CO$_3$ (2.77 g, 20.01 mmol) and bromomethylbenzene (2.51 g, 14.67 mmol, 1.74 mL). The mixture was stirred at 25° C. for 3 hrs, after which the reaction mixture was diluted with H$_2$O and extracted with EtOAc. The combined organic layers were washed with brine, dried over Na$_2$SO$_4$, filtered and concentrated under reduced pressure. The crude residue was purified by column chromatography to give 3-(benzyloxy)-5-bromo-2-iodopyridine (3.2 g, 62% yield). $^1$H NMR (400 MHz, Chloroform-d) δ ppm 8.21 (s, 1H) 7.47-7.59 (m, 5H) 7.36 (s, 1H) 5.27 (s, 2H).

Step 3.

To a solution of 3-(benzyloxy)-5-bromo-2-iodopyridine (3.2 g, 8.2 mmol) and 2,3-dichlorobenzenethiol (1.5 g, 8.2 mmol) in dioxane (30 mL) was added CuI (156 mg, 820 μmol), K$_3$PO$_4$ (2.1 g, 9.8 mmol) and 1,10-phenanthroline (148 mg, 820 μmol) at 25° C. The mixture was stirred at 70° C. for 3 hrs. The reaction mixture was cooled to room temperature, diluted with H$_2$O (10 mL) and extracted with EtOAc. The combined organic layers were washed with brine, dried over Na$_2$SO$_4$, filtered and concentrated under reduced pressure. The crude residue was purified by silica gel chromatography to give 3-(benzyloxy)-5-bromo-2-((2,3-dichlorophenyl)thio)pyridine (2.80 g, 77% yield). $^1$H NMR (400 MHz, Chloroform-d) δ ppm 8.04 (s, 1H) 7.48-7.49 (m, 2H) 7.41-7.47 (m, 4H) 7.18-7.20 (m, 1H) 5.16 (s, 2H).

Step 4.

To a solution of 3-(benzyloxy)-5-bromo-2-((2,3-dichlorophenyl)thio)pyridine (1 g, 2.27 mmol) and tert-butyl N-(4-methyl-4-piperidyl)carbamate (632 mg, 2.95 mmol) in toluene (10 mL) was added t-BuONa (436 mg, 4.54 mmol), [1-(2-diphenylphosphanyl-1-naphthyl)-2-naphthyl]-diphenyl-phosphane (141 mg, 227 µmol) and Pd$_2$(dba)$_3$ (104 mg, 113.5 µmol). The mixture was stirred at 120° C. for 3 hrs under microwave conditions. After cooling to room temperature the reaction mixture was concentrated and the residue was purified by silica gel chromatography to give tert-butyl (1-(5-(benzyloxy)-6-((2,3-dichlorophenyl)thio)pyridin-3-yl)-4-methylpiperidin-4-yl)carbamate (300 mg, 23% yield). $^1$H NMR (400 MHz, Chloroform-d) δ ppm 7.92 (s, 1H) 7.29-7.37 (m, 3H) 6.95-7.03 (m, 2H) 6.76 (s, 1H) 5.12 (s, 2H) 3.36-3.39 (m, 2H) 3.09-3.14 (m, 2H) 2.14-2.17 (m, 2H) 1.69-1.76 (m, 2H) 1.47 (s, 9H) 1.41 (s, 3H).

Step 5.

HCl (10 mL, conc.) was added to tert-butyl (1-(5-(benzyloxy)-6-((2,3-dichlorophenyl)thio)pyridin-3-yl)-4-methylpiperidin-4-yl)carbamate (200 mg, 348.09 µmol). The mixture was stirred at 90° C. for 20 min. The reaction mixture was cooled to room temperature and lyophilized. The residue was purified by prep-HPLC to give 5-(4-amino-4-methylpiperidin-1-yl)-2-((2,3-dichlorophenyl)thio)pyridin-3-ol (60 mg, 45% yield). 1H NMR (400 MHz, Chloroform-d) δ ppm 8.449 (s, 1H) 7.806 (s, 1H) 7.205-7.225 (m, 1H) 6.969-7.009 (m, 1H) 6.819 (s, 1H) 6.535-6.555 (m, 1H) 3.566-3.598 (m, 2H) 3.117-3.181 (m, 2H) 1.821-1.848 (m, 4H) 1.383 (s, 3H). LCMS (ESI): m/z [M+H] calcd for C$_{17}$H$_{20}$Cl$_2$N$_3$OS: 384.1; found 384.1.

Example 9. Synthesis of 5-[(1R)-1-amino-8-azaspiro[4.5]decan-8-yl]-2-[(2,3-dichlorophenyl)sulfanyl]pyridin-3-ol

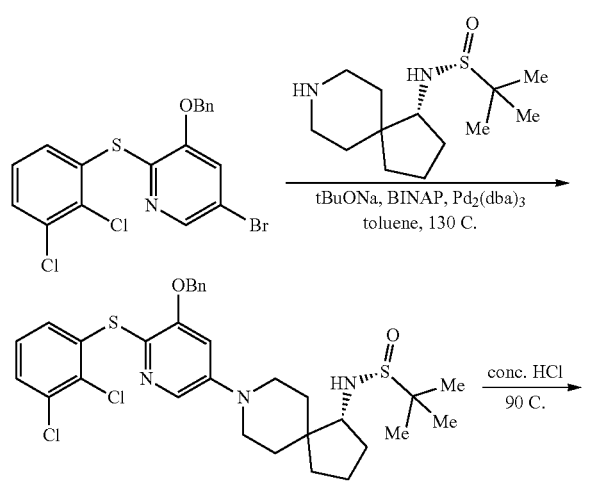

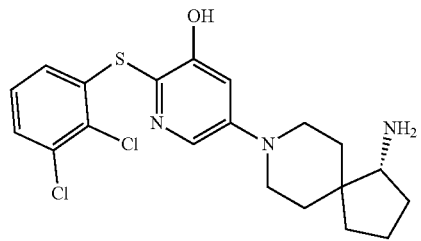

Step 1.

To a solution of 3-(benzyloxy)-5-bromo-2-((2,3-dichlorophenyl)thio)pyridine (1 g, 2.27 mmol) and N-[(4R)-8-azaspiro[4.5]decan-4-yl]-2-methyl-propane-2-sulfinamide (763 mg, 2.95 mmol) in toluene (10 mL) was added t-BuONa (436 mg, 4.54 mmol), BINAP (141 mg, 227 µmol) and Pd$_2$(dba)$_3$ (104 mg, 114 µmol). The mixture was stirred at 130° C. for 3 hrs under microwave conditions. The reaction mixture was cooled to room temperature and the solvent was removed under reduced pressure. The residue was purified by silica gel column chromatography to give (R)—N—((R)-8-(5-(benzyloxy)-6-((2,3-dichlorophenyl)thio) pyridin-3-yl)-8-azaspiro[4.5]decan-1-yl)-2-methylpropane-2-sulfinamide (200 mg, 14% yield). $^1$H NMR (400 MHz, Chloroform-d) δ ppm 7.89 (s, 1H) 7.29-7.34 (m, 4H) 7.00-7.02 (t, J=7.95 Hz, 1H) 6.90-6.98 (d, J=7.95 Hz, 1H) 6.74 (s, 1H) 5.03 (s, 2H) 3.51-3.58 (m, 2H) 3.35-3.36 (m, 1H) 3.20-3.21 (d, J=5.01 Hz, 1H) 2.90-2.96 (m, 2H) 1.63-1.79 (m, 13H) 1.44 (s, 9H).

Step 2.

A mixture of (R)—N—((R)-8-(5-(benzyloxy)-6-((2,3-dichlorophenyl)thio)pyridin-3-yl)-8-azaspiro[4.5]decan-1-yl)-2-methylpropane-2-sulfinamide (200 mg, 323 µmol) and conc. HCl (10 mL) was stirred at 90° C. for 20 min and then cooled to room temperature and lyophilized. The residue was purified by preparative HPLC to give (R)-5-(1-amino-8-azaspiro[4.5]decan-8-yl)-2-((2,3-dichlorophenyl)thio) pyridin-3-ol (53 mg, 125 µmol, 39% yield) as a white solid. $^1$H NMR (400 MHz, Chloroform-d) δ ppm 7.77 (d, J=2.21 Hz, 1H) 7.18-7.19 (d, J=7.94 Hz, 1H) 6.95-6.99 (t, J=8.05 Hz, 1H) 6.78 (s, 1H) 6.49-6.51 (d, J=8.16 Hz, 1H) 3.58-3.67 (m, 2H) 3.11-3.15 (t, J=6.73 Hz, 1H) 2.92-2.98 (m, 2H) 2.12 (m, 1H) 1.44-1.75 (m, 9H). LCMS (ESI): m/z [M+H] calcd for C$_{20}$H$_{24}$Cl$_2$N$_3$OS: 424.1; found 424.0.

Example 10. Synthesis of 2-[(2-amino-3-chloropyridin-4-yl)sulfanyl]-5-[(3S,4S)-4-amino-3-methyl-2-oxa-8-azaspiro[4.5]decan-8-yl]-6-(hydroxymethyl)pyridin-3-ol

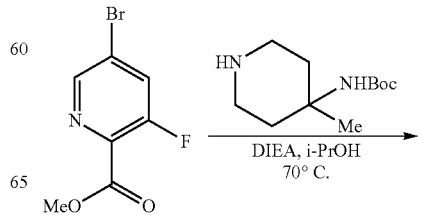

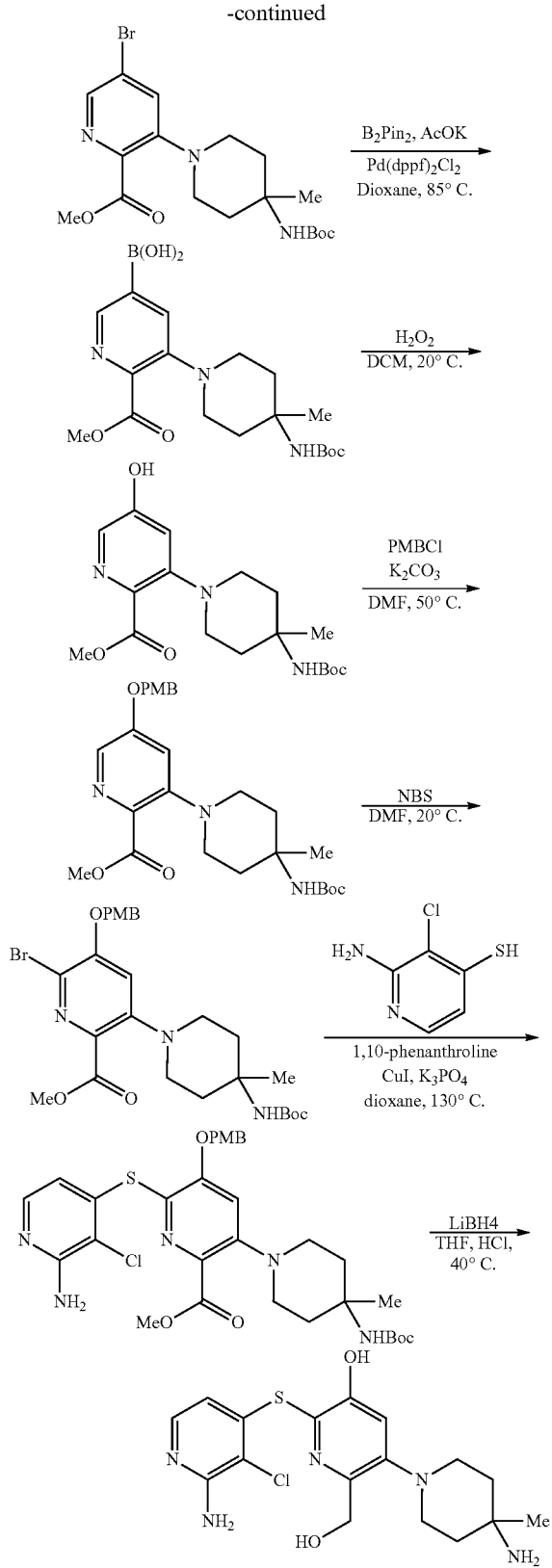

Step 1.

To a solution of methyl 5-bromo-3-fluoro-pyridine-2-carboxylate (1.5 g, 6.41 mmol) in i-PrOH (30 mL) was added DIEA (8.3 g, 64.10 mmol, 11 mL) and tert-butyl N-(4-methyl-4-piperidyl)carbamate (1.51 g, 7.05 mmol). The mixture was heated to 70° C. for 5 hrs and then concentrated under reduced pressure. The crude residue was purified by silica gel chromatography to give methyl 5-bromo-3-[4-(tert-butoxycarbonylamino)-4-methyl-1-piperidyl]pyridine-2-carboxylate (2.5 g, 5.84 mmol, 91% yield). $^1$H NMR (400 MHz, Methanol-d$_4$) δ ppm 8.15 (d, J=1.76 Hz, 1H) 7.75 (d, J=1.98 Hz, 1H) 3.92 (s, 3H) 3.09-2.98 (m, 4H) 2.14 (br d, J=13.23 Hz, 2H) 1.72-1.60 (m, 2H) 1.43 (s, 9H) 1.34 (s, 3H).

Step 2.

To a solution of methyl 5-bromo-3-[4-(tert-butoxycarbonylamino)-4-methyl-1-piperidyl]pyridine-2-carboxylate (2.5 g, 5.84 mmol) in dioxane (37 mL) was added 4,4,5,5-tetramethyl-2-(4,4,5,5-tetramethyl-1,3,2-dioxaborolan-2-yl)-1,3,2-dioxaborolane (2.22 g, 8.76 mmol), KOAc (1.15 g, 11.67 mmol) and Pd(dppf)Cl$_2$—CH$_2$Cl$_2$ (477 mg, 584 µmol). The reaction mixture was stirred at 85° C. for 2 hrs, cooled to room temperature and filtered. The filtrate was concentrated under reduced pressure and the the crude residue was purified by reversed-phase column to give [5-[4-(tert-butoxycarbonylamino)-4-methyl-1-piperidyl]-6-methoxycarbonyl-3-pyridyl]boronic acid (1.2 g, 52% yield) as yellow solid. LCMS (ESI): m/z [M+H] calculated for C$_{18}$H$_{29}$BN$_3$O$_6$: 394.2; found 394.3; $^1$H NMR (400 MHz, Methanol-d$_4$) δ ppm 8.23 (br s, 1H) 7.97 (s, 1H) 3.99-3.93 (m, 3H) 3.13-3.01 (m, 4H) 2.17 (br d, J=12.35 Hz, 2H) 1.74-1.65 (m, 2H) 1.44 (s, 9H) 1.36-1.33 (m, 3H).

Step 3.

H$_2$O$_2$ (1.04 g, 9.15 mmol, 880 µL, 30% purity) was added slowly to a solution of [5-[4-(tert-butoxycarbonylamino)-4-methyl-1-piperidyl]-6-methoxycarbonyl-3-pyridyl]boronic acid (1.2 g, 3.05 mmol) in DCM (12 mL) at 0° C. The reaction was warmed to room temperature and stirred for 5 hrs. The mixture was quenched with sat. aq. Na$_2$S$_2$O$_3$ and adjusted to pH<7 with 1N HCl. The mixture was extracted with EtOAc. The organic layer was washed with brine, dried over Na$_2$SO$_4$, filtered and the solvent was evaporated. The residue was purified by silica gel chromatography to give methyl 3-[4-(tert-butoxycarbonylamino)-4-methyl-1-piperidyl]-5-hydroxy-pyridine-2-carboxylate (0.83 g, 74% yield). LCMS (ESI): m/z [M+H] calculated for C$_{18}$H$_{28}$N$_3$O$_5$: 366.2; found 366.2; $^1$H NMR (400 MHz, Methanol-d$_4$) δ ppm 7.68 (d, J=2.21 Hz, 1H) 6.92 (d, J=2.43 Hz, 1H) 3.88 (s, 3H) 3.08-2.91 (m, 4H) 2.19-2.08 (m, 2H) 1.76-1.65 (m, 2H) 1.43 (s, 9H) 1.34 (s, 3H).

Step 4.

To a solution of methyl 3-[4-(tert-butoxycarbonylamino)-4-methyl-1-piperidyl]-5-hydroxy-pyridine-2-carboxylate (0.83 g, 2.27 mmol) in DMF (16 mL) was added 1-(chloromethyl)-4-methoxy-benzene (534 mg, 3.41 mmol, 464 µL) and K$_2$CO$_3$ (942 mg, 6.81 mmol). The reaction was stirred at 50° C. for 6 hrs and then partitioned between water and EtOAc. The combined organic fractions were washed with brine and then dried with Na$_2$SO$_4$, filtered and concentrated under vacuum. The crude residue was purified by silica gel chromatography to give methyl 3-[4-(tert-butoxycarbonylamino)-4-methyl-1-piperidyl]-5-[(4-methoxyphenyl)methoxy]pyridine-2-carboxylate (1.1 g, 99% yield). LCMS (ESI): m/z [M+H] calculated for C$_{26}$H$_{36}$N$_3$O$_6$: 486.3; found 486.3; $^1$H NMR (400 MHz, Methanol-d$_4$)δ ppm 7.84 (br s, 1H) 7.37 (br d, J=7.58 Hz, 2H) 7.09 (br s, 1H) 6.93 (br d, J=7.46 Hz, 2H) 5.13 (br s, 2H) 3.88 (br s, 3H) 3.78 (br s, 3H) 2.98 (br s, 4H) 2.85 (br s, 3H) 2.13 (br d, J=12.10 Hz, 2H) 1.78-1.65 (m, 2H) 1.43 (br s, 9H) 1.34 (br s, 3H).

Step 5.

To a solution of methyl 3-[4-(tert-butoxycarbonylamino)-4-methyl-1-piperidyl]-5-[(4-methoxyphenyl)methoxy]pyridine-2-carboxylate (1.1 g, 2.27 mmol) in DMF (10 mL) was added NBS (403 mg, 2.27 mmol). The reaction was stirred at 20° C. for 3 hrs and then poured into sat. aq. Na$_2$S$_2$O$_3$ aqueous. The mixture was extracted with EtOAc. The organic layer was washed with brine, dried over Na$_2$SO$_4$, filtered and the solvent was evaporated under reduced pressure. The crude residue was purified by silica gel chromatography to give methyl 6-bromo-3-[4-(tert-butoxycarbonylamino)-4-methyl-1-piperidyl]-5-[(4-methoxyphenyl)methoxy]pyridine-2-carboxylate (1 g, 78% yield). $^1$H NMR (400 MHz, Methanol-d$_4$) δ ppm 7.39 (d, J=8.77 Hz, 2H) 7.06 (s, 1H) 6.93 (d, J=8.77 Hz, 2H) 5.19 (s, 2H) 3.87 (s, 3H) 3.79 (s, 3H) 3.00 (br d, J=15.79 Hz, 4H) 2.13 (br d, J=13.15 Hz, 2H) 1.72-1.60 (m, 2H) 1.44 (s, 9H) 1.33 (s, 3H). LCMS (ESI): m/z [M+H] calculated for C$_{26}$H$_{35}$BrN$_3$O$_6$: 564.2; found 564.2.

Step 6.

Methyl 6-bromo-3-[4-(tert-butoxycarbonylamino)-4-methyl-1-piperidyl]-5-[(4-methoxyphenyl) methoxy]pyridine-2-carboxylate (0.5 g, 885 μmol), 2-amino-3-chloropyridine-4-thiol (285 mg, 1.77 mmol), 1,10-phenanthroline (32 mg, 177.16 μmol), K$_3$PO$_4$ (376 mg, 1.77 mmol) and CuI (17 mg, 89 μmol) were weighed into a microwave tube and dioxane (5 mL) was added. The sealed tube was heated at 130° C. for 3 hrs in the microwave. The cooled to room temperature and partitioned between water and EtOAc. The aqueous phase was extracted with EtOAc and the combined organic fractions were washed with brine and then dried with Na$_2$SO$_4$, filtered and concentrated under reduced pressure. The crude residue was purified by silica gel chromatography to give methyl 6-[(2-amino-3-chloro-4-pyridyl)sulfanyl]-3-[4-(tert-butoxycarbonylamino)-4-methyl-1-piperidyl]-5-[(4-methoxyphenyl)methoxy]pyridine-2-carboxylate (0.41 g, 72% yield). LCMS (ESI): m/z [M+H] calculated for C$_{31}$H$_{39}$ClN$_5$O$_6$S: 644.3; found 644.2.

Step 7.

To a solution of methyl 6-[(2-amino-3-chloro-4-pyridyl)sulfanyl]-3-[4-(tert-butoxycarbonylamino)-4-methyl-1-piperidyl]-5-[(4-methoxyphenyl)methoxy]pyridine-2-carboxylate (0.36 g, 559 μmol) THF (2 mL) was added LiBH$_4$ (37 mg, 1.68 mmol). The reaction was stirred at 40° C. for 2 hrs upon which HCl (1 mL) was added at room temperature and the mixture was stirred for 4 more hrs at 30° C. The mixture was adjusted to pH=7 with NaHCO$_3$, filtered and the solvent was removed under reduced pressure. The residue was purified by prep-HPLC to give 2-[(2-amino-3-chloro-4-pyridyl)sulfanyl]-5-(4-amino-4-methyl-1-piperidyl)-6-(hydroxymethyl)pyridin-3-ol (23 mg, 10% yield) as a white solid. $^1$H NMR (400 MHz, Methanol-d$_4$) δ ppm 8.56-8.27 (m, 1H) 7.63-7.40 (m, 1H) 7.16-7.00 (m, 1H) 5.97-5.71 (m, 1H) 4.65-4.49 (m, 2H) 3.24 (br d, J=13.08 Hz, 2H) 3.07-2.99 (m, 2H) 2.06-1.88 (m, 4H) 1.62-1.35 (m, 3H). LCMS (ESI): m/z [M+H] calculated for C$_{17}$H$_{23}$ClN$_5$O$_2$S: 396.1; found 396.2.

Example 11. Synthesis of 5-(4-amino-4-methylpiperidin-1-yl)-2-(2,3-dichlorophenyl)-6-(hydroxymethyl)pyridin-3-ol

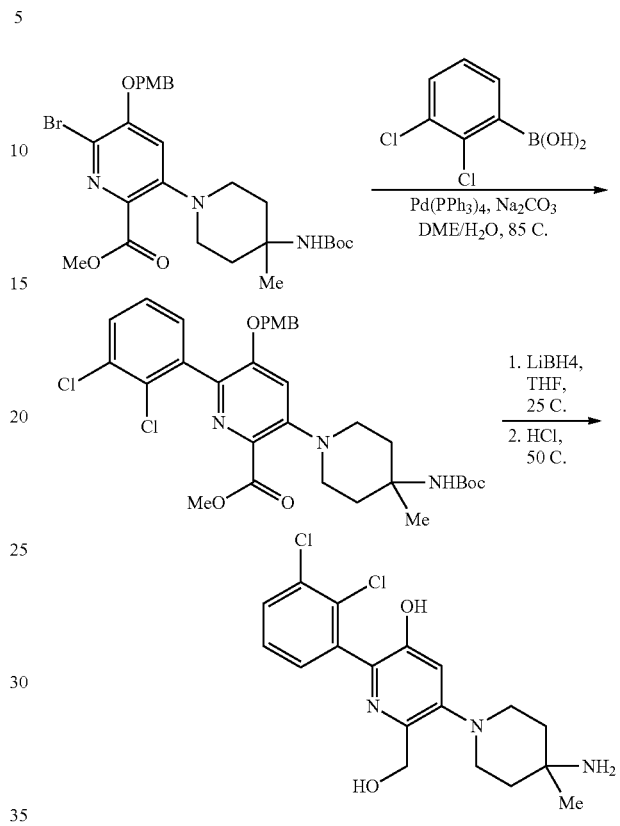

Step 1.

To a solution of methyl 6-bromo-3-[4-(tert-butoxycarbonylamino)-4-methyl-1-piperidyl]-5-[(4-methoxyphenyl)methoxy]pyridine-2-carboxylate (0.2 g, 354 μmol) in DME (5 mL) was added (2,3-dichlorophenyl)boronic acid (101 mg, 531 μmol), Na$_2$CO$_3$ (75 mg, 709 μmol), H$_2$O (1 mL) and Pd(PPh$_3$)$_4$ (82 mg, 71 μmol). The reaction was stirred at 85° C. for 3 hrs. After cooling to room temperature water was added and the aqueous layer was extracted with ethyl acetate. The combined organic fractions were washed with brine and then dried with. After filtration the solvent was removed under reduced pressure and the crude residue was purified by silica gel chromatography to give methyl 3-[4-(tert-butoxycarbonylamino)-4-methyl-1-piperidyl]-6-(2,3-dichlorophenyl)-5-[(4-methoxyphenyl)methoxy]pyridine-2-carboxylate (0.15 g, 67% yield). $^1$H NMR (400 MHz, Methanol-d$_4$) δ ppm 7.55 (dd, J=7.94, 1.54 Hz, 1H) 7.36-7.31 (m, 1H) 7.28-7.18 (m, 4H) 6.87 (s, 1H) 6.84 (s, 1H) 5.12 (s, 2H) 3.87 (s, 3H) 3.76 (s, 3H) 3.14-3.02 (m, 4H) 2.16 (br d, J=13.01 Hz, 2H) 1.75-1.66 (m, 2H) 1.45 (s, 9H) 1.36 (s, 3H). %). LCMS (ESI): m/z [M+H] calculated for C$_{32}$H$_{38}$Cl$_2$N$_3$O$_6$: 630.2; found 630.3.

Step 2.

To a solution of methyl 3-[4-(tert-butoxycarbonylamino)-4-methyl-1-piperidyl]-6-(2,3-dichlorophenyl)-5-[(4-methoxyphenyl)methoxy]pyridine-2-carboxylate (0.15 g, 238 μmol) in THF (2 mL) was added LiBH$_4$ (16 mg, 714 μmol). The reaction was stirred at 50° C. for 2 hrs. HCl (conc) was added and the mixture was stirred for another 2 hrs at 50° C. The mixture was cooled to room temperature, adjusted to pH=7 with aq.sat.NaHCO$_3$, filtered and concentrated under reduced pressure. The residue was purified by preparative HPLC to give 5-(4-amino-4-methyl-1-piperidyl)-2-(2,3-dichlorophenyl)-6-(hydroxymethyl)pyridin-3-ol (49 mg, 129 μmol, 54% yield). $^1$H NMR (400 MHz, Methanol-d$_4$) δ ppm 7.55 (m, 1H) 7.33 (m, 2H) 7.08 (s, 1H) 4.65 (m, 2H) 3.12 (m, 2H) 3.00 (m, 2H) 1.85 (m, 4H) 1.34 (s, 3H). LCMS (ESI): m/z [M+H] calculated for $C_{18}H_{22}Cl_2N_3O_2$: 382.1; found 382.1.

Example 12. Synthesis of {3-[(3S,4S)-4-amino-3-methyl-2-oxa-8-azaspiro[4.5]decan-8-yl]-6-(2,3-dichlorophenyl)-5-methylpyridin-2-yl}methanol

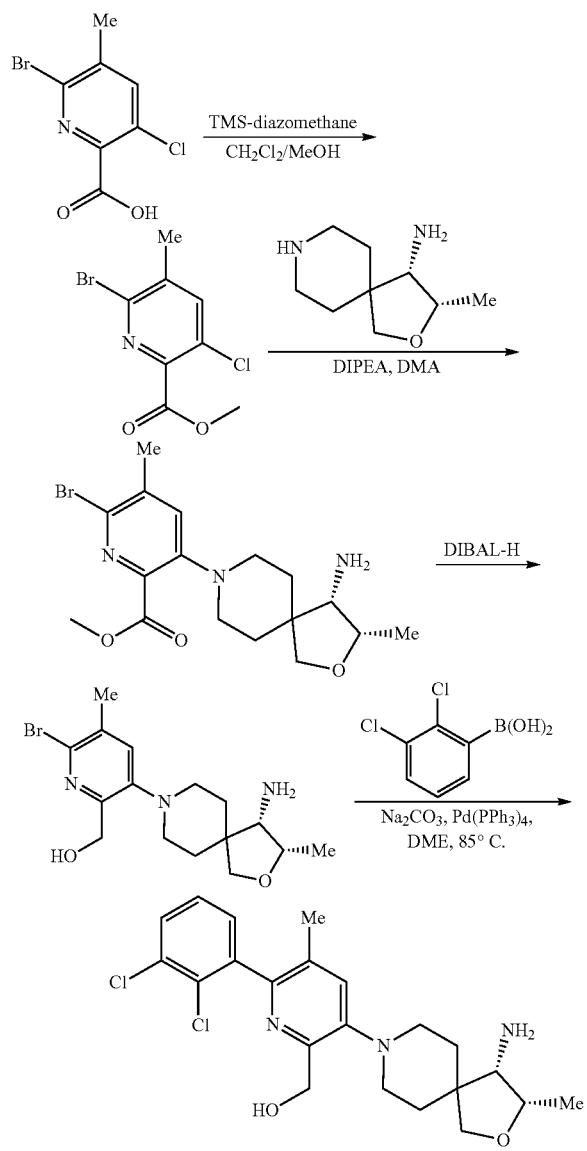

Step 1.

To a solution of 6-bromo-3-chloro-5-methylpyridine-2-carboxylic acid (200 mg, 798 μmol) in a 1:1 mix of methanol (4 mL):methylene chloride (4 mL) at 0° C. was added trimethylsilyldiazomethane (1.19 mL, 2.39 mmol) slowly until the exotherm subsides and then allowed to stir for an additional 15 min warming to room temperature. The resulting reaction mixture was concentrated in vacuo and the residue was purified by flash chromatography using 0-50% EtOAc/Hex to yield the desired product methyl 6-bromo-3-chloro-5-methylpyridine-2-carboxylate (210 mg, 99% yield). LCMS (ESI): m/z [M+H] calculated for $C_8H_8ClBrNO_2$: 263.9; found 264.1.

Step 2.

To a solution of ethyl 3-fluoro-5-methylpyridine-2-carboxylate (210 mg, 793 μmol) in DMA (3.96 mL) was added N-[(3S,4S)-8-chloro-3-methyl-2-oxa-8-azaspiro[4.5]decan-4-yl]chloranamine (208 mg, 872 μmol) and DIPEA (690 μL, 3.96 mmol). The reaction mixture was stirred at 120° C. overnight. The resulting reaction mixture was concentrated in vacuo, removing most of the DMA before purifying. The residue was purified by flash chromatography using 0-10% MeOH/CH$_2$Cl$_2$ to 20% MeOH to yield the desired product methyl 3-[(3S,4S)-4-amino-3-methyl-2-oxa-8-azaspiro[4.5]decan-8-yl]-6-bromo-5-methylpyridine-2-carboxylate (300 mg, 95% yield). LCMS (ESI): m/z [M+H] calculated for $C_{17}H_{25}BrN_3O_3$: 398.1; found 398.3.

Step 3.

A solution of methyl 3-[(3S,4S)-4-amino-3-methyl-2-oxa-8-azaspiro[4.5]decan-8-yl]-6-bromo-5-methylpyridine-2-carboxylate (315 mg, 790 μmol) in methylene chloride (8 mL) was cooled to –78° C. before slowly adding in 1M solution of DIBAL-H (3.9 mL, 3.9 mmol) in DCM. The reaction mixture was stirred at –78° C. for 1 hr. The resulting reaction mixture was diluted with Rochelle salt and CH$_2$Cl$_2$. The mixture was stirred at room temperature for 3 hrs before separating the organic layer, drying it over MgSO$_4$, filtering, and then concentrating in vacuo. The residue was purified by flash chromatography using 0-10% MeOH/CH$_2$Cl$_2$ to yield the desired product, {3-[(3S,4S)-4-amino-3-methyl-2-oxa-8-azaspiro[4.5]decan-8-yl]-6-bromo-5-methylpyridin-2-yl}methanol (210 mg, 72% yield). LCMS (ESI): m/z [M+H] calculated for $C_{16}H_{25}BrN_3O_2$: 370.1; found 370.1.

Step 4.

To a solution of {3-[(3S,4S)-4-amino-3-methyl-2-oxa-8-azaspiro[4.5]decan-8-yl]-6-bromo-5-methylpyridin-2-yl}methanol (70 mg, 0.189 mmol) and (2,3-dichlorophenyl)boronic acid (72 mg, 0.378 mmol) in DME (0.9 mL, 0.2 M) and H$_2$O (0.2 mL, 1 M) was added Na$_2$CO$_3$ (41 mg, 0.378 mmol), then Pd(PPh$_3$)$_4$ (22 mg, 0.019 mmol) was added to the reaction mixture. The mixture was stirred at 100° C. for 1 hr. At which point the reaction mixture was concentrated under reduced pressure. Purification by prep-HPLC afforded {3-[(3S,4S)-4-amino-3-methyl-2-oxa-8-azaspiro[4.5]decan-8-yl]-6-(2,3-dichlorophenyl)-5-methylpyridin-2-yl}methanol (38 mg, 46% yield) as white solid. $^1$H NMR (500 MHz, Methanol-d$_4$) δ 7.58 (dd, J=8.1, 1.6 Hz, 1H), 7.53 (s, 1H), 7.39-7.35 (m, 1H), 7.22 (dd, J=7.7, 1.6 Hz, 1H), 4.64 (s, 2H), 4.33-4.25 (m, 1H), 3.93 (d, J=9.1 Hz, 1H), 3.83 (d, J=9.0 Hz, 1H), 3.50-3.35 (m, 3H), 3.06-2.90 (m, 2H), 2.20 (s, 3H), 2.02-1.92 (m, 2H), 1.86 (d, J=12.2 Hz, 1H), 1.75-1.70 (m, 1H), 1.30 (d, J=6.5 Hz, 3H). LC-MS (ESI): m/z [M+H]+ calculated for $C_{22}H_{28}Cl_2N_3O_2$: 436.2; found 436.3.

Example 13. Synthesis of {6-[(2-amino-3-chloropyridin-4-yl)sulfanyl]-3-[(3S,4S)-4-amino-3-methyl-2-oxa-8-azaspiro[4.5]decan-8-yl]-5-methylpyridin-2-yl}methanol

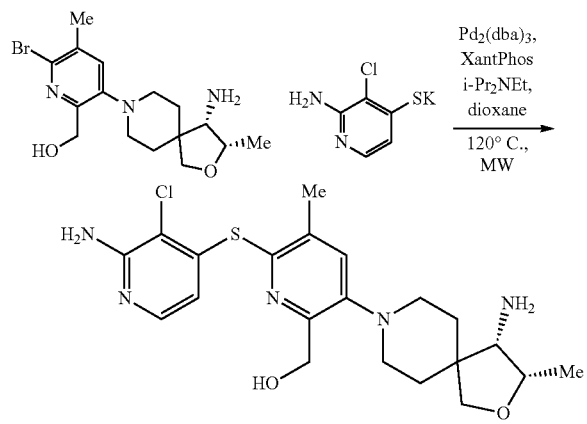

To a microwave vial was added {3-[(3S,4S)-4-amino-3-methyl-2-oxa-8-azaspiro[4.5]decan-8-yl]-6-bromo-5-methylpyridin-2-yl}methanol (70 mg, 0.189 mmol), 3-chloro-4-(potassiosulfanyl)pyridin-2-amine (75 mg, 0.377 mmol), tris(dibenzylideneacetone) dipalladium (17 mg, 0.0189 mmol), xantphos (21 mg, 0.038 mmol), and N,N-diisopropylethylamine (0.01 mL, 0.567 mmol). The mixture was evacuated under house vac for 15 min before degassed dioxane (1.9 mL, 0.1 M) was added. The reaction vial was evacuated and purged with $N_2$ three times before stirring under microwave conditions at 130° C. for 2 hrs. The reaction mixture was concentrated under reduced pressure and subjected to column. Purification by reverse phase column chromatography to afford 6-[(2-amino-3-chloropyridin-4-yl)sulfanyl]-3-[(3S,4S)-4-amino-3-methyl-2-oxa-8-azaspiro[4.5]decan-8-yl]-5-methylpyridin-2-yl}methanol (43 mg, 0.096 mmol, 51% yield) as white solid. $^1$H NMR (500 MHz, Methanol-$d_4$) δ 7.84 (s, 1H), 7.56 (d, J=5.6 Hz, 1H), 5.75 (d, J=5.5 Hz, 1H), 4.58 (s, 2H), 4.29 (qd, J=6.5, 4.2 Hz, 1H), 3.93 (d, J=9.0 Hz, 1H), 3.83 (d, J=9.0 Hz, 1H), 3.67-3.50 (m, 2H), 3.38 (d, J=4.2 Hz, 1H), 3.02 (dddd, J=34.3, 13.3, 11.0, 2.7 Hz, 2H), 2.45 (s, 3H), 2.01-1.91 (m, 2H), 1.89-1.82 (m, 1H), 1.71 (ddt, J=12.7, 4.5, 2.4 Hz, 1H), 1.30 (d, J=6.5 Hz, 3H); LC-MS (ESI): m/z [M+H]+ calculated for $C_{21}H_{29}ClN_5O_2S$: 450.2; found 450.3.

Example 14. Synthesis of [3-(4-amino-4-methylpiperidin-1-yl)-6-(2,3-dichlorophenyl)-5-methylpyridin-2-yl]methanol

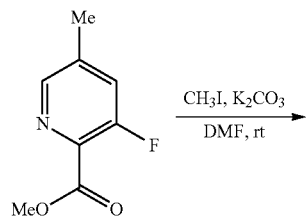

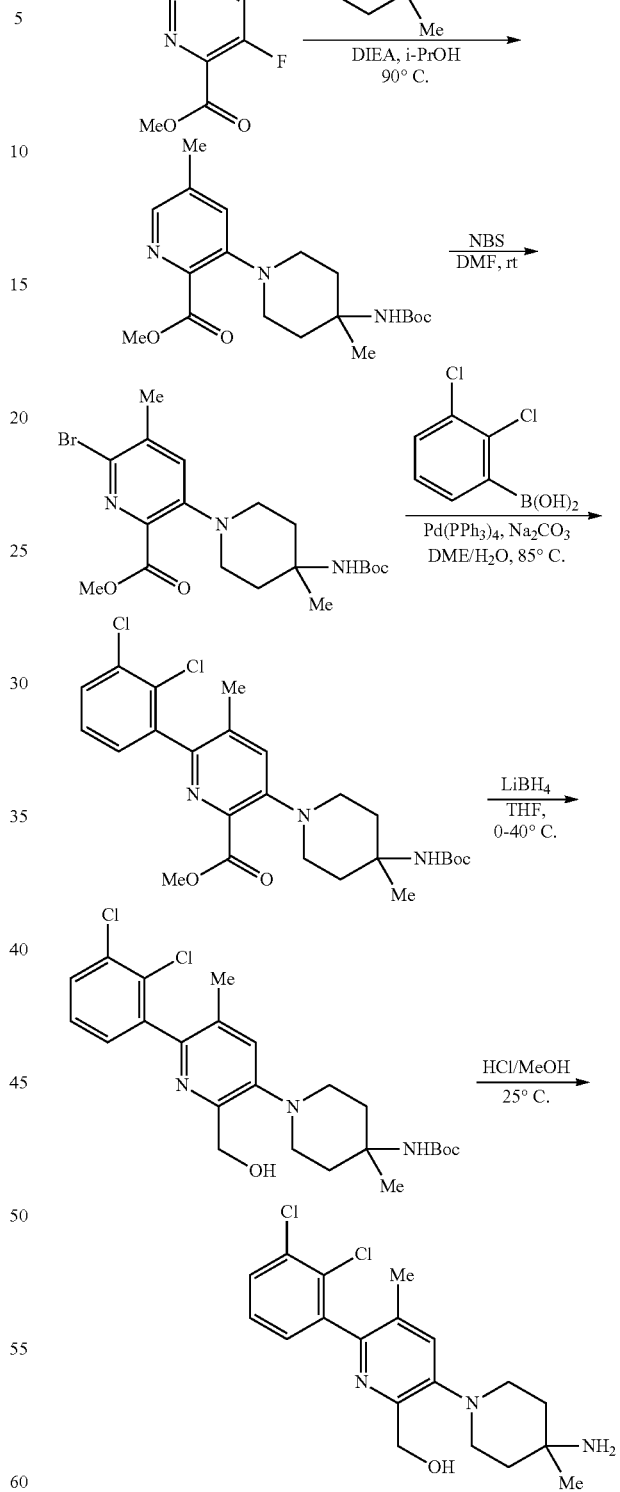

Step 1.

To a solution of 3-fluoro-5-methyl-pyridine-2-carboxylic acid (1.5 g, 9.6 mmol) in DMF (10 mL) was added $CH_3I$ (6.2 g, 43.5 mmol, 2.7 mL) and $K_2CO_3$ (3.6 g, 26.1 mmol). The reaction mixture was stirred at 25° C. for 16 hrs. The reaction was diluted with water and extracted with EtOAc. The combined organic phase was washed with brine, dried over anhydrous Na$_2$SO$_4$, filtered and concentrated under reduced pressure. The crude residue was purified by silica gel chromatography to give methyl 3-fluoro-5-methylpicolinate (1.4 g, 85% yield). LCMS (ESI): m/z [M+H] calculated for C$_8$H$_9$FNO$_2$: 170.0; found 170.0.

Step 2.

To a solution of methyl 3-fluoro-5-methylpicolinate (500 mg, 2.96 mmol) in i-PrOH (8 mL) was added tert-butyl N-(4-methyl-4-piperidyl)carbamate (696 mg, 3.25 mmol) and DIEA (1.9 g, 14.7 mmol, 2.6 mL). The reaction mixture was stirred at 90° C. for 16 hrs. All volatiles were removed under reduced pressure and the crude residue was purified by silica gel chromatography to give methyl 3-(4-((tert-butoxycarbonyl)amino)-4-methylpiperidin-1-yl)-5-methylpicolinate (650 mg, 60% yield). $^1$H NMR (400 MHz, Chloroform-d) δ ppm 8.08 (s, 1H) 7.21 (s, 1H) 4.36 (s, 1H) 3.95 (s, 3H) 3.14-2.94 (m, 5H) 2.34 (s, 3H) 2.09 (d, J=13.33 Hz, 2H) 1.86-1.74 (m, 2H) 1.44 (s, 9H) 1.41 (s, 3H). LCMS (ESI): m/z [M+H] calculated for C$_{19}$H$_{30}$N$_3$O$_4$: 364.2; found 364.3;

Step 3.

To a solution of methyl 3-(4-((tert-butoxycarbonyl)amino)-4-methylpiperidin-1-yl)-5-methylpicolinate (250 mg, 687 μmol) in DMF (1 mL) was added NBS (146 mg, 825 μmol) at 0° C. The reaction mixture was stirred at 0° C. for 5 min, then another portion of NBS (61 mg, 343 μmol) was added and the reaction mixture was stirred at 25° C. for 0.5 hr. The reaction mixture was quenched by addition aq. sat. Na$_2$SO$_3$ and H$_2$O. The mixture was filtered and concentrated under reduced pressure. The crude residue was purified by silica gel chromatography to give methyl 6-bromo-3-(4-((tert-butoxycarbonyl)amino)-4-methylpiperidin-1-yl)-5-methylpicolinate (175 mg, 57% yield). $^1$H NMR (400 MHz, Chloroform-d) δ ppm 7.25 (s, 1H) 4.33 (s, 1H) 3.93 (s, 3H) 3.11-2.93 (m, 4H) 2.38 (s, 3H) 2.09 (d, J=13.82 Hz, 2H) 1.82-1.74 (m, 2H) 1.44 (s, 9H) 1.40 (s, 3H). LCMS (ESI): m/z [M+H] calculated for C$_{19}$H$_{29}$BrN$_3$O$_4$: 442.0; found 442.2.

Step 4.

To a solution of methyl 6-bromo-3-(4-((tert-butoxycarbonyl)amino)-4-methylpiperidin-1-yl)-5-methylpicolinate (140 mg, 316 μmol) in DME (2 mL) was added (2,3-dichlorophenyl)boronic acid (91 mg, 474 μmol), Na$_2$CO$_3$ (67 mg, 633 μmol) in H$_2$O (0.4 mL) and Pd(PPh$_3$)$_4$ (37 mg, 32 μmol). The mixture was stirred at 85° C. for 16 hrs and then concentrated under reduced pressure. The crude residue was purified by silica gel chromatography to give methyl 3-(4-((tert-butoxycarbonyl)amino)-4-methylpiperidin-1-yl)-6-(2,3-dichlorophenyl)-5-methylpicolinate (85 mg, 52% yield). $^1$H NMR (400 MHz, Chloroform-d) δ ppm 7.54-7.45 (m, 1H) 7.32-7.18 (m, 3H) 4.38 (br s, 1H) 3.92 (s, 3H) 3.22-3.00 (m, 5H) 2.14 (s, 4H) 1.89-1.76 (m, 2H) 1.46 (s, 9H) 1.42 (s, 3H). LCMS (ESI): m/z [M+H] calculated for C$_{25}$H$_{32}$Cl$_2$N$_3$O$_4$: 508.0; found 508.1;

Step 5.

To a solution of methyl 3-(4-((tert-butoxycarbonyl)amino)-4-methylpiperidin-1-yl)-6-(2,3-dichlorophenyl)-5-methylpicolinate (80 mg, 157 μmol) in THF (2 mL) was added LiBH$_4$ (7 mg, 314 μmol) at 0° C. The reaction mixture was stirred at 40° C. for 1 hr. The reaction was quenched by the careful addition of MeOH (2 ml) and the solvent was removed under reduced pressure. The reaction mixture was concentrated to give tert-butyl (1-(6-(2,3-dichlorophenyl)-2-(hydroxymethyl)-5-methylpyridin-3-yl)-4-methylpiperidin-4-yl)carbamate (76 mg, crude) as a white solid which was directly used without further purification. LCMS (ESI): m/z [M+H] calculated for C$_{24}$H$_{32}$Cl$_2$N$_3$O$_3$: 480.0; found 480.0.

Step 6.

A mixture of tert-butyl (1-(6-(2,3-dichlorophenyl)-2-(hydroxymethyl)-5-methylpyridin-3-yl)-4-methylpiperidin-4-yl)carbamate (74 mg, 154 μmol) in HCl/MeOH (2 mL) was stirred at 25° C. for 1 hr. The reaction mixture was concentrated and the crude residue was purified by pre-HPLC to give (3-(4-amino-4-methylpiperidin-1-yl)-6-(2,3-dichlorophenyl)-5-methylpyridin-2-yl)methanol (17 mg, 29% yield). $^1$H NMR (400 MHz, Methanol-d$_4$) δ ppm 8.53 (br s, 1H) 7.62 (d, J=8.16 Hz, 1H) 7.57 (s, 1H) 7.40 (t, J=7.83 Hz, 1H) 7.26 (dd, J=7.61, 1.43 Hz, 1H) 4.72 (d, J=5.51 Hz, 2H) 3.19 (d, J=13.01 Hz, 2H) 3.11-2.98 (m, 2H) 2.12 (s, 3H) 2.07-1.87 (m, 4H) 1.48 (s, 3H). LCMS (ESI): m/z [M+H] calculated for C$_{19}$H$_{24}$Cl$_2$N$_3$O: 380.1; found 380.1.

Example 15. Synthesis of {6-[(2-amino-3-chloropyridin-4-yl)sulfanyl]-3-(4-amino-4-methylpiperidin-1-yl)pyridin-2-yl}methanol

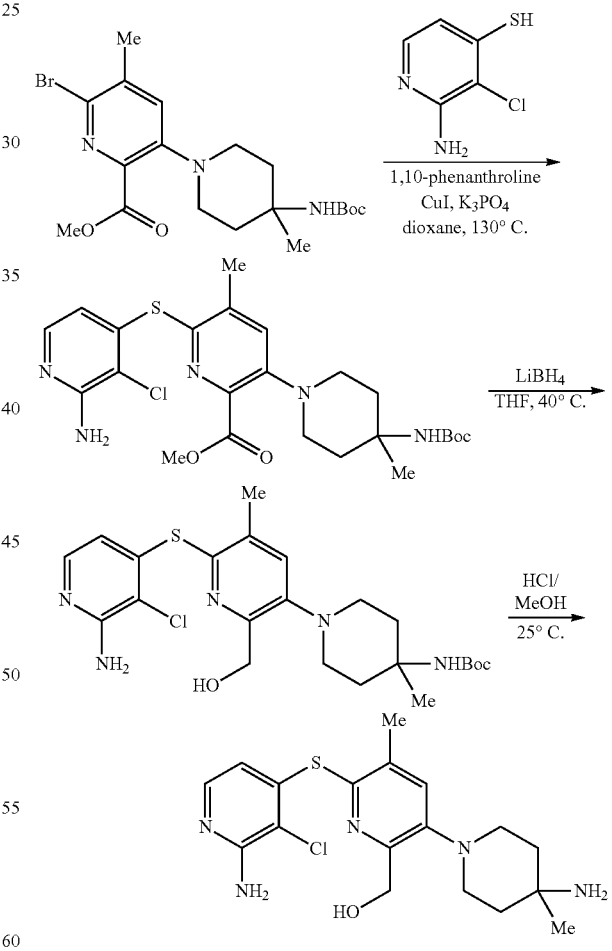

Step 1.

To a solution of 2-amino-3-chloro-pyridine-4-thiol (154 mg, 960 μmol) in dioxane (3 mL) was added methyl 6-bromo-3-(4-((tert-butoxycarbonyl)amino)-4-methylpiperidin-1-yl)-5-methylpicolinate (170 mg, 384 μmol), K$_3$PO$_4$ (163 mg, 768 μmol), 1,10-phenanthroline (14 mg, 77 μmol)

and CuI (7 mg, 38 µmol). The reaction mixture was stirred at 130° C. for 4 hrs and then cooled to room temperature, concentrated under reduced pressure and then purified by silica gel chromatography to give methyl 6-((2-amino-3-chloropyridin-4-yl)thio)-3-(4-((tert-butoxycarbonyl)amino)-4-methylpiperidin-1-yl)-5-methylpicolinate (82 mg, 41% yield). LCMS (ESI): m/z [M+H] calculated for $C_{24}H_{33}ClN_5O_4S$: 522.0; found 522.1.

Step 2.

To a solution of methyl 6-((2-amino-3-chloropyridin-4-yl)thio)-3-(4-((tert-butoxycarbonyl)amino)-4-methylpiperidin-1-yl)-5-methylpicolinate (80 mg, 157 µmol) in THF (2 mL) was added LiBH$_4$ (7 mg, 314 µmol) at 0° C. The reaction mixture was stirred at 40° C. for 1 hr upon which the reaction was quenched by careful addition of MeOH (2 ml) at room temperature. The mixture was concentrated to give tert-butyl (1-(6-((2-amino-3-chloropyridin-4-yl)thio)-2-(hydroxymethyl)-5-methylpyridin-3-yl)-4-methylpiperidin-4-yl)carbamate (76 mg, crude) which was directly used without further purification. LCMS (ESI): m/z [M+H] calculated for $C_{23}H_{33}ClN_5O3S$: 494.0; found 494.4.

Step 3.

A mixture of tert-butyl (1-(6-((2-amino-3-chloropyridin-4-yl)thio)-2-(hydroxymethyl)-5-methylpyridin-3-yl)-4-methylpiperidin-4-yl)carbamate (76 mg, 153 mol) in HCl/MeOH (2 mL) was stirred at 25° C. for 0.5 hr. The reaction mixture was concentrated under reduced pressure and then purified by pre-HPLC to give (6-((2-amino-3-chloropyridin-4-yl)thio)-3-(4-amino-4-methylpiperidin-1-yl)-5-methylpyridin-2-yl)methanol (11 mg, 17% yield) as a yellow solid $^1$H NMR (400 MHz, Methanol-d$_4$) δ ppm 7.87 (s, 1H) 7.65 (d, J=6.85 Hz, 1H) 6.29 (d, J=6.85 Hz, 1H) 4.82 (s, 2H) 3.38 (s, 2H) 3.24-3.13 (m, 2H) 2.50 (s, 3H) 2.20-1.95 (m, 4H) 1.53 (s, 3H). LCMS (ESI): m/z [M+H] calculated for $C_{18}H_{25}ClN_5OS$: 394.1; found 394.2.

Example 16. Synthesis of [5-[(2-amino-3-chloro-4-pyridyl)sulfanyl]-2-[(3S,4S)-4-amino-3-methyl-2-oxa-8-azaspiro[4.5]decan-8-yl]-6-methyl-3-pyridyl]methanol

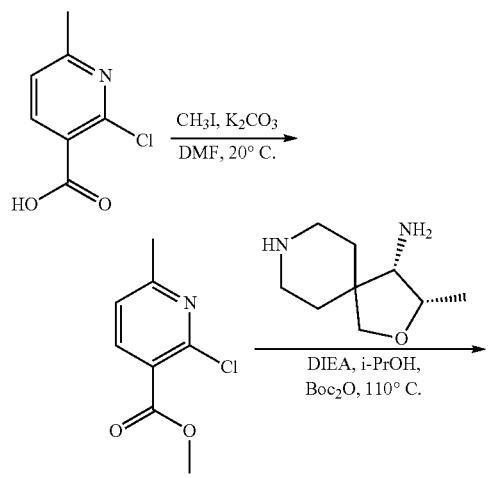

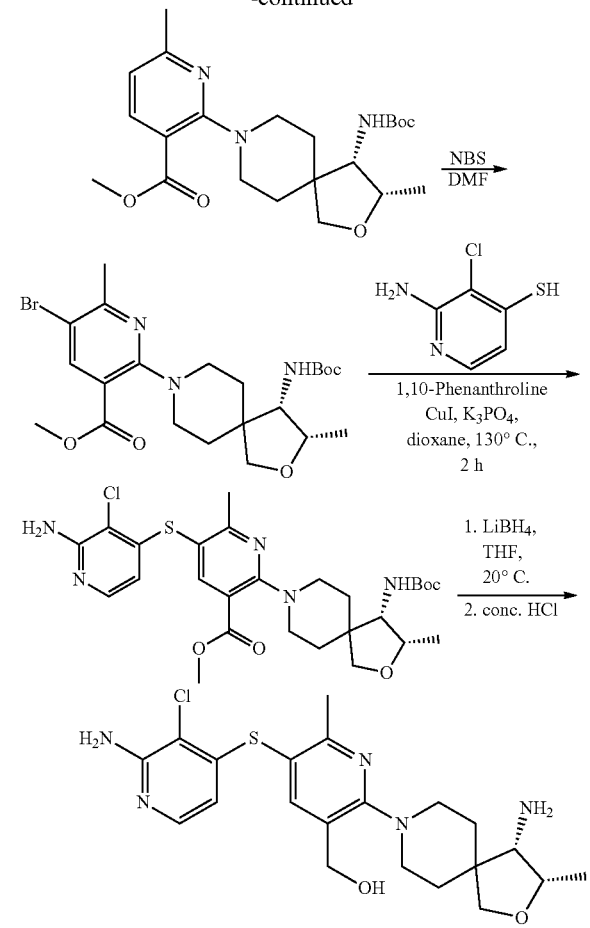

Step 1.

To a stirred solution of 2-chloro-6-methyl-pyridine-3-carboxylic acid (1 g, 5.83 mmol) in DMF (4 mL) was added K$_2$CO$_3$ (2.2 g, 15.74 mmol) and CH$_3$I (3.7 g, 26.23 mmol, 1.6 mL) at 20° C. The reaction mixture was stirred at 20° C. for 3 hrs. The reaction was diluted with water (40 mL) and extracted with EtOAc. The combined organic layers were dried over MgSO$_4$, filtered and the filtrate was concentrated under reduced pressure. The resulting residue was purified by silica gel chromatography to afford methyl 2-chloro-6-methyl-pyridine-3-carboxylate (1 g, 92% yield) as a white solid. $^1$H NMR (400 MHz, Methanol-d$_4$) δ ppm 8.13 (d, J=7.89 Hz, 1H) 7.49-7.22 (m, 1H) 3.91 (s, 3H) 2.54 (s, 3H). LCMS (ESI): m/z [M+H] calculated for $C_8H_9ClNO_2$: 186.0; found 186.1.

Step 2.

To a solution of methyl 2-chloro-6-methyl-pyridine-3-carboxylate (0.14 g, 754 µmol) in i-PrOH (4 mL) was added (3S,4S)-3-methyl-2-oxa-8-azaspiro[4.5]decan-4-amine (220 mg, 905.14 µmol, 2 HCl salt), and DIEA (975 mg, 7.54 mmol, 1.3 mL) at 20° C. The reaction mixture was stirred at 110° C. for 12 hrs. To the reaction mixture was added Boc$_2$O (658 mg, 3.02 mmol, 693 µL) and the mixture was stirred at 20° C. for 2 hrs. The mixture was diluted with water (15 mL) and extracted with EtOAc. The combined organic fractions were washed with brine, dried with Na$_2$SO$_4$, filtered and concentrated under reduced pressure. The resulting residue was purified by silica gel chromatography to afford methyl 2-[(3S,4S)-4-(tert-butoxycarbonylamino)-3-methyl-2-oxa- 8-azaspiro[4.5]decan-8-yl]-6-methyl-pyridine-3-carboxylate (90 mg, 28% yield) as a white solid. $^1$H NMR (400 MHz, Methanol-d$_4$) δ ppm 7.86 (d, J=7.83 Hz, 1H) 6.96-6.81 (m, 1H) 6.68-6.57 (m, 1H) 4.21 (dt, J=11.34, 5.52 Hz, 1H) 3.96-3.90 (m, 1H) 3.84 (s, 3H) 3.73-3.68 (m, 1H) 3.66-3.62 (m, 1H) 3.59-3.55 (m, 1H) 3.51-3.43 (m, 1H) 3.34 (s, 3H) 3.22-3.09 (m, 1H) 2.43 (s, 3H) 1.85-1.71 (m, 2H) 1.64-1.56 (m, 2H) 1.45-1.44 (m, 9H) 1.14-1.10 (m, 3H). LCMS (ESI): m/z [M+H] calculated for C$_{22}$H$_{34}$N$_3$O$_5$: 420.2; found 420.4

Step 3.

To a solution of methyl 2-[(3S,4S)-4-(tert-butoxycarbonylamino)-3-methyl-2-oxa-8-azaspiro[4.5]decan-8-yl]-6-methyl-pyridine-3-carboxylate (0.18 g, 429 μmol) in DMF (5 mL) was added NBS (84 mg, 472 μmol) at 20° C. The reaction was stirred at 20° C. for 1 hr. The mixture was quenched with sat. aq. Na$_2$S$_2$O$_3$ and the mixture was extracted with EtOAc. The combined organic layers were washed with brine, dried over Na$_2$SO$_4$, and filtered. The filtrate was concentrated under reduced pressure. The remaining residue was purified by silica gel chromatography to afford methyl 5-bromo-2-[(3S,4S)-4-(tert-butoxycarbonylamino)-3-methyl-2-oxa-8-azaspiro[4.5]decan-8-yl]-6-methyl-pyridine-3-carboxylate (0.14 g, 65% yield) as a white solid. $^1$H NMR (400 MHz, Methanol-d$_4$) δ ppm 8.09-7.88 (m, 1H) 4.28-4.17 (m, 1H) 3.95-3.92 (m, 1H) 3.91-3.88 (m, 1H) 3.85 (s, 3H) 3.73-3.68 (m, 1H) 3.66-3.61 (m, 1H) 3.59-3.56 (m, 1H) 3.52-3.43 (m, 2H) 3.40-3.33 (m, 1H) 3.24-3.13 (m, 2H) 2.49 (s, 3H) 1.76-1.68 (m, 2H) 1.62-1.56 (m, 2H) 1.45-1.44 (m, 9H) 1.14-1.10 (m, 3H). LCMS (ESI): m/z [M+H] calculated for C$_{22}$H$_{33}$BrN$_3$O$_5$: 498.2, 500.2; found 498.2, 500.2.

Step 4.

A mixture of methyl 5-bromo-2-[(3S,4S)-4-(tert-butoxycarbonylamino)-3-methyl-2-oxa-8-azaspiro[4.5]decan-8-yl]-6-methyl-pyridine-3-carboxylate (60 mg, 120 μmol), 2-amino-3-chloro-pyridine-4-thiol (39 mg, 241 μmol), 1,10-Phenanthroline (4 mg, 24 μmol), K$_3$PO$_4$ (51 mg, 241 μmol) and CuI (2 mg, 12 μmol) in dioxane (2 mL) was heated at 140° C. for 48 hrs. The mixture was diluted with water and the mixture was extracted with EtOAc. The combined organic fractions were washed with brine, dried with Na$_2$SO$_4$, filtered and the filtrate was concentrated under reduced pressure. The resulting residue was purified by silica gel chromatography to afford methyl 5-[(2-amino-3-chloro-4-pyridyl)sulfanyl]-2-[(3S,4S)-4-(tert-butoxycarbonylamino)-3-methyl-2-oxa-8-azaspiro[4.5]decan-8-yl]-6-methyl-pyridine-3-carboxylate (20 mg, 29% yield) as a white solid. LCMS (ESI): m/z [M+H] calculated for C$_{27}$H$_{37}$ClN$_5$O$_5$S: 578.2; found 578.3.

Step 5.

To a solution of methyl 5-[(2-amino-3-chloro-4-pyridyl)sulfanyl]-2-[(3S,4S)-4-(tert-butoxycarbonylamino)-3-methyl-2-oxa-8-azaspiro[4.5]decan-8-yl]-6-methyl-pyridine-3-carboxylate (20 mg, 35 μmol) in THF (1 mL) was added LiBH$_4$ (2 mg, 104 μmol) at 20° C. The reaction was stirred at 50° C. for 12 hrs. To the reaction mixture was added HCl (0.3 mL) at 20° C., and the reaction was stirred at 30° C. for 2 hrs. The mixture was adjusted to pH=7 with NaHCO$_3$, filtered and the filtrate was concentrated under reduced pressure. The remaining residue was purified by prep-HPLC to afford [5-[(2-amino-3-chloro-4-pyridyl)sulfanyl]-2-[(3S,4S)-4-amino-3-methyl-2-oxa-8-azaspiro[4.5]decan-8-yl]-6-methyl-3-pyridyl]methanol (4.3 mg, 28% yield) as a white solid. $^1$H NMR (400 MHz, Methanol-d$_4$) δ ppm 8.63-8.40 (m, 1H) 7.86-7.80 (m, 1H) 7.58-7.53 (m, 1H) 5.76-5.73 (m, 1H) 4.60-4.52 (m, 2H) 4.32-4.22 (m, 1H) 3.94-3.87 (m, 1H) 3.82-3.75 (m, 1H) 3.60-3.35 (m, 2H) 3.25 (br d, J=3.67 Hz, 1H) 3.11-2.93 (m, 2H) 2.44 (s, 3H) 1.99-1.87 (m, 2H) 1.85-1.77 (m, 1H) 1.70 (br d, J=11.74 Hz, 1H) 1.27 (d, J=6.48 Hz, 3H). LCMS (ESI): m/z [M+H] calculated for C$_{21}$H$_{29}$ClN$_5$O$_2$S: 450.2; found 450.2.

Example 17. Synthesis of {2-[(3S,4S)-4-amino-3-methyl-2-oxa-8-azaspiro[4.5]decan-8-yl]-5-(2,3-dichlorophenyl)-6-methylpyridin-3-yl}methanol

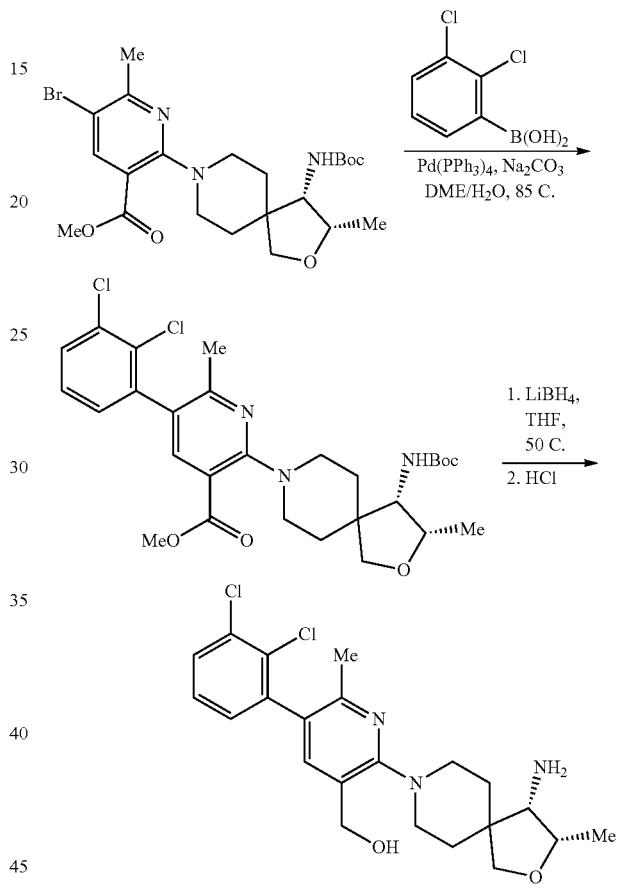

Step 1.

To a solution of methyl 5-bromo-2-[(3S,4S)-4-(tert-butoxycarbonylamino)-3-methyl-2-oxa-8-azaspiro[4.5]decan-8-yl]-6-methyl-pyridine-3-carboxylate (50 mg, 100 μmol) in DME (1 mL) was added (2,3-dichlorophenyl)boronic acid (29 mg, 151 μmol), Na$_2$CO$_3$ (21 mg, 201 μmol), H$_2$O (0.2 mL) and Pd(PPh$_3$)$_4$ (23 mg, 20 μmol). The reaction was stirred at 85° C. for 3 hrs. After cooling to room temperature the mixture was diluted with water and the organic layer was extracted with ethyl acetate. The combined organic phases were washed with brine and then dried over Na$_2$SO$_4$. After filtration the solvent was removed under reduced pressure and the crude residue was purified by silica gel chromatography to give methyl 2-[(3S,4S)-4-(tert-butoxycarbonylamino)-3-methyl-2-oxa-8-azaspiro[4.5]decan-8-yl]-5-(2,3-dichlorophenyl)-6-methyl-pyridine-3-carboxylate (30 mg, 53% yield). $^1$H NMR (400 MHz, Methanol-d$_4$) δ ppm 7.72 (s, 1H) 7.57 (br d, J=6.61 Hz, 1H) 7.36 (s, 1H) 7.23 (br d, J=7.72 Hz, 1H) 6.94 (br d, J=9.92 Hz, 1H) 4.27-4.20 (m, 2H) 3.97 (br s, 1H) 3.85 (s, 3H) 3.74 (br d, J=9.70 Hz, 2H) 3.67

(br d, J=8.16 Hz, 1H) 3.48 (br s, 2H) 2.18 (s, 3H) 1.78-1.72 (m, 2H) 1.60 (br s, 3H) 1.45 (br d, J=3.31 Hz, 9H) 1.15-1.11 (m, 3H). LCMS (ESI): m/z [M+H] calculated for $C_{28}H_{36}Cl_2N_3O_4$: 564.2; found 564.4.

Step 2.

To a solution of methyl 2-[(3S,4S)-4-(tert-butoxycarbonylamino)-3-methyl-2-oxa-8-azaspiro[4.5]decan-8-yl]-5-(2,3-dichlorophenyl)-6-methyl-pyridine-3-carboxylate (30 mg, 53 µmol) in THF (1 mL) was added LiBH$_4$ (4 mg, 159 µmol). The reaction was stirred at 50° C. for 2 hrs. HCl (conc.) was then added and the mixture was stirred at 20° C. for 3 hrs. The mixture was adjusted to pH=7 with NaHCO$_3$, filtered and the solvent removed under reduced pressure. The crude residue was purified by preparative HPLC to give [2-[(3S,4S)-4-amino-3-methyl-2-oxa-8-azaspiro[4.5]decan-8-yl]-5-(2,3-dichlorophenyl)-6-methyl-3-pyridyl]methanol (3 mg, 13% yield). 1H NMR (400 MHz, Methanol-d$_4$) δ ppm 7.57 (dd, J=8.05, 1.43 Hz, 1H) 7.52 (s, 1H) 7.36 (t, J=7.83 Hz, 1H) 7.21 (dd, J=7.72, 1.32 Hz, 1H) 4.63 (s, 2H) 4.30-4.23 (m, 1H) 3.88 (d, J=8.82 Hz, 1H) 3.77 (d, J=8.82 Hz, 1H) 3.43-3.34 (m, 2H) 3.23-2.88 (m, 3H) 2.19 (s, 3H) 1.92 (br d, J=5.73 Hz, 2H) 1.81-1.69 (m, 2H) 1.25 (d, J=6.62 Hz, 3H). LCMS (ESI): m/z [M+H] calculated for $C_{22}H_{28}Cl_2N_3O_2$: 436.2; found 436.2.

Example 18. Synthesis of 5-[(3S,4S)-4-amino-3-methyl-2-oxa-8-azaspiro[4.5]decan-8-yl]-2-(2,3-dichlorophenyl)-6-(hydroxymethyl)pyridin-3-ol

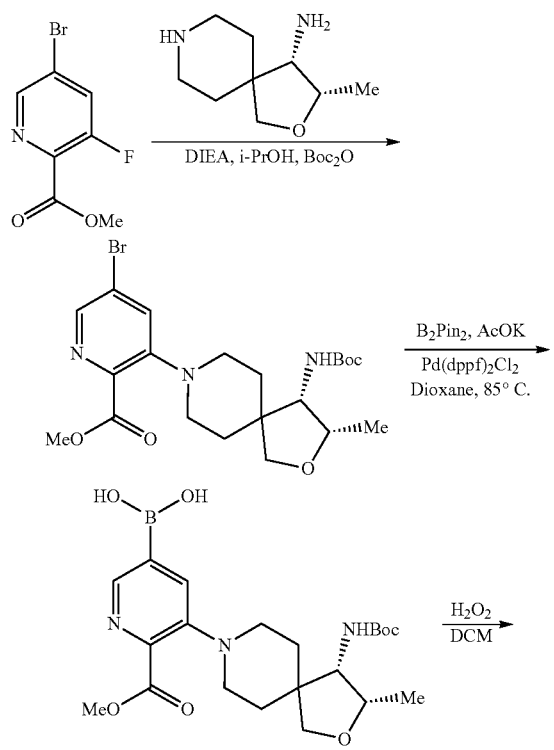

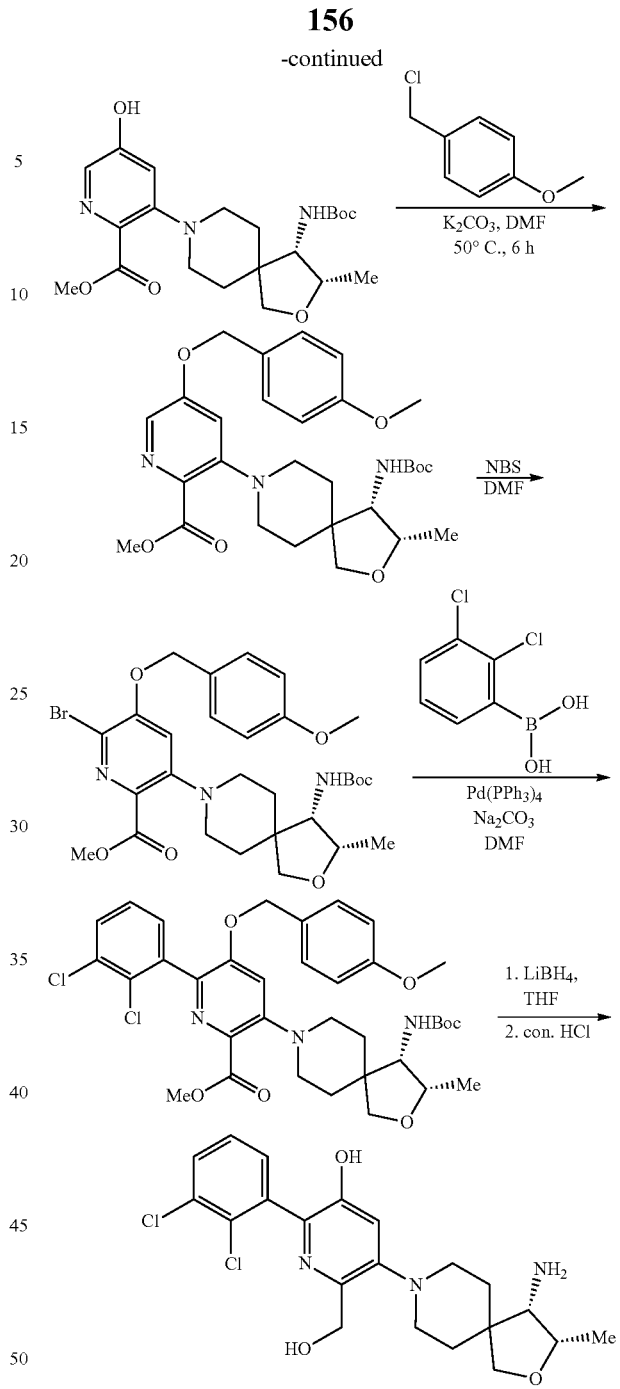

Step 1.

To a solution of methyl 5-bromo-3-fluoro-pyridine-2-carboxylate (0.5 g, 2.14 mmol) in i-PrOH (10 mL) was added (3S,4S)-3-methyl-2-oxa-8-azaspiro[4.5]decan-4-amine (649 mg, 2.67 mmol, HCl salt) and DIEA (2.8 g, 21.37 mmol, 3.7 mL) at 20° C. The reaction mixture was stirred at 110° C. for 12 hrs. Boc$_2$O (933 mg, 4.27 mmol, 982 µL) was then added to this mixture, and the resulting mixture was stirred at 20° C. for 2 hrs. The mixture was partitioned between water and EtOAc and the organic layer was washed with brine, dried with Na$_2$SO$_4$, filtered and concentrated under reduced pressure. The resulting residue was purified by column chromatography to afford methyl 5-bromo-3-[(3S,4S)-4-(tert-butoxycarbonylamino)-3-methyl-2-oxa-8-azaspiro[4.5]decan-8-yl]pyridine-2-carboxylate (1 g, 97% yield) as a white solid. $^{1}$H NMR (400 MHz, Methanol-$d_4$) δ ppm 8.22 (s, 1H) 7.79 (s, 1H) 4.28-4.18 (m, 1H) 3.92 (s, 3H) 3.74-3.55 (m, 2H) 3.24-3.14 (m, 1H) 3.10-3.00 (m, 2H) 2.96-2.87 (m, 1H) 1.92-1.73 (m, 3H) 1.70-1.58 (m, 2H) 1.46 (s, 9H) 1.13 (d, J=6.39 Hz, 3H). LCMS (ESI): m/z [M+H] calculated for $C_{21}H_{31}BrN_3O_5$: 484.1; found 484.1.

Step 2.

To a solution of methyl 5-bromo-3-[(3S,4S)-4-(tert-butoxycarbonylamino)-3-methyl-2-oxa-8-azaspiro[4.5]decan-8-yl]pyridine-2-carboxylate (1 g, 2.06 mmol) in dioxane (15 mL) was added 4,4,5,5-tetramethyl-2-(4,4,5,5-tetramethyl-1,3,2-dioxaborolan-2-yl)-1,3,2-dioxaborolane (786 mg, 3.10 mmol), KOAc (405 mg, 4.13 mmol) and Pd(dppf)$Cl_2 \cdot CH_2Cl_2$ (169 mg, 206 μmol) at 20° C. The reaction mixture was stirred at 85° C. for 2 hrs. The reaction mixture was filtered and the filtrate was purified by reversed-phase column chromatography to afford [5-[(3S,4S)-4-(tert-butoxycarbonylamino)-3-methyl-2-oxa-8-azaspiro[4.5]decan-8-yl]-6-methoxycarbonyl-3-pyridyl]boronic acid (0.4 g, 43% yield) as a white solid. $^{1}$H NMR (400 MHz, Methanol-$d_4$) δ ppm 8.26 (br s, 1H) 7.87-7.72 (m, 1H) 6.88 (br d, J=10.58 Hz, 1H) 4.26-4.17 (m, 1H) 3.92 (s, 3H) 3.75-3.71 (m, 1H) 3.69-3.64 (m, 1H) 3.34 (s, 2H) 3.21-3.12 (m, 1H) 3.05 (br s, 2H) 2.94-2.82 (m, 1H) 1.92-1.75 (m, 3H) 1.70-1.60 (m, 1H) 1.46 (s, 9H) 1.13 (d, J=6.17 Hz, 3H). LCMS (ESI): m/z [M+H] calculated for $C_{21}H_{33}BN_3O_7$: 450.2; found 450.4.

Step 3.

$H_2O_2$ (303 mg, 2.67 mmol, 257 μL, 30% purity) was added slowly to the solution of [5-[(3S,4S)-4-(tert-butoxycarbonylamino)-3-methyl-2-oxa-8-azaspiro[4.5]decan-8-yl]-6-methoxycarbonyl-3-pyridyl]boronic acid (0.4 g, 890 μmol) in DCM (2 mL) at 0° C. The reaction mixture was stirred at 20° C. for 5 hrs. The mixture was quenched with sat. $Na_2S_2O_3$ aqueous (40 mL) and adjusted to pH<7 with 1N HCl. The mixture was extracted with EtOAc and the organic layer was washed with brine, dried over $Na_2SO_4$, filtered and concentrated under reduced pressure. The remaining residue was purified by column chromatography to afford methyl 3-[(3S,4S)-4-(tert-butoxycarbonylamino)-3-methyl-2-oxa-8-azaspiro[4.5]decan-8-yl]-5-hydroxy-pyridine-2-carboxylate (0.27 g, 72% yield) as a white solid. $^{1}$H NMR (400 MHz, Methanol-$d_4$) δ ppm 7.70 (s, 1H) 6.94-6.90 (s, 1H) 4.26-4.19 (m, 1H) 3.98-3.92 (m, 1H) 3.88 (s, 3H) 3.74-3.69 (m, 1H) 3.65-3.61 (m, 1H) 3.16-3.09 (m, 1H) 3.05-2.96 (m, 2H) 2.90-2.81 (m, 1H) 1.93-1.78 (m, 3H) 1.71-1.62 (m, 1H) 1.46 (s, 9H) 1.13 (d, J=6.39 Hz, 3H). LCMS (ESI): m/z [M+H] calculated for $C_{21}H_{32}N_3O_6$: 422.2; found 422.4.

Step 4.

To a solution of methyl 3-[(3S,4S)-4-(tert-butoxycarbonylamino)-3-methyl-2-oxa-8-azaspiro[4.5]decan-8-yl]-5-hydroxy-pyridine-2-carboxylate (0.27 g, 641 μmol) in DMF (6 mL) was added 1-(chloromethyl)-4-methoxy-benzene (150 mg, 961 μmol, 131 μL) and $K_2CO_3$ (266 mg, 1.92 mmol) at 25° C. The reaction was stirred at 50° C. for 6 hrs. The mixture was diluted with water (15 ml), extracted with EtOAc. The combined organic fractions were washed with brine, dried with $Na_2SO_4$, filtered and concentrated under reduced pressure. The resulting residue was purified by column chromatography to afford methyl 3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.33 g, 95% yield) as a white solid. $^{1}$H NMR (400 MHz, Methanol-$d_4$) δ ppm 7.84 (s, 1H) 7.39-7.35 (m, 2H) 7.09 (s, 1H) 6.96-6.92 (m, 2H) 5.17-5.10 (m, 2H) 4.26-4.21 (m, 1H) 3.97-3.94 (m, 1H) 3.89 (s, 3H) 3.79 (s, 3H) 3.73-3.69 (m, 1H) 3.66-3.61 (m, 1H) 3.20-3.11 (m, 1H) 3.07-3.00 (m, 2H) 2.88 (br s, 1H) 1.94-1.77 (m, 4H) 1.70-1.61 (m, 1H) 1.46 (s, 9H) 1.13 (d, J=6.14 Hz, 3H). LCMS (ESI): m/z [M+H] calculated for $C_{29}H_{40}N_3O_7$: 542.3; found 542.4.

Step 5.

To a solution of methyl 3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.23 g, 424 μmol) in DMF (3 mL) was added NBS (76 mg, 425 μmol) at 20° C. The reaction was stirred at 20° C. for 5 min. The mixture was quenched with sat. $Na_2S_2O_3$ aqueous and the resulting mixture was extracted with EtOAc. The organic layer was washed with brine, dried over $Na_2SO_4$, filtered and concentrated under reduced pressure. The resulting residue was purified by column chromatography to afford methyl 6-bromo-3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.3 g, 85% yield) as a white solid. $^{1}$H NMR (400 MHz, Methanol-$d_4$) δ ppm 7.95 (s, 1H) 7.39 (d, J=8.60 Hz, 2H) 7.10-7.05 (m, 1H) 6.94 (d, J=8.60 Hz, 2H) 5.19 (s, 2H) 4.26-4.19 (m, 1H) 3.98-3.92 (m, 1H) 3.87 (s, 3H) 3.80 (s, 3H) 3.73-3.69 (m, 1H) 3.62 (d, J=8.60 Hz, 1H) 3.20-3.12 (m, 1H) 3.03 (ddd, J=11.74, 7.99, 3.20 Hz, 2H) 2.93-2.87 (m, 1H) 2.68 (s, 2H) 1.91-1.73 (m, 3H) 1.63 (dt, J=12.79, 3.97 Hz, 1H) 1.46 (s, 9H) 1.19-1.11 (m, 3H). LCMS (ESI): m/z [M+H] calculated for $C_{29}H_{39}BrN_3O_7$: 620.2; found 620.3.

Step 6.

To a solution of methyl 6-bromo-3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.1 g, 161.15 μmol) in DME (2 mL) was added (2,3-dichlorophenyl)boronic acid (46 mg, 242 μmol), $Na_2CO_3$ (34 mg, 322 μmol), $H_2O$ (0.4 mL) and Pd(PPh$_3$)$_4$ (37 mg, 32 μmol) at 20° C. The reaction mixture was stirred at 85° C. for 3 hrs. The mixture was diluted with water (5 ml) and the organic layer was extracted with EtOAc. The combined organic fractions were washed with brine, dried with $Na_2SO_4$, filtered and concentrated under reduced pressure. The resulting residue was purified by silica gel chromatography to afford methyl 3-[(3S,4S)-4-(tert-butoxycarbonylamino)-3-methyl-2-oxa-8-azaspiro[4.5]decan-8-yl]-6-(2,3-dichlorophenyl)-5-[(4-methoxyphenyl)methoxy]pyridine-2-carboxylate (0.05 g, 45% yield) as a white solid. $^{1}$H NMR (400 MHz, Methanol-$d_4$) δ ppm 7.57-7.54 (m, 1H) 7.33 (t, J=7.72 Hz, 1H) 7.27 (dd, J=7.61, 1.65 Hz, 1H) 7.24-7.21 (m, 3H) 6.86 (d, J=8.60 Hz, 2H) 5.12 (s, 2H) 4.27-4.23 (m, 1H) 3.98 (br d, J=4.19 Hz, 1H) 3.87 (s, 3H) 3.76 (s, 3H) 3.73 (br d, J=8.38 Hz, 1H) 3.66 (br d, J=8.60 Hz, 1H) 3.23 (br s, 1H) 3.11 (br d, J=10.58 Hz, 2H) 2.97 (br d, J=12.35 Hz, 1H) 1.94-1.80 (m, 3H) 1.68 (br s, 1H) 1.48 (s, 8H) 1.15 (d, J=6.39 Hz, 3H). LCMS (ESI): m/z [M+H] calculated for $C_{35}H_{42}Cl_2N_3O_7$: 686.2; found 686.3

Step 7.

To a solution of methyl 3-[(3S,4S)-4-(tert-butoxycarbonylamino)-3-methyl-2-oxa-8-azaspiro[4.5]decan-8-yl]-6-(2,3-dichlorophenyl)-5-[(4-methoxyphenyl)methoxy]pyridine-2-carboxylate (50 mg, 73 μmol) in THF (1 mL) was added LiBH$_4$ (5 mg, 219 μmol) at 20° C. The reaction was stirred at 50° C. for 2 hrs. To the mixture was added HCl (0.3 mL) at 20° C., and the resulting mixture was stirred at 50° C. for 2 hrs. The mixture was adjusted to pH=7 with NaHCO$_3$, filtered and the filtrate was concentrated under reduced pressure. The remaining residue was purified by prep-HPLC to afford 5-[(3S,4S)-4-amino-3-methyl-2-oxa-8-azaspiro

[4.5]decan-8-yl]-2-(2,3-dichlorophenyl)-6-(hydroxymethyl)pyridin-3-ol (6 mg, 18% yield) as a white solid. $^1$H NMR (400 MHz, Methanol-$d_4$) δ ppm 8.49 (br s, 1H) 7.57 (d, J=8.33 Hz, 1H) 7.39-7.28 (m, 2H) 7.06 (s, 1H) 4.67 (s, 2H) 4.32-4.24 (m, 1H) 3.93 (d, J=9.21 Hz, 1H) 3.83 (d, J=8.77 Hz, 1H) 3.37 (br d, J=3.95 Hz, 1H) 3.26-3.16 (m, 2H) 2.88-2.72 (m, 2H) 2.05-1.96 (m, 2H) 1.93-1.87 (m, 1H) 1.74 (br d, J=12.28 Hz, 1H) 1.30 (d, J=6.14 Hz, 3H). LCMS (ESI): m/z [M+H] calculated for $C_{21}H_{26}Cl_2N_3O_3$: 438.1; found 438.1.

Example 19. Synthesis of 2-[(2-amino-3-chloro-4-pyridyl)sulfanyl]-5-[(3S,4S)-4-amino-3-methyl-2-oxa-8-azaspiro[4.5]decan-8-yl]-6-(hydroxymethyl)pyridin-3-ol

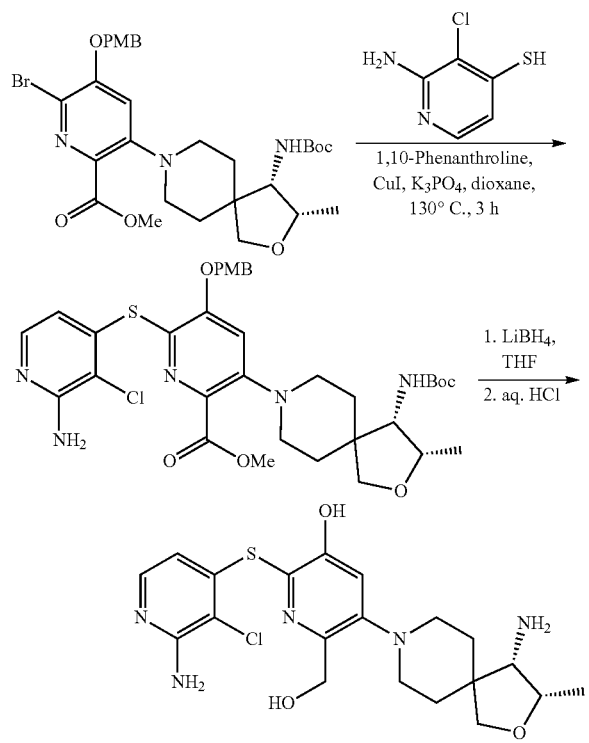

Step 1.

A solution of Methyl 6-bromo-3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.2 g, 322 μmol), 2-amino-3-chloro-pyridine-4-thiol (104 mg, 645 μmol), 1,10-Phenanthroline (12 mg, 65 μmol), $K_3PO_4$ (137 mg, 645 μmol) and CuI (6 mg, 32 μmol) in dioxane (4 mL) was heated at 130° C. for 3 hrs. The mixture was diluted with water (15 mL), and extracted with EtOAc. The combined organic fractions were washed with brine, dried with $Na_2SO_4$, filtered and concentrated under reduced pressure. The resulting residue was purified by silica gel chromatography to afford methyl 6-[(2-amino-3-chloro-4-pyridyl)sulfanyl]-3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.1 g, 44% yield) as a white solid. $^1$H NMR (400 MHz, Methanol-$d_4$) δ ppm 7.15-7.09 (m, 3H) 6.94-6.90 (m, 1H) 6.85-6.81 (m, 2H) 5.99 (br s, 1H) 5.10 (s, 2H) 4.27-4.20 (m, 1H) 4.00-3.94 (m, 1H) 3.88 (s, 3H) 3.77 (s, 3H) 3.72 (d, J=8.82 Hz, 1H) 3.66-3.62 (m, 1H) 3.34 (s, 1H) 3.25 (br d, J=7.94 Hz, 1H) 3.17-3.10 (m, 2H) 1.90-1.79 (m, 3H) 1.72-1.62 (m, 1H) 1.47 (s, 9H) 1.15 (d, J=6.39 Hz, 3H). LCMS (ESI): m/z [M+H] calculated for $C_{34}H_{43}ClN_5O_7S$: 700.2; found 700.3.

Step 2.

To a solution of methyl 6-[(2-amino-3-chloro-4-pyridyl)sulfanyl]-3-[(3S,4S)-4-(tert-butoxycarbonylamino)-3-methyl-2-oxa-8-azaspiro[4.5]decan-8-yl]-5-[(4-methoxyphenyl)methoxy]pyridine-2-carboxylate (0.1 g, 143 μmol) in THF (3 mL) was added LiBH$_4$ (9 mg, 428 μmol) at 20° C. The reaction was stirred at 50° C. for 2 hrs. To this mixture was added HCl (1 mL) at 20° C., and the reaction was stirred at 30° C. for 4 hrs. The reaction mixture was adjusted to pH=7 with NaHCO$_3$, filtered and the resultant filtrate was concentrated under reduced pressure. The remaining residue was purified by prep-HPLC to afford 2-[(2-amino-3-chloro-4-pyridyl)sulfanyl]-5-[(3S,4S)-4-amino-3-methyl-2-oxa-8-azaspiro[4.5]decan-8-yl]-6-(hydroxymethyl)pyridin-3-ol (8 mg, 12% yield) as a white solid. $^1$H NMR (400 MHz, Methanol-$d_4$) δ ppm 7.52 (d, J=5.51 Hz, 1H) 7.05-6.93 (m, 1H) 5.93 (d, J=5.73 Hz, 1H) 4.61 (s, 2H) 4.32-4.17 (m, 1H) 3.85 (d, J=8.82 Hz, 1H) 3.73 (d, J=8.82 Hz, 1H) 3.26-3.05 (m, 3H) 2.94-2.71 (m, 2H) 2.02-1.86 (m, 2H) 1.83-1.65 (m, 2H) 1.23 (d, J=6.39 Hz, 3H). LCMS (ESI): m/z [M+H] calculated for $C_{20}H_{27}ClN_5O_3S$: 452.1; found 452.1.

Additional Compounds

Compounds of the present disclosure were prepared according to the synthetic schemes provided herein. The table below shows compounds and the mass spectrometry results.

| Structure | M + 1 found |
|---|---|
| 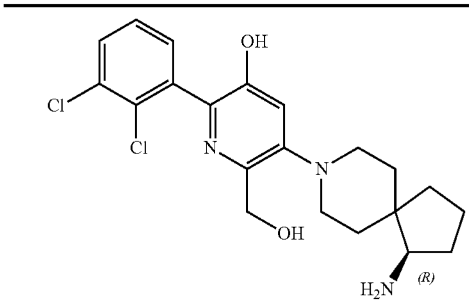 | 422.1 |
| 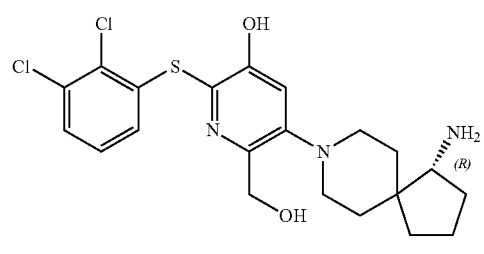 | 454.1 |
| 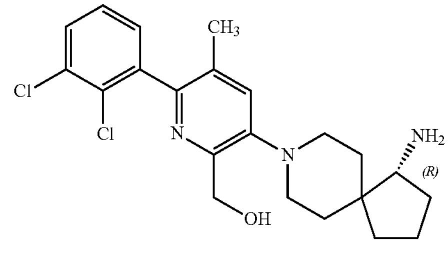 | 420.1 |

-continued

| Structure | M + 1 found |
|---|---|
| [structure with Cl, Cl, CH3, S, pyridine, piperidine-spirocyclopentane-NH2 (R)] | 422.1 |
| [structure with Cl, Cl, CH3, pyridine, piperidine-spirocyclopentane-NH2 (R)] | 390.1 |
| [structure with Cl, Cl, OH, pyridine, piperidine-spirocyclopentane-NH2 (R)] | 392.3 |
| [structure with OH, S, Cl, Cl, pyridine, piperidine-NH2, CH3] | 384.1 |
| [structure with OH, S, Cl, Cl, pyridine, piperidine-spirocyclopentane-NH2 (R)] | 424.1 |

Biological Examples—Shp2 Allosteric Inhibition Assay

Without wishing to be bound by theory, SHP is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 μL and the following assay buffer conditions: 50 mM HEPES, pH 7.2, 100 mM NaCl, 0.5 mM EDTA, 0.05% P-20, 1 mM DTT.

The inhibition of SHP2 by compounds of the disclosure (concentrations varying from 0.00005-10 μM) was monitored using an assay in which 0.2 nM of SHP2 was incubated with 0.5 μM of Activating Peptide 1 (sequence: $H_2$N-LN (pY)IDLDLV(dPEG8)LST (pY)ASINFQK-amide) or Activating Peptide 2 (sequence: $H_2$N-LN(pY)AQLWHA (dPEG8) LTI(pY)ATIRRF-amide). After 30-60-minutes incubation at 25° C., the surrogate substrate DiFMUP (Invitrogen, Cat #D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized $IC_{50}$ regression curve fitting with control based normalization.

In some embodiments, compounds of the disclosure tested in the assay described above demonstrated an activity of less than 1000 nM. In some embodiments, compounds of the disclosure tested in the assay described above demonstrated an activity of about 10 nM to about 100 nM. In some embodiments, compounds of the disclosure tested in the assay described above demonstrated an activity of 10 nM to 100 nM. In some embodiments, compounds of the disclosure tested in the assay described above demonstrated an activity of less than 10 nM.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 1 nM to about 10 nM of a compound of the disclosure. In some embodiments, SHP2 is inhibited after treatment with about 10 nM to about 100 nM of a compound of the disclosure. In some embodiments, SHP2 is inhibited after treatment with about 100 nM to about 10 μM of a compound of the disclosure.

Using the above-protocol, SHP2 inhibition measured as set forth in Table 1.

TABLE 1

SHP2 Inhibition of Tested Compounds

| Example | | SHP2 Allosteric Biochem: $IC_{50}$ (nM) |
|---|---|---|
| 1 | [structure with Cl, Cl, OH, pyridine, piperidine-spirocyclopentane-NH2, OH] | 210 |

TABLE 1-continued

SHP2 Inhibition of Tested Compounds

| Example | | SHP2 Allosteric Biochem: IC$_{50}$ (nM) |
| --- | --- | --- |
| 2 | (structure) | 37 |
| 3 | (structure) | 740 |
| 4 | (structure) | 69 |
| 5 | (structure) | 210 |

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A compound of Formula I-Y1:

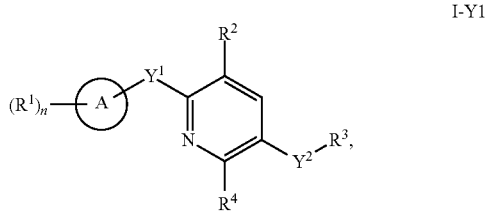

I-Y1 or a pharmaceutically acceptable salt, solvate, hydrate, or stereoisomer thereof, wherein:

A is a 5- to 12-membered monocyclic or polycyclic aryl or heteroaryl;
$Y^1$ is —S— or a direct bond;
$Y^2$ is —NR$^a$; wherein the bond on the left side of $Y^2$, as drawn, is bound to the pyridine ring and the bond on the right side of the $Y^2$ moiety, as drawn, is bound to $R^3$;
$R^1$ is independently, at each occurrence, —H, —C$_1$-C$_6$alkyl, —OH, halogen, or —NH$_2$;
$R^2$ is —OH or —C$_1$-C$_6$alkyl;
$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, —CF$_3$, —CHF$_2$, or —CH$_2$F;
$R^4$ is —H, or —C$_1$-C$_6$alkyl, wherein each alkyl is optionally substituted with one or more —OH or halogen;
n is independently, at each occurrence, 0, 1, 2, 3, 4, 5, 6, 7, 8, 9, or 10.

2. The compound of claim 1, or a pharmaceutically acceptable salt, solvate, hydrate, or stereoisomer thereof, wherein $Y^1$ is —S—.

3. The compound of claim 1, or a pharmaceutically acceptable salt, solvate, hydrate, or stereoisomer thereof, wherein $Y^1$ is a direct bond.

4. The compound of claim 1, or a pharmaceutically acceptable salt, solvate, hydrate, or stereoisomer thereof, wherein $R^3$ and $R^a$ together with the atom to which they are attached combine to form a 3- to 12-membered monocyclic heterocycle, which is optionally substituted with one or more —C$_1$-C$_6$alkyl, —OH, —NH$_2$ —CF$_3$, —CHF$_2$, or —CH$_2$F.

5. The compound of claim 1, or a pharmaceutically acceptable salt, solvate, hydrate, or stereoisomer thereof, wherein $R^3$ and $R^a$ together with the atoms to which they are attached combine to form a 3- to 12-membered polycyclic heterocycle, which is optionally substituted with one or more —C$_1$-C$_6$alkyl, —OH, —NH$_2$ —CF$_3$, —CHF$_2$, or —CH$_2$F.

6. The compound of claim 1, or a pharmaceutically acceptable salt, solvate, hydrate, or stereoisomer thereof, wherein $R^3$ and $R^a$ together with the atoms to which they are attached combine to form a 5- to 12-membered spiroheterocycle, which is optionally substituted with one or more —C$_1$-C$_6$alkyl, —OH, —NH$_2$ —CF$_3$, —CHF$_2$, or —CH$_2$F.

7. The compound of claim 1, or a pharmaceutically acceptable salt, solvate, hydrate, or stereoisomer thereof, wherein A is a monocyclic or polycyclic aryl.

8. The compound of claim 1, or a pharmaceutically acceptable salt, solvate, hydrate, or stereoisomer thereof, wherein A is a monocyclic or polycyclic heteroaryl.

9. The compound of claim 1, or a pharmaceutically acceptable salt, solvate, hydrate, or stereoisomer thereof, wherein $R^1$ is independently, at each occurrence, —H, —C$_1$-C$_6$alkyl, halogen, or —NH$_2$.

10. The compound of claim 1, or a pharmaceutically acceptable salt, solvate, hydrate, or stereoisomer thereof, wherein $R^2$ is —OH.

11. The compound of claim 1, or a pharmaceutically acceptable salt, solvate, hydrate, or stereoisomer thereof, wherein $R^2$ is —C$_1$-C$_6$alkyl.

12. The compound of claim 1, or a pharmaceutically acceptable salt, solvate, hydrate, or stereoisomer thereof, wherein $R^4$ is —C$_1$-C$_6$alkyl, which is optionally substituted with one or more —OH, —NH$_2$, halogen, or oxo.

13. The compound of claim 12, or a pharmaceutically acceptable salt, solvate, hydrate, or stereoisomer thereof, wherein $R^4$ is —C$_1$-C$_6$alkyl, which is substituted with one or more —OH.

14. A compound, or a pharmaceutically acceptable salt, solvate, hydrate, or stereoisomer thereof, selected from the group consisting of:
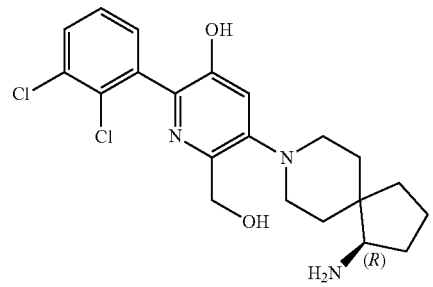
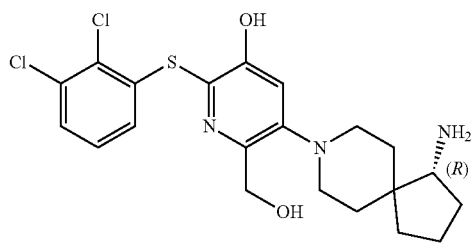
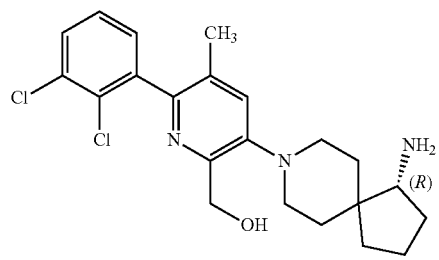
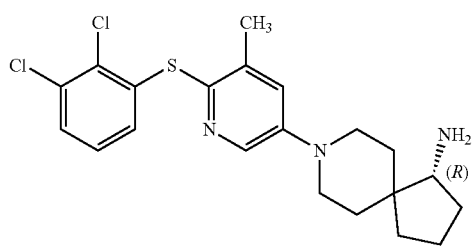
-continued
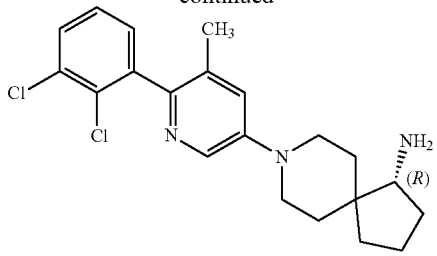
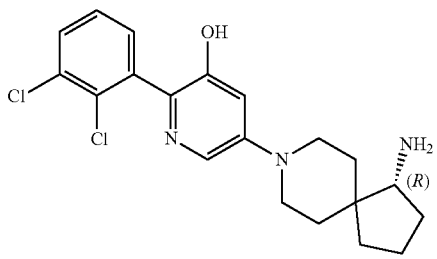
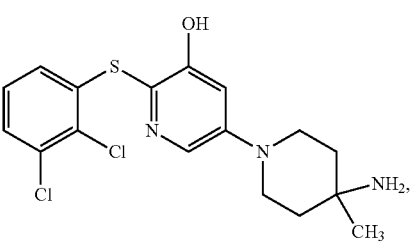
and
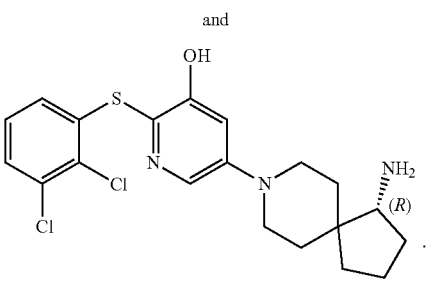
.
15. A compound, or a pharmaceutically acceptable salt, solvate, hydrate, or stereoisomer thereof, selected from the group consisting of:
| Example |
| --- |
| 1 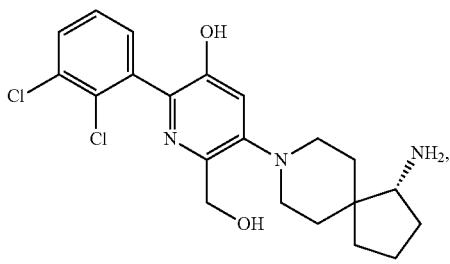 [SMILES: N[C@@H]1CCCC12CCN(c1cc(O)c(-c3cccc(Cl)c3Cl)nc1CO)CC2] |

| Example | |
|---|---|
| 2 | 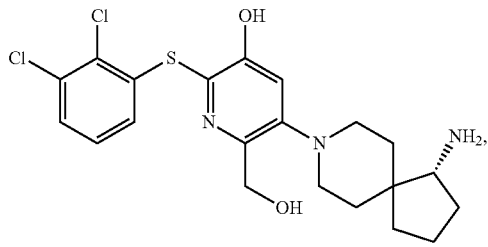 [SMILES: N[C@@H]1CCCC12CCN(c1cc(O)c(Sc3cccc(Cl)c3Cl)nc1CO)CC2] |
| 3 | 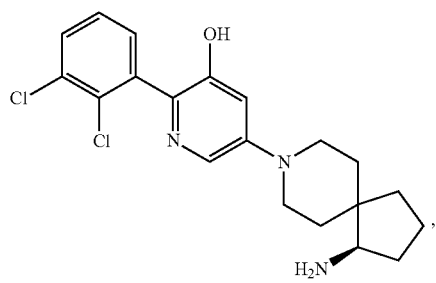 |
| 4 | 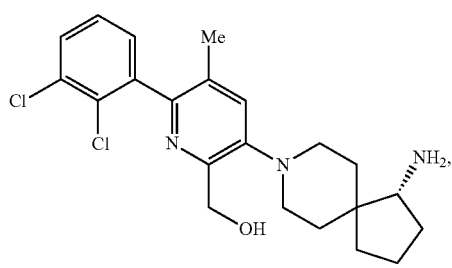 [SMILES: Cc1cc(N2CCC3(CCC[C@H]3N)CC2)c(CO)nc1-c1cccc(Cl)c1Cl] |
| 5 | 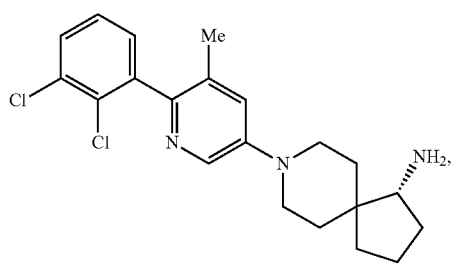 [SMILES: Cc1cc(N2CCC3(CCC[C@H]3N)CC2)cnc1-c1cccc(Cl)c1Cl] |
| 6 | 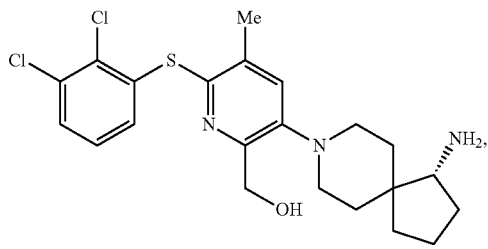 [SMILES: Cc1cc(N2CCC3(CCC[C@H]3N)CC2)c(CO)nc1Sc1cccc(Cl)c1Cl] |
| 7 | 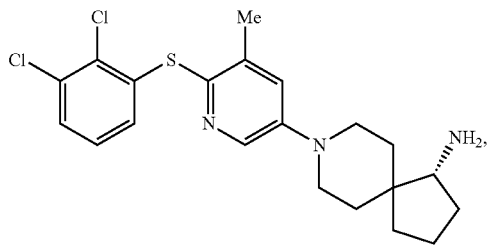 [SMILES: Cc1cc(N2CCC3(CCC[C@H]3N)CC2)cnc1Sc1cccc(Cl)c1Cl] |

| Example | |
|---|---|
| 8 | 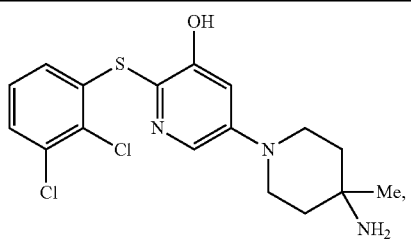 |
| 9 | 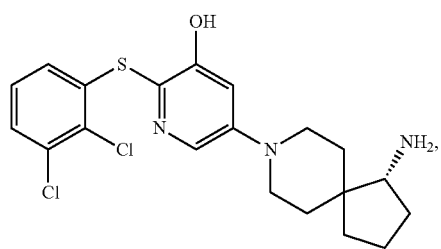 [SMILES: N[C@@H]1CCCC12CCN(c1cnc(Sc3cccc(Cl)c3Cl)c(O)c1)CC2] |
| 10 | 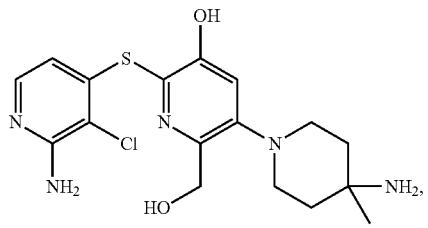 [SMILES: CC1(N)CCN(c2cc(O)c(Sc3ccnc(N)c3Cl)nc2CO)CC1] |
| 11 | 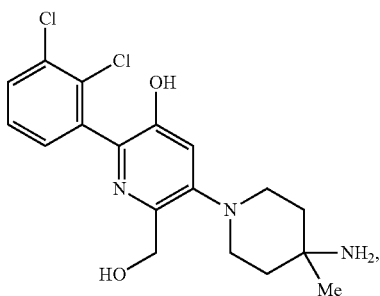 [SMILES: CC1(N)CCN(c2cc(O)c(-c3cccc(Cl)c3Cl)nc2CO)CC1] |
| 12 | 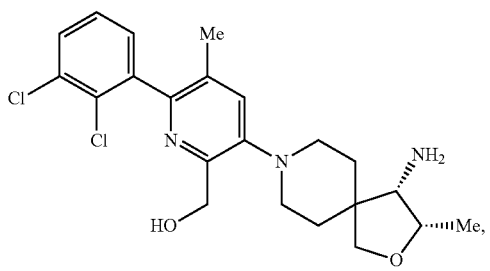 [SMILES: Cc1cc(N2CCC3(CC2)CO[C@@H](C)[C@H]3N)c(CO)nc1-c1cccc(Cl)c1Cl] |
| 13 | 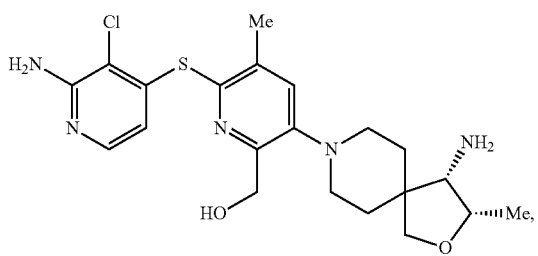 [SMILES: Cc1cc(N2CCC3(CC2)CO[C@@H](C)[C@H]3N)c(CO)nc1Sc1ccnc(N)c1Cl] |

| Example | |
|---|---|
| 14 | 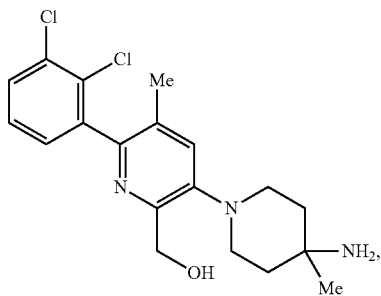 [SMILES: Cc1cc(N2CCC(C)(N)CC2)c(CO)nc1-c1cccc(Cl)c1Cl] |
| 15 | 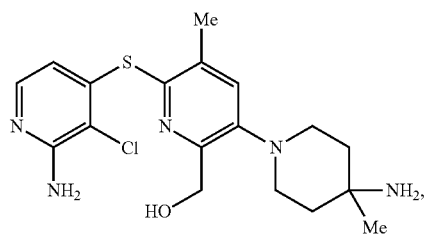 [SMILES: Cc1cc(N2CCC(C)(N)CC2)c(CO)nc1Sc1ccnc(N)c1Cl] |
| 16 | 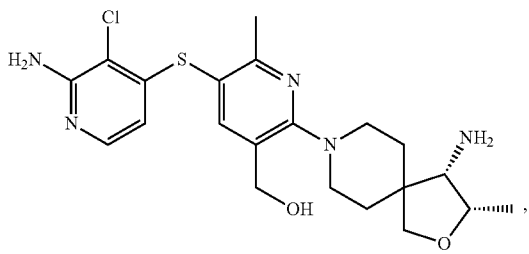 |
| 17 | 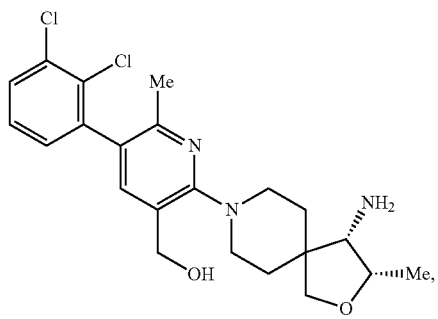 [SMILES: Cc1nc(N2CCC3(CC2)CO[C@@H](C)[C@H]3N)c(CO)cc1-c1cccc(Cl)c1Cl] |
| 18 | 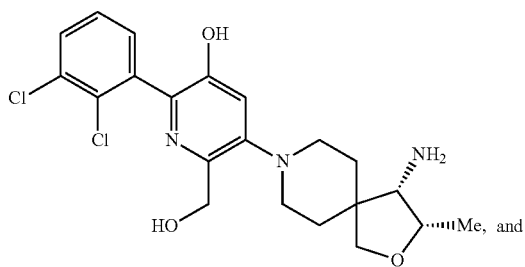 [SMILES: C[C@@H]1OCC2(CCN(c3cc(O)c(-c4cccc(Cl)c4Cl)nc3CO)CC2)[C@@H]1N ; "and"] |

| Example | | |
|---|---|---|
| 19 | 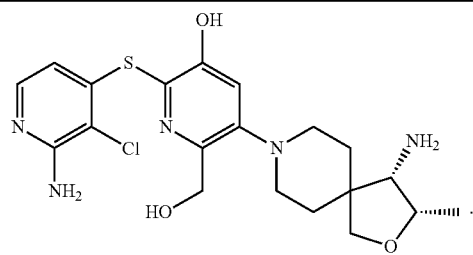 | 15 |
16. A pharmaceutical composition comprising a compound of claim 1, or a pharmaceutically acceptable salt, solvate, hydrate, or stereoisomer thereof, and a pharmaceutically acceptable carrier.
\* \* \* \* \*